United States Patent [19]

Amuti et al.

[11] Patent Number: 5,602,077
[45] Date of Patent: Feb. 11, 1997

[54] PYRIMIDINE COMPOUNDS AS HERBICIDES

[75] Inventors: Kofi S. Amuti, Wilmington; Wonpyo Hong, Hockessin, both of Del.; Joseph E. Semple, San Diego, Calif.

[73] Assignee: E. I. Du Pont de Nemours and Company, Wilmington, Del.

[21] Appl. No.: 256,339

[22] PCT Filed: Dec. 30, 1992

[86] PCT No.: PCT/US92/11330

§ 371 Date: Jul. 13, 1994

§ 102(e) Date: Jul. 13, 1994

[87] PCT Pub. No.: WO93/14073

PCT Pub. Date: Jul. 22, 1993

Related U.S. Application Data

[63] Continuation-in-part of Ser. No. 821,118, Jan. 15, 1992, abandoned.

[51] Int. Cl.[6] .............. C07D 239/553; C07D 239/557; C07D 239/545; A01N 43/54
[52] U.S. Cl. .............. 504/243; 544/311; 544/312; 544/313; 544/314
[58] Field of Search .............. 544/253, 311, 544/312, 313, 314; 504/243

[56] References Cited

U.S. PATENT DOCUMENTS

| | | | |
|---|---|---|---|
| 4,056,527 | 11/1977 | Schlee et al. | 544/194 |
| 4,859,229 | 8/1989 | Wenger et al. | 71/92 |

FOREIGN PATENT DOCUMENTS

| | | |
|---|---|---|
| 0255047 | 2/1988 | European Pat. Off. |
| 0260621 | 3/1988 | European Pat. Off. |
| 0438209 | 7/1991 | European Pat. Off. |
| 0408382 | 11/1991 | European Pat. Off. |
| 0476697 | 3/1992 | European Pat. Off. |
| 3712782 | 11/1988 | Germany |
| 3-77874 | 4/1991 | Japan |
| WO91/07392 | 5/1991 | WIPO |
| WO91/07393 | 5/1991 | WIPO |

OTHER PUBLICATIONS

Fukuda et al, *Chemical Abstracts*, 116, Abstract No. 59391v, 1992.

*Primary Examiner*—John M. Ford

[57] ABSTRACT

A method is disclosed for controlling the growth of undesired vegetation in a plantation crop by applying to the locus of the crop an effective amount of a compound of formula I wherein Q is and A, $R^1$, $R^2$, $R^3$, $R^4$, X, Y and Z are as defined in the disclosure. Also disclosed are novel substituted heterocyclic compounds and their agriculturally suitable compositions which are generally useful as herbicides, as well as methods of their use as general or selective preemergent or postemergent herbicides, or as plant growth regulants.

16 Claims, No Drawings

PYRIMIDINE COMPOUNDS AS HERBICIDES

CROSS-REFERENCE TO RELATED APPLICATION

This application is 371 of PCT/US92/11330, filed Dec. 30, 1992, and published as WO93/14073 Jul. 22, 1993, and a continuation-in-part of application U.S. Ser. No. 07/821,118, filed Jan. 15, 1992, now abandoned.

FIELD OF THE INVENTION

This invention relates to novel substituted heterocyclic compounds and a method for controlling undesired vegetation in crops including plantation and specialty crops. Some of the compounds of the instant invention have been disclosed previously for use generally as herbicides, but these disclosures provide no teachings for use of these compounds as herbicides in plantation crops.

BACKGROUND OF THE INVENTION

U.S. Pat. No. 4,859,229 discloses herbicidal utility in "cotton and soya" cultivations for compounds of the formula

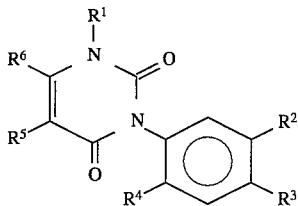

wherein, inter alia $R^1$ is H, $C_1$-$C_4$ alkyl, $C_1$-$C_4$ haloalkyl, formyl or $C_2$-$C_6$ alkanoyl;

$R^2$ is (in part) an ether group;

$R^3$ is H or CN;

$R^4$ is H or halogen;

$R^5$ is H, halogen or $C_1$-$C_4$ alkyl;

$R^6$ is $C_1$-$C_4$ alkyl or $C_1$-$C_4$ haloalkyl; and $R^5$ and $R^6$ together are tri- or tetramethylene.

The instant invention provides a method for controlling undesired vegetation in plantation and specialty crops. Many of the compounds of the instant invention have been previously disclosed for use generally as herbicides, and such disclosures are found in U.S. Pat. No. 4,859,229, EP-A-438,209, JP 3-77,874 and EP-A-408,382. There are, however, no teachings for the use of these compounds as herbicides in plantation and specialty crops such as citrus, sugarcane, coffee, banana, oil palm, loblolly pine, rubber, cocoa, grapes, plantain, pineapple, fruit trees such as apples, and nut trees. These crops are important markets and are cultivated particularly in regions of the Pacific rim and South America. Citrus, sugarcane and loblolly pine also are grown elsewhere.

The yields of selected crops such as citrus, sugarcane, coffee, banana, oil palm, loblolly pine, rubber, cocoa, grapes, fruit trees and Bermudagrass tend to be lessened by undesired plantings such as crabgrass, johnson grass, guineagrass and the like. In addition, the yields of these crops tend to be reduced by crop plants such as corn, cotton, wheat, rice, and the like. A need therefore exists for controlling these types of plantings to improve the yields of selected crops such as those mentioned above.

This invention also provides novel substituted heterocyclic compounds and their agriculturally suitable compositions which are generally useful as herbicides, as well as methods of their use as general or selective preemergent or postemergent herbicides, or as plant growth regulants.

New compounds effective for controlling the growth of undesired vegetation are in constant demand. In the most common situation, such compounds are sought to selectively control the growth of weeds in useful crops such as sugarcane, citrus, oil palm, cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

SUMMARY OF THE INVENTION

This invention comprises a method for controlling the growth of undesired vegetation in a plantation crop by applying to the locus of the crop an effective amount of a compound of Formula I

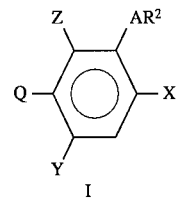

wherein

Q is 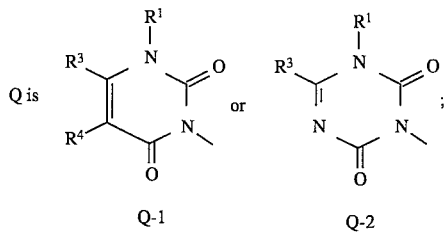

A is O or S;

$R^1$ is $C_1$-$C_4$ alkyl optionally substituted with one or more halogen, $OR^5$, $SR^6$ or CN; $C_3$-$C_6$ alkenyl or $C_3$-$C_6$ alkynyl, each optionally substituted with 1–3 halogen; formyl; or $C_2$-$C_6$ alkanoyl;

$R^2$ is H, isopropyl, allyl, propargyl, $CH(CH_3)C\equiv CH$, benzyl, $CHR^7CO_2R^8$ or may be taken together with Z;

$R^3$ is $C_1$-$C_4$ alkyl, $C_1$-$C_4$ haloalkyl or $N(CH_3)_2$;

$R^4$ is H or halogen;

$R^3$ and $R^4$ may be taken together as —$(CH_2)_3$— or —$(CH_2)_4$—;

$R^5$ and $R^6$ are independently H or $C_1$-$C_3$ alkyl;

$R^7$ and $R^8$ are independently $C_1$-$C_2$ alkyl;

X is Cl or Br;

Y is F or Cl;

Z is H or may be taken together with $R^2$ as $$-CH_2\overset{|}{C}HR^9$$

such that the linking A atom is attached to the methine carbon;

$R^9$ is $C_1$-$C_3$ alkyl, $C_1$-$C_3$ haloalkyl, cyclopropyl, vinyl, $C_2$ alkynyl, CN, $C(O)R^{10}$, $CO_2R^{10}$, $CONR^{10}R^{11}$, $CR^{12}R^{13}C(O)R^{10}$, $CR^{12}R^{13}CO_2R^{10}$, $CR^{12}R^{13}CONR^{10}R^{11}$, $CHR^{12}OH$, $CHR^{12}OC(O)R^{10}$ or $CHR^{12}OC(O)NR^{10}R^{11}$; and $R^{10}$, $R^{11}$, $R^{12}$ and $R^{13}$ are independently H or $C_1$-$C_3$ alkyl.

Preferred for reasons including greater herbicidal efficacy are:

1) The method wherein for Compounds of Formula I
   $R^1$ is $C_1$-$C_3$ alkyl optionally substituted with 1 to 3 F atoms or Cl atoms, $O(C_1$-$C_2$ alkyl), S ($C_1$-$C_2$ alkyl) or CN; $C_3$-$C_4$ alkenyl optionally substituted with 1 to 3 F atoms or Cl atoms; $C_3$-$C_4$ alkynyl; or $C_2$-$C_3$ alkanoyl;
   $R^2$ is H, isopropyl, allyl, propargyl, $CH(CH_3)C\equiv CH$, $CHR^7CO_2R^8$ or may be taken together with Z;
   $R^3$ is $C_1$-$C_2$ alkyl, $C_1$-$C_2$ haloalkyl or $N(CH_3)_2$;
   $R^4$ is H, F, Cl or Br;
   $R^3$ and $R^4$ may be taken together as $-(CH_2)_3-$ or $-(CH_2)_4-$; and
   X is Cl.

2) The method of Preferred 1 wherein
   $R^1$ is $CH_3$ optionally substituted with 1 to 3 F atoms or Cl atoms; $CH_2CN$; allyl; or propargyl;
   $R^3$ is $CF_3$; and
   $R^4$ is H.

3) The method of Preferred 2 wherein
   $R^9$ is $CH_3$;
   A is O; and
   Q is Q-1.

Specifically Preferred for reasons of greatest herbicidal efficacy are the method of Preferred 3 which are the use of the compounds:

3-[4-chloro-2-fluoro-5-[(2-propynyl)oxy]phenyl]-1-methyl-6-(trifluoromethyl)-2,4(1H,3H)-pyrimidinedione;

3-[4-chloro-2-fluoro-5-(2-propenyloxy)phenyl]-1-methyl-6-(trifluoromethyl)-2,4(1H,3H)-pyrimidinedione;

3-(5,7-dichloro-2,3-dihydro-2-methyl-4-benzofuranyl)-1-methyl-6-(trifluoromethyl)-2,4(1H,3H)-pyrimidinedione; and 3-(7-choro-5-fluoro-2,3-dihydro-2-methyl-4-benzofuranyl)-1-methyl-6-(trifluoromethyl)-2,4(1H,3H)-pyrimidinedione;

and the method of Preferred 2 which is the use of the compound:

3-[4-chloro-2-fluoro-5-[(2-propynyl)oxy]phenyl]-6-dimethylamino-1-methyl-1,3,5-triazine-2,4(1H,3H)-dione.

This invention also comprises compounds of Formulas II and III, agriculturally suitable compositions containing them, and their use as preemergent and/or postemergent herbicides.

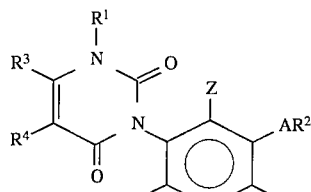

II

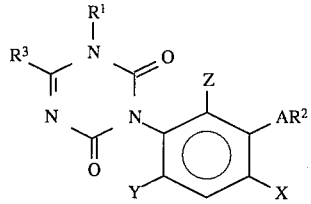

III wherein

A is O or S;

$R^1$ is $C_1$-$C_4$ alkyl optionally substituted with one or more halogen, $OR^5$, $SR^6$ or CN; $C_3$-$C_6$ alkenyl or $C_3$-$C_6$ alkynyl, each optionally substituted with 1–3 halogens; formyl; or $C_2$-$C_6$ alkanoyl;

$R^2$ is H, isopropyl, allyl, propargyl, $CH(CH_3)C\equiv CH$, benzyl, $CHR^7CO_2R^8$ or may be taken together with Z;

$R^3$ is $C_1$-$C_4$ alkyl, $C_1$-$C_4$ haloalkyl or $N(CH_3)_2$;

$R^4$ is H or halogen;

$R^3$ and $R^4$ may be taken together as $-(CH_2)_3-$ or $-(CH_2)_4-$;

$R^5$ and $R^6$ are independently H or $C_1$-$C_3$ alkyl;

$R^7$ and $R^8$ are independently $C_1$-$C_2$ alkyl;

X is Cl or Br;

Y is F or Cl;

Z is H or may be taken together with $R^2$ as $$-CH_2\overset{|}{C}HR^9$$

such that the linking A atom is attached to the methine carbon; and $R^9$ is $C_1$-$C_3$ alkyl, $C_1$-$C_3$ haloalkyl, cyclopropyl, vinyl, $C_2$ alkynyl, CN, $C(O)R^{10}$, $CO_2R^{10}$, $CONR^{10}R^{11}$, $CR^{12}R^{13}C(O)R^{10}$, $CR^{12}R^{13}CO_2R^{10}$, $CR^{12}R^{13}CONR^{10}R^{11}$, $CHR^{12}OH$, $CHR^{12}OC(O)R^{10}$ or $CHR^{12}OC(O) NR^{10}R^{11}$; and $R^{10}$, $R^{11}$, $R^{12}$ and $R^{13}$ are independently H or $C_1$-$C_3$ alkyl;

provided that 1) in compounds of Formula II, when $R^1$ is $C_1$-$C_4$ alkyl optionally substituted with halogen, $OR^5$ or CN; $C_3$-$C_4$ alkenyl; formyl; or $C_2$-$C_6$ alkanoyl; $R^3$ is $C_1$-$C_4$ haloalkyl; and $R^5$ is $C_1$-$C_3$ alkyl; then $R^2$ is benzyl or taken together with Z;

2) in compounds of Formula II, when $R^1$ is $CH_2OH$ or $C_1$-$C_3$ alkyl optionally substituted with halogen; $R^3$ is $C_1$-$C_4$ haloalkyl; and A is S; then $R^2$ is taken together with Z;

3) in compounds of Formula III, when $R^1$ is $C_1$-$C_4$ alkyl and $R^3$ is $CH_3$ or $CF_3$ then $R^2$ is benzyl or taken together with Z;

4) in compounds of Formula II, when $R^1$ is $C_1$-$C_4$ alkyl optionally substituted with halogen; formyl; or $C_2$-$C_6$ alkanoyl; then $R^2$ is taken together with Z.

Preferred for reasons including ease of synthesis and/or greater herbicidal efficacy are:

1) Compounds of Formulas II and III wherein
   $R^1$ is $C_1$-$C_3$ alkyl optionally substituted with 1 to 3 F atoms or Cl atoms, $O(C_1$-$C_2$ alkyl), $S(C_1$-$C_2$ alkyl) or CN; $C_3$-$C_4$ alkenyl optionally substituted with 1 to 3 F atoms or Cl atoms; $C_3$-$C_4$ alkynyl; or $C_2$-$C_3$ alkanoyl;
   $R^2$ is H, isopropyl, allyl, propargyl, $CH(CH_3)C\equiv CH$, $CHR^7CO_2R^8$ or may be taken together with Z;
   $R^3$ is $C_1$-$C_2$ alkyl, $C_1$-$C_2$ haloalkyl or $N(CH_3)_2$;
   $R^4$ is H, F, Cl or Br;
   $R^3$ and $R^4$ may be taken together as —$(CH_2)_3$— or —$(CH_2)_4$—; and
   X is Cl.

2) Compounds of Preferred 1 wherein
   $R^1$ is $CH_3$ optionally substituted with 1 to 3 F atoms or Cl atoms; $CH_2CN$; allyl; or propargyl;
   $R^3$ is $CF_3$; and
   $R_4$ is H.

3) Compounds of Preferred 2 wherein the compound is of Formula II;
   $R^9$ is $CH_3$; and
   A is O.

Specifically Preferred for reasons of ease of synthesis and/or greatest herbicidal efficacy are the compound of Preferred 2 which is:

3-[4-chloro-2-fluoro-5-[(2-propynyl)oxy]phenyl]-6-(dimethylamino-1-methyl-1,3,5-triazine-2,4(1H,3H)-dione; and the compounds of Preferred 3 which are 3-(5,7-dichloro-2,3-dihydro-2-methyl-4-benzofuranyl)-1-methyl-6-(trifluoromethyl)-2,4(1H,3H)-pyrimidinedione; and 3-(7-choro-5-fluoro-2,3-dihydro-2-methyl-4-benzofuranyl)-1-methyl-6-(trifluoromethyl)-2,4(1H,3H)-pyrimidinedione.

In the above definitions, the term "alkyl", used either alone or in compound words such as "haloalkyl", includes straight chain or branched alkyl, e.g., methyl, ethyl, n-propyl, isopropyl or the different butyl isomers. Alkenyl includes straight chain or branched alkenes, e.g., 1-propenyl, 2-propenyl, 3-propenyl and the different butenyl isomers. The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

DETAILED DESCRIPTION OF THE INVENTION

Many of the compounds of Formula I wherein Z and $R^2$ are not taken together can be prepared according to the procedures of U.S. Pat. No. 4,859,229 and U.S. Pat. No. 3,902,887, the disclosures of which are herein incorporated by reference.

Schemes 1 to 4 illustrate the preparation of compounds of Formula II wherein Z and $R^2$ are taken together.

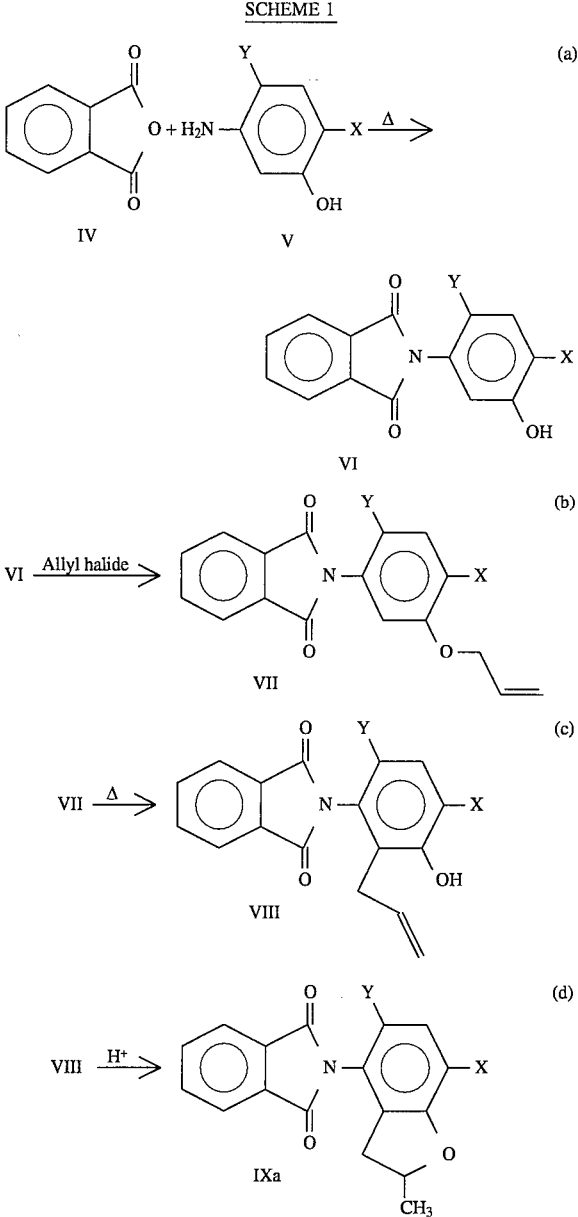

The dihydrofuran ring of compounds of Formula II can be prepared according to the procedure of U.S. Pat. No. 4,881,967 by Claisen rearrangement of allyl ether VII followed by cyclization as shown in Scheme 1, Equations (c) and (d). The rearrangement and cyclization normally require high temperatures ranging from 100° C. to 200° C. Therefore, it is preferable to perform this process at an early stage with an inert protecting group on nitrogen. For this reason, phthalimide VII is prepared via treatment of hydroxyaniline V with phthalic anhydride IV followed by allylation of the hydroxy group of VI in the presence of a weak base such as potassium carbonate (Scheme 1, Equations (a) and (b)).

Alternatively, the compound VII can be prepared by allylation of V first followed by treatment with phthalic anhydride IV.

The rearrangement of VII can be effected by heating in an inert solvent such as N,N-dimethylaniline or o-dichlorobenzene at a temperature of about 100° C. to 200° C. This Claisen rearrangement can also proceed with titanium tetrachloride and N-trimethylsilylacetanilide at ambient temperature in an inert solvent such as dichloromethane (Narasaka, K., Bald E., and Mukaiyama T.; *Chemistry Letters* 1975, 1041). The cyclization of VIII to give IXa can be effected by refluxing a solution of phenol VIII in an inert solvent, such as xylene, containing a catalytic to stoichiometric amount of acid such as p-toluenesulfonic acid under Dean-Stark apparatus at a temperature range of from about 120° C. to 180° C. (Scheme 1, Equation (d)).

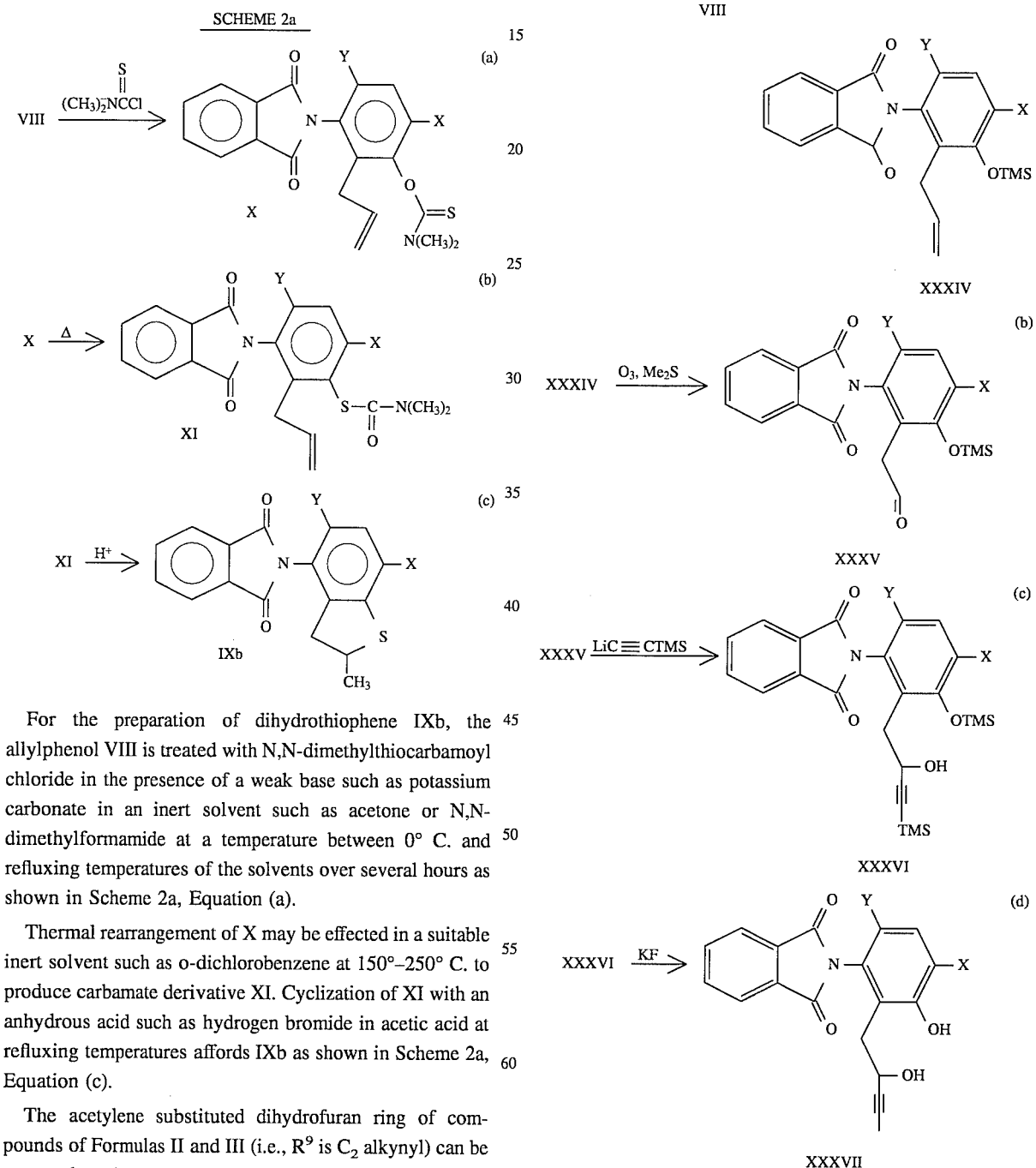

For the preparation of dihydrothiophene IXb, the allylphenol VIII is treated with N,N-dimethylthiocarbamoyl chloride in the presence of a weak base such as potassium carbonate in an inert solvent such as acetone or N,N-dimethylformamide at a temperature between 0° C. and refluxing temperatures of the solvents over several hours as shown in Scheme 2a, Equation (a).

Thermal rearrangement of X may be effected in a suitable inert solvent such as o-dichlorobenzene at 150°–250° C. to produce carbamate derivative XI. Cyclization of XI with an anhydrous acid such as hydrogen bromide in acetic acid at refluxing temperatures affords IXb as shown in Scheme 2a, Equation (c).

The acetylene substituted dihydrofuran ring of compounds of Formulas II and III (i.e., $R^9$ is $C_2$ alkynyl) can be prepared as shown in Scheme 2b.

-continued
SCHEME 2b

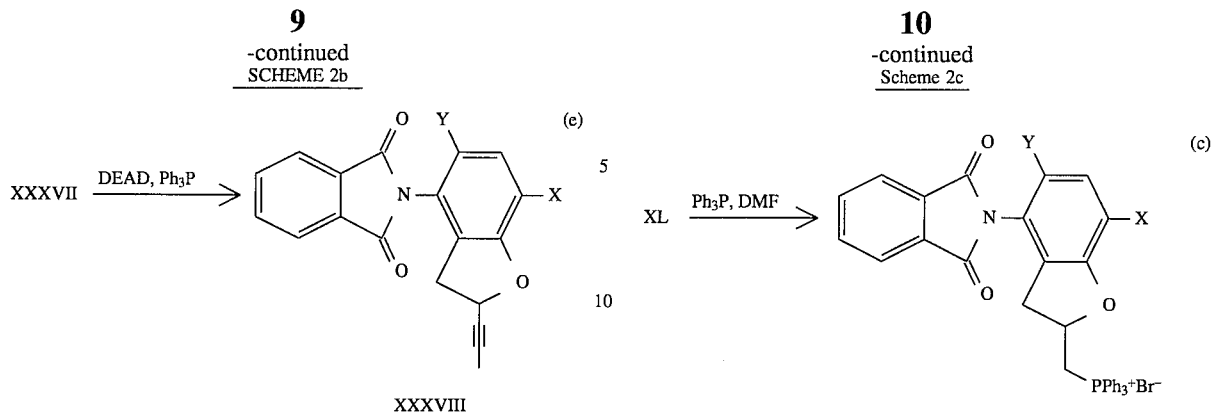

The hydroxyl group of VIII of Scheme 1, Equation (c) can be protected by a silicon protecting group using reagents such as trimethylsilyl chloride or t-butyldimethylsilyl chloride to give XXXIV. Then the reductive ozonolysis of XXXIV gives aldehyde XXXV. The diol XXXVI can be prepared by the treatment of aldehyde XXXV with lithium salt of trimethylsilylacetylene. The deprotections of both silyl protecting groups of XXXVI can be accomplished using fluoride ions such as potassium fluoride. The acetylenic hydrofuran XXXVIII can be prepared from the diol XXXVII by Mitsunobu condition using diethyl azodicarboxylate (DEAD) and triphenylphosphine according to the known procedure (Macor, J., Ryan, K., and Newman, M.; *Tetrahedron* 1992, 48, 1039).

The vinyl group substituted dihydrofuran ring of compounds of Formula II and III can be prepared as shown in Scheme 2c.

Scheme 2c

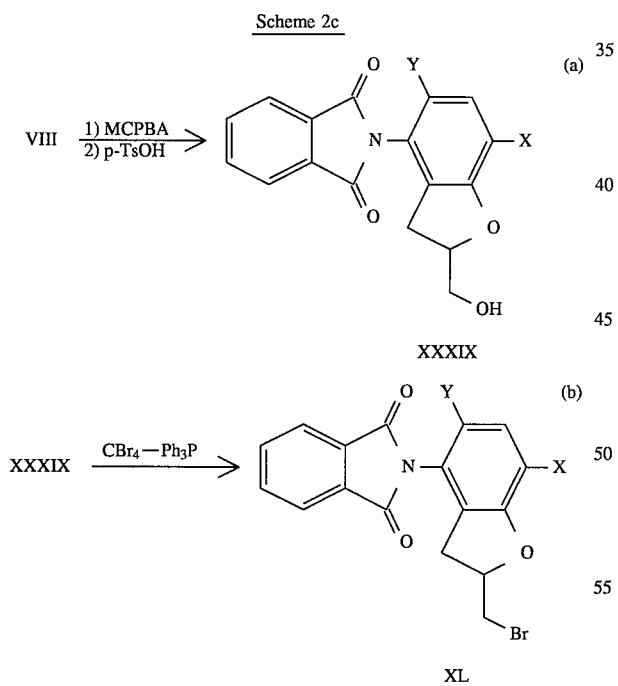

-continued
Scheme 2c

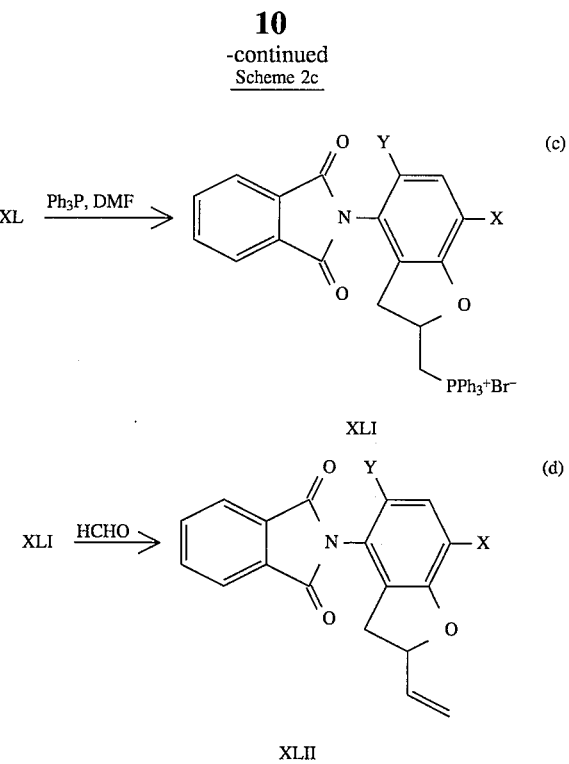

The hydroxymethyl hydrofuran XXXIX can be prepared by treatment of VIII with m-chloroperbenzoic acid (MCPBA) followed by p-toluenesulfonic acid. The treatment of XXXIX with carbon tetrabromide and triphenylphosphine gives bromomethyl hydrofuran XL. The Wittig reagent XLI can be prepared by the treatment of XL with triphenylghosphine in an inert solvent such as DMF. The vinylic hydrofuran XLII can be prepared by Wittig reaction of XLI and formaldehyde.

The hydroxy group of XXXIX can be converted to ketone, carboxylic acid, ester or amide groups by methods well known to those skilled in the art. This transformation can be carried out before or after the phthalimide protecting group is removed. If the protecting group is removed first, then the unprotected aniline derivative is first converted to the uracil or triazinedione ring (as described later) before further conversion of the hydroxyl group.

SCHEME 3

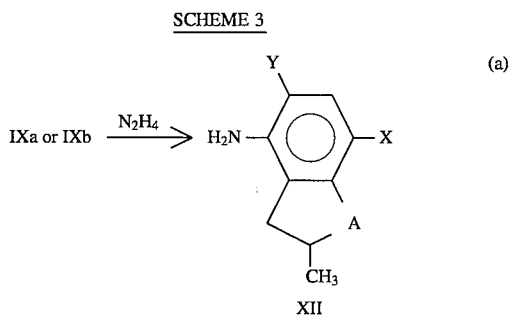

-continued
SCHEME 3

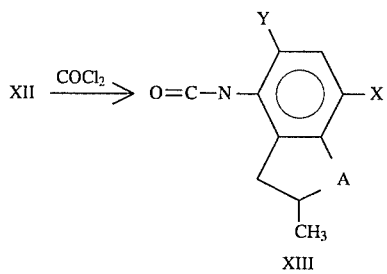

The phthalimide protecting group of IXa or IXb can be removed by hydrazine at ambient temperature to afford aniline XII. The formation of isocyanate XIII is accomplished by treatment of the aniline XII with phosgene or triphosgene in the presence of a base such as triethylamine at ambient temperature, or without base in an inert solvent such as dioxane or toluene at a temperature range of from 60° C. to 120° C. (Scheme 3).

SCHEME 4

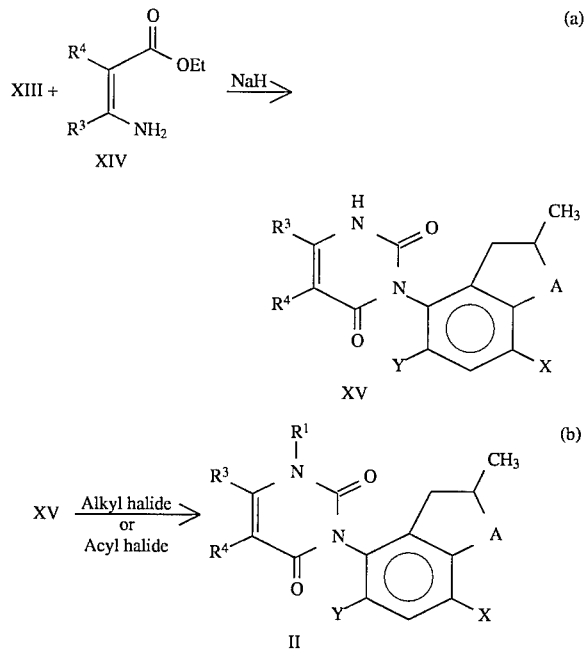

The formation of the uracil ring in compound XV is carried out by the procedure described in U.S. Pat. No. 4,943,309. A suitable salt of an enamine XIV is treated with the isocyanate XIII at low temperature over several hours, typically between −50° C. and −70° C. in an inert solvent such as toluene, and the reaction is continued at ambient temperature for several hours. The alkylation of XV can be accomplished by treatment of XV with $C_{1-4}$ alkyl halide, or $C_{1-4}$ haloalkyl halide, especially the respective chloride or bromide, or sulphate in the presence of a base such as potassium carbonate or sodium hydride in an inert solvent such as acetone or acetonitrile at a temperature range of from about 0° C. to 120° C. The acylation of XV is carried out with acetic anhydride or a $C_{2-6}$ alkanecarboxylic acid halide, in the presence of base such as sodium hydride.

Schemes 5 and 6 illustrate the preparation of compounds of Formula III.

SCHEME 5

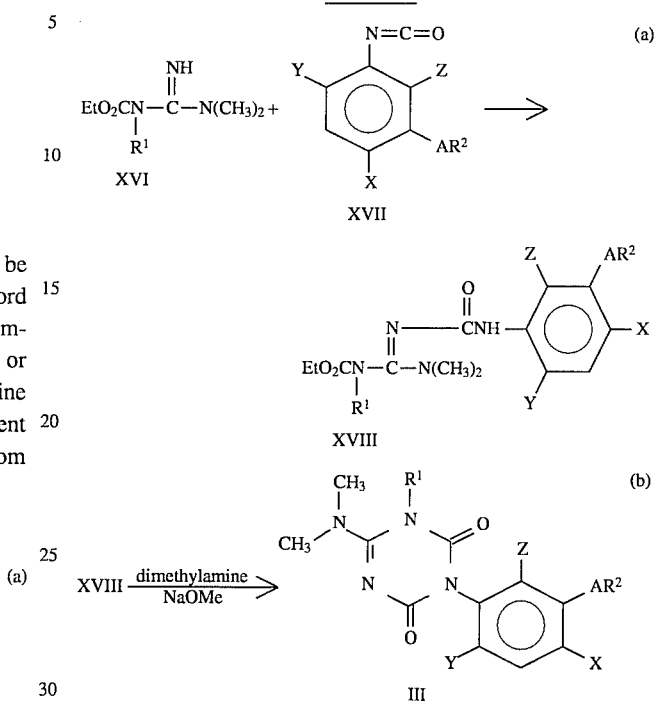

The formation of the triazinedione ring follows the procedure described in U.S. Pat. No. 3,902,887 when $R^3$ is a dimethylamino group as shown in Scheme 5. N-Ethoxycarbonylguanidine XVI is mixed with an isocyanate XVII in an inert solvent, preferably toluene, while the temperature is maintained at 25° C. to 100° C., preferably 55° C. to 80° C. The mixture of slurry containing compound XVIII is cooled, if necessary, to 24° C.–45° C., while dimethylamine is added, either as a gas or a liquid. It is preferred to add the amine at 25° C.–35° C., and it is important to have at least 1.0 molar equivalent and preferably, 1.0 to 2.5 molar equivalents of dimethylamine. Next a ring closure catalyst is added. The catalyst is an alkali metal alkoxide (or hydroxide) and it may be added either as a dry solid or as a solution in the alkanol. Dry sodium methoxide or a solution of sodium methoxide in methanol is a preferred catalyst. The amount of catalyst needed is from 0.1 to 5.0 mole percent of compound XVIII. The ring closure reaction can proceed at a temperature between 0° C. and 120° C. The reaction is rapid and normally complete in less than several hours.

SCHEME 6

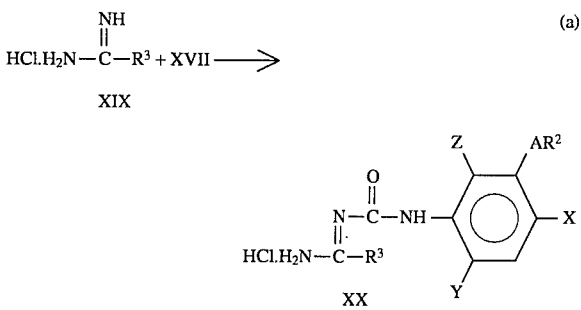

-continued
SCHEME 6

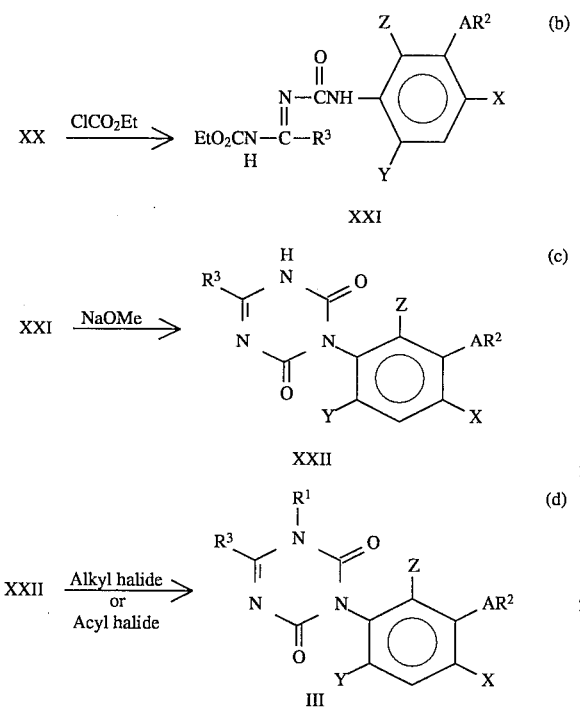

When $R^3$ is $C_1-C_4$ alkyl and $C_1-C_4$ haloalkyl substituents, the formation of the triazinedione ring follows the procedure described by JP 03 77,874 as shown in Scheme 6. Carbamoylation of alkylamidine hydrochloride or haloalkylamidine hydrochloride XIX with isocyanate XVII under the condition described in Scheme 5 or in the presence of NaOH in aqueous acetone gives N-phenylcarbamoyl amidine XX. The cyclocondensation of the resulting compound XX with ethyl chloroformate in the presence of base such as sodium hydride or sodium methoxide in an inert solvent such as tetrahydrofuran gives triazinedione XXII via XXI. The alkylation of XXII can be accomplished by treatment of XXII with $C_{1-4}$ alkyl halide, or $C_1-C_4$ haloalkyl halide, especially the respective chloride, bromide or sulphate in the presence of a base such as potassium carbonate or sodium hydride in an inert solvent such as acetone or acetonitrile at a temperature range of from about 0° C. to 120° C. The acylation of XXII is carried out with acetic anhydride or a $C_2-C_6$ alkanecarboxylic acid halide in the presence of base such as sodium hydride.

SCHEME 7

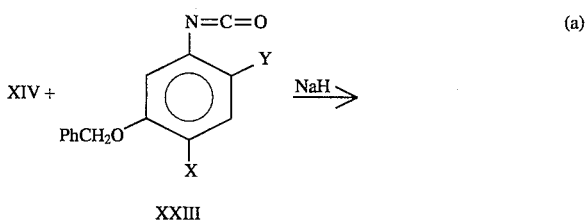

-continued
SCHEME 7

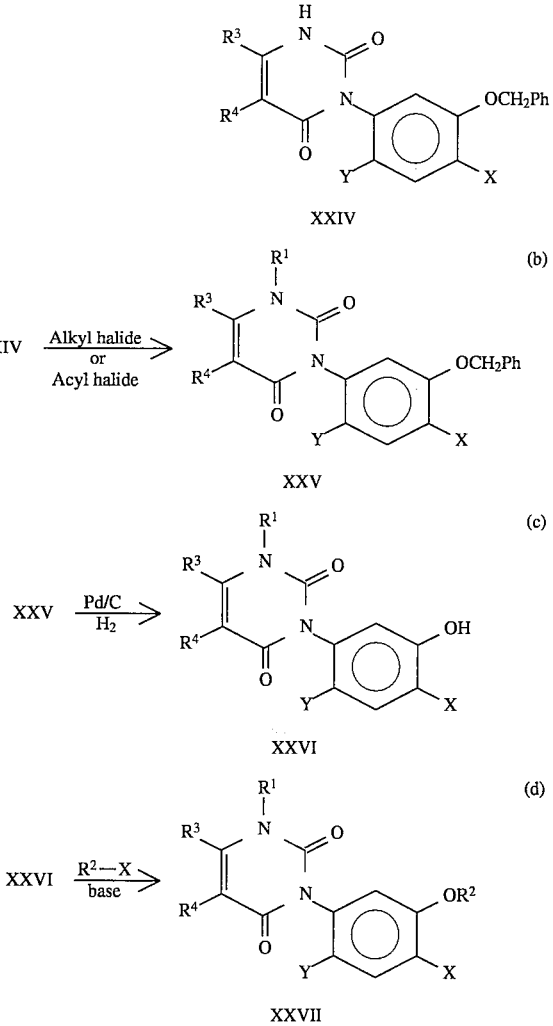

Compounds of Formula II wherein Z is hydrogen and A is oxygen can be prepared according to Scheme 7. Cyclocondensation of enamine XIV can be carried out with benzyl ether protected isocyanate XXIII. The enamine XIV wherein $R^3$ and $R^4$ are taken together as $-(CH_2)_3-$ or $-(CH_2)_4-$ can be prepared according to the known procedure (Kloek, J., and Leschinsky, K.; *J. Org Chem.*, 1978, 43, 1460). Other enamines of Formula XIV wherein $R^3$ and $R^4$ are not taken together can be prepared by one skilled in the art. The resultant uracil XXIV is alkylated or acylated as described previously and benzyl ether XXV can be deprotected easily with 5 to 10% palladium on charcoal under hydrogen pressure ranging from 20 to 50 psi. The resulting phenol XXVI is treated with $C_1-C_4$ alkyl halide, or $C_1-C_4$ haloalkyl halide, especially the respective chloride or bromide in the presence of a base such as potassium carbonate or sodium hydride in an inert solvent such as acetone or acetonitrile at a temperature range of from about 0° C. to 120° C. to give XXVII.

SCHEME 8

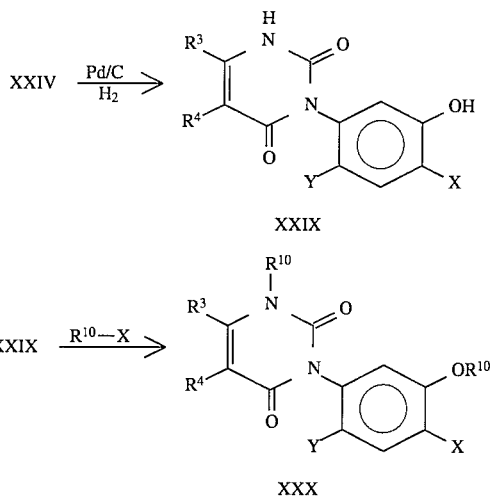

The compound XXX which has two identical $R^{10}$ substituents (wherein $R^{10}$ is isopropyl, allyl or $C_3$-$C_4$ alkynyl) can be prepared by deprotection of benzyl ether XXIV with palladium on charcoal under hydrogen followed by alkylation or acylation in the presence of base as shown in Scheme 8.

SCHEME 9

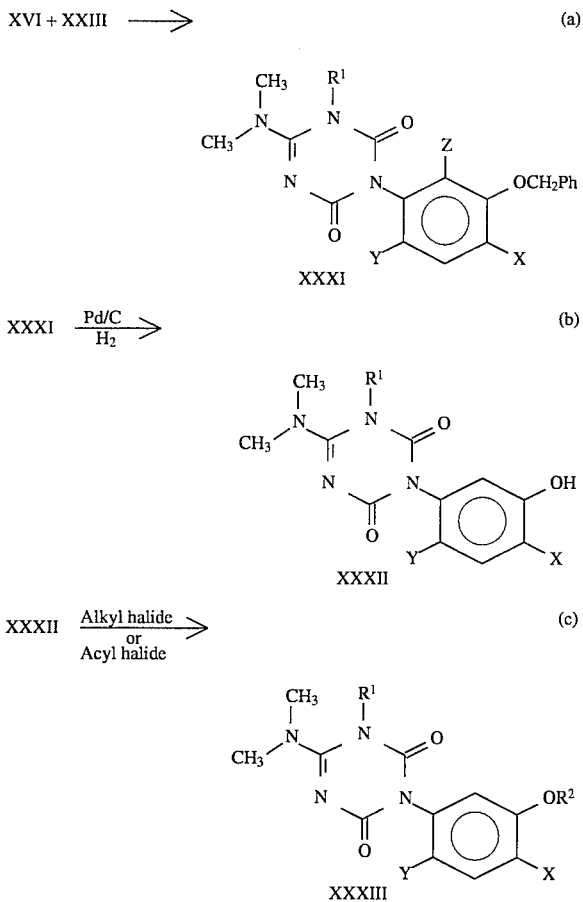

The same procedure can be adopted for the synthesis of triazinediones of Formula III wherein Z is hydrogen and A is oxygen as shown in Scheme 9. The cyclocondensation product XXXI from N-ethoxycarbonylguanidine XVI and benzyl ether protected isocyanate XXIII is treated with palladium on charcoal under hydrogen pressure ranging from 20 to 50 psi followed by alkylation or acylation in the presence of base to give XXXIII.

EXAMPLE 1

Preparation of 3-[4-chloro-2-fluoro-5-[(2-propynyl)-oxy]phenyl]-1-methyl-6-(trifluoromethyl)-2,4(1H, 3H)-pyrimidinedione To a solution of 200 mg (0.59 mmol) of 3-[4-chloro-2-fluoro-5-(hydroxy)phenyl]-1-methyl-6- (trifluoromethyl)-2,4 (1H,3H) -pyrimidinedione in 3 mL of acetonitrile was added 162 mg of potassium carbonate (1.18 mmol) and 131 mL (1.18 mmol) of an 80% solution of propargyl bromide in toluene. It was warmed under reflux for 2 h. The resulting mixture was filtered and the filtrate was concentrated in vacuo to give colorless oil which was flash chromatographed over silica gel, eluting with a 1:4 v:v mixture of ethyl acetate and hexane to give 204 mg of title compound as a white foam: $^1$H-NMR (CDCl$_3$, 200 MHz) ppm 7.35 (d, 1H), 7.0 (d, 1H), 6.4 (s, 1H), 4.78 (d, 2H), 3.58 (s, 3H), 2.6 (d, 1H).

EXAMPLE 2

Preparation of 3-[4-chloro-2-fluoro-5-(hydroxy)phenyl]-1-methyl-6-(trifluoromethyl)-2,4(1H, 3H) -pyrimidinedione A mixture of 1.12 g (2.61 mmol) of 3-[4-chloro-2-fluoro-5-(phenylmethoxy)phenyl]-1-methyl-6-(trifluoromethyl)-2,4(1H,3H)-pyrimidinedione and 220 mg of 10% palladium on charcoal in 40 mL of ethyl acetate was placed in a Paar bottle and was agitated under 45 psi hydrogen over a 20 hour period. It was filtered and washed with 100 mL of ethyl acetate. The filtrate was concentrated in vacuo and the resultant crude product flash chromatographed over silica gel eluting with a 1:4 v:v mixture of ethyl acetate and hexane to give 521 mg of the title compound as a white foam.: $^1$H-NMR (CDCl$_3$, 200 MHz) ppm 7.15 (d, 1H) , 6.9 (d, 1H) , 6.4 (s, 1H), 5.8 (s, 1H), 3.6 (s, 3H).

EXAMPLE 3

Preparation of 3-[4-chloro-2-fluoro-5-(phenylmethoxy)phenyl]-1-methyl-6-(trifluoromethyl)-2,4(1H,3H)-pyrimidinedione A mixture of 1.85 g (4.46 mmol) of 3-[4-chloro-2-fluoro-5-(phenylmethoxy)phenyl]-6-(trifluoromethyl)-2,4(1H, 3H)-pyrimidinedione, 492 µL (5.20 mmol) of dimethylsulfate, and 749 mg (8.92 mmol) of sodium bicarbonate in 20 mL of acetone was warmed under reflux for 3 h. Evaporation removed the solvent to give a viscous residue. It was dissolved in 50 mL of ether and washed twice with 30 mL of water, dried (MgSO$_4$) and concentrated in vacuo to give white solid which was flash chromatographed over silica gel, eluting with a 1:4 v:v mixture of ethyl acetate and hexane to give 1.19 g of the title compound as a white solid, m.p.: 145°–147° C.; $^1$H-NMR (CDCl$_3$, 200 MHz) ppm 7.4 (m, 6H), 6.85 (d, 1H), 6.4 (s, 1H), 5.1 (s, 2H), 3.55 (s, 3H).

EXAMPLE 4

Preparation of 3-[4-chloro-2-fluoro-5-(phenylmethoxy)-phenyl]-6-(trifluoromethyl)-2,4(1H,3H) -pyrimidinedione To a solution of 312 mg (7.82 mmol) of sodium hydride (60% oil dispersion) in 10 mL of N,N-dimethylformamide was added 1.43 g (7.82 mmol) of ethyl-3-amino-4,4,4-trifluorocrotonate in 7 mL of toluene over a period of 30 min at −5° C. The resulting mixture was stirred for an additional 30 min before it was cooled to −70° C. Then a solution of 2.17 g (7.82 mmol) of 4-chloro-2-fluoro-5-(phenylmethoxy)phenyl isocyanate in 7 mL of toluene was added dropwise at a rate that maintained the reaction temperature below −60° C. After the addition, the thick reaction mixture was maintained at −60° C. for an additional 1 h before the cooling bath was removed. The mixture was gradually warmed to room temperature and stirring was continued for 1.5 h. Then the mixture was poured into a solution of 10 mL of concentrated HCl in 200 mL of water. The toluene layer was separated and the aqueous layer was further extracted twice with 200 mL of ether, dried (MgSO$_4$), concentrated in vacuo to give yellow oil which was flash chromatographed over silica gel eluting with a 1:4 v:v mixture of ethyl acetate and hexane to give 1.85 g of the title compound as a pale yellow foam: $^1$H-NMR (CDCl$_3$, 200 MHz): ppm 7.40 (m, 6H), 6.85 (d, 1H), 6.2 (s, 1H), 5.05 (s, 2H).

EXAMPLE 5

Preparation of 3-[4-chloro-2-fluoro-5-[(2-propynyl)-oxy]phenyl]-1-(2-propynyl)-6-(trifluoromethyl)-2,4(1H,3H)-pyrimidinedione To a stirred solution of 500 mg (1.50 mmol) of 3-[4-chloro-2-fluoro-5-(hydroxy)phenyl]-6-trifluoromethyl-2,4(1H,3H)-pyrimidinedione in 20 mL of acetonitrile was added 425 mg (3.1 mmol) of potassium carbonate and 0.34 mL (3.10 mmol) of 80% solution of propargyl bromide in toluene. The stirred mixture was then refluxed gently under nitrogen for 2 h. The solution was filtered, washed with ethyl acetate, and concentrated in vacuo. The resulting yellow oil was flash chromatographed over silica gel, eluting with a 1:4 v:v mixture of ethyl acetate and hexane to give 90 mg of the title compound as a pale yellow oil: $^1$H-NMR (CDCl$_3$, 200 MHz): ppm 7.35 (d, 1H), 7.0 (d, 1H), 6.4 (s, 1H), 4.75 (m, 4H), 2.6 (m, 1H), 2.4 (m, 1H). It also gives 150 mg of 3-[4-chloro-2-fluoro-5-[(2-propynyl) oxy]phenyl]-1-6-(trifluoromethyl)-2,4 (1H,3H)-pyrimidinedione as a yellow oil: $^1$H-NMR (DMSO-d$_6$): ppm 7.7 (d, 1 H), 7.4 (d, 1H), 6.4 (s, 1H), 4.8 (d, 2H), 2.5 (m, 1H).

EXAMPLE 6

Preparation of 3-[4-chloro-2-fluoro-5-(hydroxy)phenyl]-6-trifluoromethyl-2,4(1H,3H)-pyrimidinedione A mixture of 4.27 g (10.3 mmol) of 3-[4-chloro-2-fluoro-5-(phenylmethoxy)phenyl]-6-(trifluoromethyl)-2,4(1H,3H)-pyrimidinedione and 420 mg of 10% palladium on charcoal in 70 mL of ethyl acetate was placed in a Paar bottle and was agitated under 45 psi hydrogen over a 16 hour period. It was filtered and washed with ethyl acetate. The filtrate was concentrated in vacuo and the resultant crude product flash chromatographed over silica gel, eluting with a 95:5 v:v mixture of dichloromethane and methanol to give 2.50 g of the title compound as a pale orange solid, m.p.: 68°–72° C.; $^1$H-NMR (DMSO-d$_6$): ppm 7.5 (d, 1H), 7.0 (d, 1H), 6.4 (s, 1H).

EXAMPLE 7

Preparation of 3-[4-chloro-2-fluoro-5-[(2-propynyl)-oxy]phenyl]-6-(dimethylamino)-1-methyl-1,3,5-triazine-2,4(1H,3H)-dione To a solution of 2.80 g (8.90 mmol) of 3-[4-chloro-2-fluoro-5-(hydroxy)phenyl]-6-(dimethylamino)-1-methyl-1,3,5-triazine-2,4(1H,3H)-dione in 50 mL of acetone was added 1.47 g (10.7 mmol) of potassium carbonate and 1.98 mL (17.8 mmol) of an 80% solution of propargyl bromide in toluene. It was then warmed to reflux for 2 h. It was cooled to room temperature and the mixture was filtered and washed with excess ethyl acetate. The crude product was flash chromatographed over silica gel, eluting with a 3:7 v:v mixture of ethyl acetate and hexane to give 3.1 g of the title compound as a pale yellow solid, m.p.: 61°–65° C.; $^1$H-NMR (CDCl$_3$, 200 MHz) ppm 7.0 (d, 1H), 4.75 (m, 2H), 3.45 (s, 3H), 3.1 (s, 6H), 2.6 (m, 1H).

EXAMPLE 8

Preparation of 3-[4-chloro-2-fluoro-5-(hydroxy)phenyl]-6-(dimethylamino)-1-methyl-1,3,5-triazine-2,4(1H,3H)-dione A mixture of 4.62 g (11.4 mmol) of 3-[4-chloro-2-fluoro-5-(phenylmethoxy)phenyl]-6-(dimethylamino)-1-methyl-1,3,5-triazine-2,4(1H,3H)-dione and 460 mg of 10% palladium on charcoal in 50 mL of ethyl acetate was placed in a Paar bottle and was agitated under 45 psi hydrogen over a 14 hour period. It was filtered and washed with ethyl acetate. The filtrate was concentrated in vacuo and the resultant crude product flash chromatographed over silica gel eluting with a 1:1 v:v mixture of ethyl acetate and hexane to give 3.2 g of the title compound as a pale grey solid, m.p.: 247°–249° C. (dec); $^1$H-NMR (DMSO-d$_6$) ppm 7.45 (d, 1H), 6.95 (d, 1H), 3.3 (s, 3H), 3.0 (s, 6H).

EXAMPLE 9

Preparation of 3-[4-chloro-2-fluoro-5-(phenylmethoxy)-phenyl]-6-(dimethylamino)-1-methyl-1,3,5-triazine-2,4(1H,3H)-dione To a solution of 5.05 g (29.2 mmol) of N-ethoxycarbonyl-N,N', N"-trimethylguanidine in 25 mL of toluene was added a solution of 7.72 g (27.8 mmol) of 4-chloro-2-fluoro-5-(phenylmethoxy)phenyl isocyanate in 50 mL of toluene over a period of 30 min while maintaining the temperature between 55° C. and 80° C. It was then stirred at the same temperature for an hour. To a solution of the resulting N-[N-[4-chloro-2-fluoro-5-(phenylmethoxy) phenyl]carbamoyl-N',N'-dimethylamidino]-N-methylcarbamate in toluene was added 3.21 g (71.5 mmol) of dimethylamine in 10 mL of toluene at room temperature. While the temperature was between 25° C. and 40° C., 45 mg (0.834 mmol) of sodium methoxide was added. After 30 min, it was quenched with 100 mL of water. The aqueous layer was extracted with ethyl acetate. The combined organic layers were washed with 0.1N hydrochloric acid, brine, and water, dried (MgSO$_4$) and concentrated in vacuo. The crude product was flash chromatographed over silica gel eluting with a 1:1 v:v mixture of ethyl acetate and hexane to give 5.3 g of the title compound as a brown solid, m.p.: 193°–194° C.; $^1$H-NMR (CDCl$_3$, 200 MHZ) ppm 7.4 (m, 6H), 6.95 (d, 1H), 5.05 (d, 2H), 3.45 (s, 3H), 3.1 (s, 6H).

Using the procedures outlined in Schemes 1–9, and Examples 1–9, the compounds of this invention including the compounds of Tables I–III can readily be prepared by one skilled in the art.

TABLE I

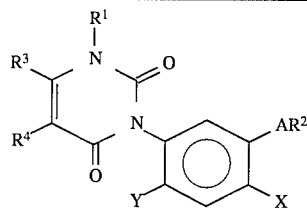

| R¹ | R² | R³ | R⁴ | A | X | Y |
|---|---|---|---|---|---|---|
| CH₃ | H | CF₃ | H | O | Cl | F |
| CH₃ | H | CF₃ | H | S | Cl | F |
| CH₃ | H | CF₃ | H | O | Cl | Cl |
| CH₃ | H | CF₃ | H | S | Cl | Cl |
| CH₃ | H | CF₃ | Br | O | Cl | F |
| CH₃ | H | CF₃ | Br | S | Cl | F |
| CH₃ | H | CF₃ | Br | O | Cl | Cl |
| CH₃ | H | CF₃ | Br | S | Cl | Cl |
| CH₃ | CH₂Ph | CF₃ | H | O | Cl | F |
| CH₃ | CH₂Ph | CF₃ | H | S | Cl | F |
| CH₃ | CH₂Ph | CF₃ | H | O | Cl | Cl |
| CH₃ | CH₂Ph | CF₃ | H | S | Cl | Cl |
| CH₃ | CH₂Ph | CF₃ | Br | O | Cl | F |
| CH₃ | CH₂Ph | CF₃ | Br | S | Cl | F |
| CH₃ | CH₂Ph | CF₃ | Br | O | Cl | Cl |
| CH₃ | CH₂Ph | CF₃ | Br | S | Cl | Cl |
| CH₃ | CH₂C≡CH | CF₃ | H | O | Cl | F |
| CH₃ | CH₂C≡CH | CF₃ | H | S | Cl | F |
| CH₃ | CH₂C≡CH | CF₃ | H | O | Cl | Cl |
| CH₃ | CH₂C≡CH | CF₃ | H | S | Cl | Cl |
| CH₃ | CH₂C≡CH | CF₃ | Br | O | Cl | F |
| CH₃ | CH₂C≡CH | CF₃ | Br | S | Cl | F |
| CH₃ | CH₂C≡CH | CF₃ | Br | O | Cl | Cl |
| CH₃ | CH₂C≡CH | CF₃ | Br | S | Cl | Cl |
| CH₃ | iPr | CF₃ | H | O | Cl | F |
| CH₃ | iPr | CF₃ | H | S | Cl | F |
| CH₃ | iPr | CF₃ | H | O | Cl | Cl |
| CH₃ | iPr | CF₃ | H | S | Cl | Cl |
| CH₃ | iPr | CF₃ | Br | O | Cl | F |
| CH₃ | iPr | CF₃ | Br | S | Cl | F |
| CH₃ | iPr | CF₃ | Br | O | Cl | Cl |
| CH₃ | iPr | CF₃ | Br | S | Cl | Cl |
| CH₃ | CH₂C=CH₂ | CF₃ | H | O | Cl | F |
| CH₃ | CH₂C=CH₂ | CF₃ | H | S | Cl | F |
| CH₃ | CH₂C=CH₂ | CF₃ | H | O | Cl | Cl |
| CH₃ | CH₂C=CH₂ | CF₃ | H | S | Cl | Cl |
| CH₃ | CH₂C=CH₂ | CF₃ | Br | O | Cl | F |
| CH₃ | CH₂C=CH₂ | CF₃ | Br | S | Cl | F |
| CH₃ | CH₂C=CH₂ | CF₃ | Br | O | Cl | Cl |
| CH₃ | CH₂C=CH₂ | CF₃ | Br | S | Cl | Cl |
| CF₃ | H | CF₃ | H | O | Cl | F |
| CF₃ | H | CF₃ | H | S | Cl | F |
| CF₃ | H | CF₃ | H | O | Cl | Cl |
| CF₃ | H | CF₃ | H | S | Cl | Cl |
| CF₃ | H | CF₃ | Br | O | Cl | F |
| CF₃ | H | CF₃ | Br | S | Cl | F |
| CF₃ | H | CF₃ | Br | O | Cl | Cl |
| CF₃ | H | CF₃ | Br | S | Cl | Cl |
| CF₃ | CH₂Ph | CF₃ | H | O | Cl | F |
| CF₃ | CH₂Ph | CF₃ | H | S | Cl | F |
| CF₃ | CH₂Ph | CF₃ | H | O | Cl | Cl |
| CF₃ | CH₂Ph | CF₃ | H | S | Cl | Cl |
| CF₃ | CH₂Ph | CF₃ | Br | O | Cl | F |
| CF₃ | CH₂Ph | CF₃ | Br | S | Cl | F |
| CF₃ | CH₂Ph | CF₃ | Br | O | Cl | Cl |
| CF₃ | CH₂Ph | CF₃ | Br | S | Cl | Cl |
| CF₃ | CH₂C≡CH | CF₃ | H | O | Cl | F |
| CF₃ | CH₂C≡CH | CF₃ | H | S | Cl | F |
| CF₃ | CH₂C≡CH | CF₃ | H | O | Cl | Cl |
| CF₃ | CH₂C≡CH | CF₃ | H | S | Cl | Cl |
| CF₃ | CH₂C≡CH | CF₃ | Br | O | Cl | F |
| CF₃ | CH₂C≡CH | CF₃ | Br | S | Cl | F |
| CF₃ | CH₂C≡CH | CF₃ | Br | O | Cl | Cl |
| CF₃ | CH₂C≡CH | CF₃ | Br | S | Cl | Cl |
| CF₃ | iPr | CF₃ | H | O | Cl | F |
| CF₃ | iPr | CF₃ | H | S | Cl | F |
| CF₃ | iPr | CF₃ | H | O | Cl | Cl |
| CF₃ | iPr | CF₃ | H | S | Cl | Cl |
| CF₃ | iPr | CF₃ | Br | O | Cl | F |
| CF₃ | iPr | CF₃ | Br | S | Cl | F |
| CF₃ | iPr | CF₃ | Br | O | Cl | Cl |
| CF₃ | iPr | CF₃ | Br | S | Cl | Cl |
| CF₃ | CH₂C=CH₂ | CF₃ | H | O | Cl | F |
| CF₃ | CH₂C=CH₂ | CF₃ | H | S | Cl | F |
| CF₃ | CH₂C=CH₂ | CF₃ | H | O | Cl | Cl |
| CF₃ | CH₂C=CH₂ | CF₃ | H | S | Cl | Cl |
| CF₃ | CH₂C=CH₂ | CF₃ | Br | O | Cl | F |
| CF₃ | CH₂C=CH₂ | CF₃ | Br | S | Cl | F |
| CF₃ | CH₂C=CH₂ | CF₃ | Br | O | Cl | Cl |
| CF₃ | CH₂C=CH₂ | CF₃ | Br | S | Cl | Cl |
| CH₂C≡CH | H | CF₃ | H | O | Cl | F |
| CH₂C≡CH | H | CF₃ | H | S | Cl | F |
| CH₂C≡CH | H | CF₃ | H | O | Cl | Cl |
| CH₂C≡CH | H | CF₃ | H | S | Cl | Cl |
| CH₂C≡CH | H | CF₃ | Br | O | Cl | F |
| CH₂C≡CH | H | CF₃ | Br | S | Cl | F |
| CH₂C≡CH | H | CF₃ | Br | O | Cl | Cl |

TABLE I-continued

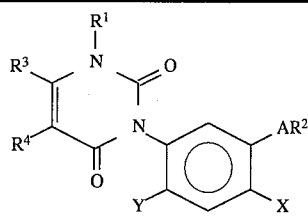

| R¹ | R² | R³ | R⁴ | A | X | Y |
|---|---|---|---|---|---|---|
| CH₂C≡CH | H | CF₃ | Br | S | Cl | Cl |
| CH₂C≡CH | CH₂Ph | CF₃ | H | O | Cl | F |
| CH₂C≡CH | CH₂Ph | CF₃ | H | S | Cl | F |
| CH₂C≡CH | CH₂Ph | CF₃ | H | O | Cl | Cl |
| CH₂C≡CH | CH₂Ph | CF₃ | H | S | Cl | Cl |
| CH₂C≡CH | CH₂Ph | CF₃ | Br | O | Cl | F |
| CH₂C≡CH | CH₂Ph | CF₃ | Br | S | Cl | F |
| CH₂C≡CH | CH₂Ph | CF₃ | Br | O | Cl | Cl |
| CH₂C≡CH | CH₂Ph | CF₃ | Br | S | Cl | Cl |
| CH₂C≡CH | CH₂C≡CH | CF₃ | H | O | Cl | F |
| CH₂C≡CH | CH₂C≡CH | CF₃ | H | S | Cl | F |
| CH₂C≡CH | CH₂C≡CH | CF₃ | H | O | Cl | Cl |
| CH₂C≡CH | CH₂C≡CH | CF₃ | H | S | Cl | Cl |
| CH₂C≡CH | CH₂C≡CH | CF₃ | Br | O | Cl | F |
| CH₂C≡CH | CH₂C≡CH | CF₃ | Br | S | Cl | F |
| CH₂C≡CH | CH₂C≡CH | CF₃ | Br | O | Cl | Cl |
| CH₂C≡CH | CH₂C≡CH | CF₃ | Br | S | Cl | Cl |
| CH₂C≡CH | iPr | CF₃ | H | O | Cl | F |
| CH₂C≡CH | iPr | CF₃ | H | S | Cl | F |
| CH₂C≡CH | iPr | CF₃ | H | O | Cl | Cl |
| CH₂C≡CH | iPr | CF₃ | H | S | Cl | Cl |
| CH₂C≡CH | iPr | CF₃ | Br | O | Cl | F |
| CH₂C≡CH | iPr | CF₃ | Br | S | Cl | F |
| CH₂C≡CH | iPr | CF₃ | Br | O | Cl | Cl |
| CH₂C≡CH | iPr | CF₃ | Br | S | Cl | Cl |
| CH₂C≡CH | CH₂C=CH₂ | CF₃ | H | O | Cl | F |
| CH₂C≡CH | CH₂C=CH₂ | CF₃ | H | S | Cl | F |
| CH₂C≡CH | CH₂C=CH₂ | CF₃ | H | O | Cl | Cl |
| CH₂C≡CH | CH₂C=CH₂ | CF₃ | H | S | Cl | Cl |
| CH₂C≡CH | CH₂C=CH₂ | CF₃ | Br | O | Cl | F |
| CH₂C≡CH | CH₂C=CH₂ | CF₃ | Br | S | Cl | F |
| CH₂C≡CH | CH₂C=CH₂ | CF₃ | Br | O | Cl | Cl |
| CH₂C≡CH | CH₂C=CH₂ | CF₃ | Br | S | Cl | Cl |
| CH₂C≡CF | CH₂C≡CH | CF₃ | H | O | Cl | Cl |
| CH₂C≡CF | CH₂C≡CH | CF₃ | H | S | Cl | F |
| CH₂C≡CF | CH₂C≡CH | CF₃ | H | S | Cl | Cl |
| CH₂C≡CF | CH₂Ph | CF₃ | H | O | Cl | F |
| CH₂C≡CF | CH₂Ph | CF₃ | H | O | Cl | Cl |
| CH₂C≡CF | CH₂Ph | CF₃ | H | S | Cl | F |
| CH₂C≡CF | CH₂Ph | CF₃ | H | S | Cl | Cl |
| CH₂C≡CF | H | CF₃ | H | O | Cl | Cl |
| CH₂C≡CF | H | CF₃ | H | S | Cl | F |
| CH₂C≡CF | H | CF₃ | H | S | Cl | Cl |
| CH₂C≡CF | H | CF₃ | H | O | Cl | F |
| CH₂C≡CF | iPr | CF₃ | H | O | Cl | Cl |
| CH₂C≡CF | iPr | CF₃ | H | S | Cl | F |

TABLE I-continued

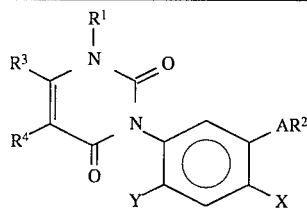

| R¹ | R² | R³ | R⁴ | A | X | Y |
|---|---|---|---|---|---|---|
| CH₂C≡CF | iPr | CF₃ | H | S | Cl | Cl |
| CH₂C≡CF | iPr | CF₃ | H | O | Cl | F |
| CH₂CH=CH₂ | CH₂C≡CH | CF₃ | H | O | Cl | F |
| CH₂CH=CH₂ | CH₂C≡CH | CF₃ | H | O | Cl | Cl |
| CH₂CH=CH₂ | CH₂Ph | CF₃ | H | O | Cl | F |
| CH₂CH=CH₂ | CH₂Ph | CF₃ | H | O | Cl | Cl |
| CH₂CH=CH₂ | CH₂CH=CH₂ | CF₃ | H | O | Cl | F |
| CH₂CH=CH₂ | CH₂CH=CH₂ | CF₃ | H | O | Cl | Cl |
| CHF₂ | H | N(CH₃)₂ | H | O | Cl | F |
| CHF₂ | H | N(CH₃)₂ | H | S | Cl | F |
| CHF₂ | H | N(CH₃)₂ | H | O | Cl | Cl |
| CHF₂ | H | N(CH₃)₂ | H | S | Cl | Cl |
| CHF₂ | H | N(CH₃)₂ | Br | O | Cl | F |
| CHF₂ | H | N(CH₃)₂ | Br | S | Cl | F |
| CHF₂ | H | N(CH₃)₂ | Br | O | Cl | Cl |
| CHF₂ | H | N(CH₃)₂ | Br | S | Cl | Cl |
| CHF₂ | CH₂Ph | N(CH₃)₂ | H | O | Cl | F |
| CHF₂ | CH₂Ph | N(CH₃)₂ | H | S | Cl | F |
| CHF₂ | CH₂Ph | N(CH₃)₂ | H | O | Cl | Cl |
| CHF₂ | CH₂Ph | N(CH₃)₂ | H | S | Cl | Cl |
| CHF₂ | CH₂Ph | N(CH₃)₂ | Br | O | Cl | F |
| CHF₂ | CH₂Ph | N(CH₃)₂ | Br | S | Cl | F |
| CHF₂ | CH₂Ph | N(CH₃)₂ | Br | O | Cl | Cl |
| CHF₂ | CH₂Ph | N(CH₃)₂ | Br | S | Cl | Cl |
| CHF₂ | CH₂C≡CH | N(CH₃)₂ | H | O | Cl | F |
| CHF₂ | CH₂C≡CH | N(CH₃)₂ | H | S | Cl | F |
| CHF₂ | CH₂C≡CH | N(CH₃)₂ | H | O | Cl | Cl |
| CHF₂ | CH₂C≡CH | N(CH₃)₂ | H | S | Cl | Cl |
| CHF₂ | CH₂C≡CH | N(CH₃)₂ | Br | O | Cl | F |
| CHF₂ | CH₂C≡CH | N(CH₃)₂ | Br | S | Cl | F |
| CHF₂ | CH₂C≡CH | N(CH₃)₂ | Br | O | Cl | Cl |
| CHF₂ | CH₂C≡CH | N(CH₃)₂ | Br | S | Cl | Cl |
| CHF₂ | iPr | N(CH₃)₂ | H | O | Cl | F |
| CHF₂ | iPr | N(CH₃)₂ | H | S | Cl | F |
| CHF₂ | iPr | N(CH₃)₂ | H | O | Cl | Cl |
| CHF₂ | iPr | N(CH₃)₂ | H | S | Cl | Cl |
| CHF₂ | iPr | N(CH₃)₂ | Br | O | Cl | F |
| CHF₂ | iPr | N(CH₃)₂ | Br | S | Cl | F |
| CHF₂ | iPr | N(CH₃)₂ | Br | O | Cl | Cl |
| CHF₂ | iPr | N(CH₃)₂ | Br | S | Cl | Cl |
| CHF₂ | CH₂C=CH₂ | N(CH₃)₂ | H | O | Cl | F |
| CHF₂ | CH₂C=CH₂ | N(CH₃)₂ | H | S | Cl | F |
| CHF₂ | CH₂C=CH₂ | N(CH₃)₂ | H | O | Cl | Cl |

TABLE I-continued

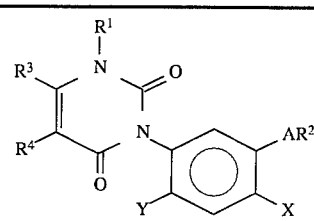

| R¹ | R² | R³ | R⁴ | A | X | Y |
|---|---|---|---|---|---|---|
| CHF₂ | CH₂C=CH₂ | N(CH₃)₂ | H | S | Cl | Cl |
| CHF₂ | CH₂C=CH₂ | N(CH₃)₂ | Br | O | Cl | F |
| CHF₂ | CH₂C=CH₂ | N(CH₃)₂ | Br | S | Cl | F |
| CHF₂ | CH₂C=CH₂ | N(CH₃)₂ | Br | O | Cl | Cl |
| CHF₂ | CH₂C=CH₂ | N(CH₃)₂ | Br | S | Cl | Cl |
| CH₃ | H | N(CH₃)₂ | H | O | Cl | F |
| CH₃ | H | N(CH₃)₂ | H | S | Cl | F |
| CH₃ | H | N(CH₃)₂ | H | O | Cl | Cl |
| CH₃ | H | N(CH₃)₂ | H | S | Cl | Cl |
| CH₃ | H | N(CH₃)₂ | Br | O | Cl | F |
| CH₃ | H | N(CH₃)₂ | Br | S | Cl | F |
| CH₃ | H | N(CH₃)₂ | Br | O | Cl | Cl |
| CH₃ | H | N(CH₃)₂ | Br | S | Cl | Cl |
| CH₃ | CH₂Ph | N(CH₃)₂ | H | O | Cl | F |
| CH₃ | CH₂Ph | N(CH₃)₂ | H | S | Cl | F |
| CH₃ | CH₂Ph | N(CH₃)₂ | H | O | Cl | Cl |
| CH₃ | CH₂Ph | N(CH₃)₂ | H | S | Cl | Cl |
| CH₃ | CH₂Ph | N(CH₃)₂ | Br | O | Cl | F |
| CH₃ | CH₂Ph | N(CH₃)₂ | Br | S | Cl | F |
| CH₃ | CH₂Ph | N(CH₃)₂ | Br | O | Cl | Cl |
| CH₃ | CH₂Ph | N(CH₃)₂ | Br | S | Cl | Cl |
| CH₃ | CH₂C≡CH | N CH₃)₂ | H | O | Cl | F |
| CH₃ | CH₂C≡CH | N(CH₃)₂ | H | S | Cl | F |
| CH₃ | CH₂C≡CH | N(CH₃)₂ | H | O | Cl | Cl |
| CH₃ | CH₂C≡CH | N(CH₃)₂ | H | S | Cl | Cl |
| CH₃ | CH₂C≡CH | N(CH₃)₂ | Br | O | Cl | F |
| CH₃ | CH₂C≡CH | N(CH₃)₂ | Br | S | Cl | F |
| CH₃ | CH₂C≡CH | N(CH₃)₂ | Br | O | Cl | Cl |
| CH₃ | CH₂C≡CH | N(CH₃)₂ | Br | S | Cl | Cl |
| CH₃ | iPr | N(CH₃)₂ | H | O | Cl | F |
| CH₃ | iPr | N(CH₃)₂ | H | S | Cl | F |
| CH₃ | iPr | N(CH₃)₂ | H | O | Cl | Cl |
| CH₃ | iPr | N(CH₃)₂ | H | S | Cl | Cl |
| CH₃ | iPr | N(CH₃)₂ | Br | O | Cl | F |
| CH₃ | iPr | N(CH₃)₂ | Br | S | Cl | F |
| CH₃ | iPr | N(CH₃)₂ | Br | O | Cl | Cl |
| CH₃ | iPr | N(CH₃)₂ | Br | S | Cl | Cl |
| CH₃ | CH₂C=CH₂ | N(CH₃)₂ | H | O | Cl | F |
| CH₃ | CH₂C=CH₂ | N(CH₃)₂ | H | S | Cl | F |
| CH₃ | CH₂C=CH₂ | N(CH₃)₂ | H | O | Cl | Cl |
| CH₃ | CH₂C=CH₂ | N(CH₃)₂ | H | S | Cl | Cl |
| CH₃ | CH₂C=CH₂ | N(CH₃)₂ | Br | O | Cl | F |
| CH₃ | CH₂C=CH₂ | N(CH₃)₂ | Br | S | Cl | F |
| CH₃ | CH₂C=CH₂ | N(CH₃)₂ | Br | O | Cl | Cl |
| CH₃ | CH₂C=CH₂ | N(CH₃)₂ | Br | S | Cl | Cl |
| CH₃ | CH₂Ph | —(CH₂)₃— | | O | Cl | F |
| CH₃ | CH₂Ph | —(CH₂)₃— | | S | Cl | F |
| CH₃ | CH₂Ph | —(CH₂)₃— | | O | Cl | Cl |
| CH₃ | CH₂Ph | —(CH₂)₃— | | S | Cl | Cl |

TABLE I-continued

![Structure with R¹, R³, R⁴, AR², X, Y substituents on pyrimidinone-aryl system]

| R¹ | R² | R³ | R⁴ | A | X | Y |
|---|---|---|---|---|---|---|
| CH₃ | CH₂C≡CH | —(CH₂)₃— | | O | Cl | F |
| CH₃ | CH₂C≡CH | —(CH₂)₃— | | S | Cl | F |
| CH₃ | CH₂C≡CH | —(CH₂)₃— | | O | Cl | Cl |
| CH₃ | CH₂C≡CH | —(CH₂)₃— | | S | Cl | Cl |
| CH₃ | iPr | —(CH₂)₃— | | O | Cl | F |
| CH₃ | iPr | —(CH₂)₃— | | S | Cl | F |
| CH₃ | iPr | —(CH₂)₃— | | O | Cl | Cl |
| CH₃ | iPr | —(CH₂)₃— | | S | Cl | Cl |
| CH₃ | CH₂Ph | —(CH₂)₄— | | O | Cl | F |
| CH₃ | CH₂Ph | —(CH₂)₄— | | S | Cl | F |
| CH₃ | CH₂Ph | —(CH₂)₄— | | O | Cl | Cl |
| CH₃ | CH₂Ph | —(CH₂)₄— | | S | Cl | Cl |
| CH₃ | CH₂C≡CH | —(CH₂)₄— | | O | Cl | F |
| CH₃ | CH₂C≡CH | —(CH₂)₄— | | S | Cl | F |
| CH₃ | CH₂C≡CH | —(CH₂)₄— | | O | Cl | Cl |
| CH₃ | CH₂C≡CH | —(CH₂)₄— | | S | Cl | Cl |
| CH₃ | iPr | —(CH₂)₄— | | O | Cl | F |
| CH₃ | iPr | —(CH₂)₄— | | S | Cl | F |
| CH₃ | iPr | —(CH₂)₄— | | O | Cl | Cl |
| CH₃ | iPr | —(CH₂)₄— | | S | Cl | Cl |
| CN | CH₂C≡CH | CF₃ | H | O | Cl | F |
| CN | CH₂C≡CH | CF₃ | H | S | Cl | F |
| CN | CH₂C≡CH | N(CH₃)₂ | H | O | Cl | Cl |
| CN | CH₂C≡CH | N(CH₃)₂ | Br | S | Cl | Cl |
| COCH₃ | CH₂C≡CH | CF₃ | H | O | Cl | F |
| COCH₃ | CH₂C≡CH | CF₃ | H | S | Cl | F |
| COCH₃ | CH₂C≡CH | N(CH₃)₂ | H | O | Cl | Cl |
| COCH₃ | CH₂C≡CH | N(CH₃)₂ | Br | S | Cl | Cl |
| COCH₃ | iPr | N(CH₃)₂ | H | S | Cl | F |
| COCH₃ | iPr | N(CH₃)₂ | H | O | Cl | F |
| COCH₃ | iPr | N(CH₃)₂ | H | O | Cl | Cl |
| COCH₃ | iPr | N(CH₃)₂ | Br | O | Cl | F |
| COCF₃ | CH₂C≡CH | CF₃ | H | S | Cl | F |
| COCF₃ | CH₂C≡CH | CF₃ | H | O | Cl | Cl |
| COCF₃ | CH₂C≡CH | CF₃ | H | O | Cl | F |
| COCF₃ | iPr | N(CH₃)₂ | H | S | Cl | F |
| COCF₃ | iPr | N(CH₃)₂ | H | O | Cl | Cl |
| COCF₃ | iPr | N(CH₃)₂ | H | O | Cl | F |
| OCH₃ | CH₂C≡CH | CF₃ | H | O | Cl | F |
| OCH₃ | CH₂C≡CH | CF₃ | H | S | Cl | F |
| OCH₃ | CH₂C≡CH | N(CH₃)₂ | H | O | Cl | Cl |
| OCH₃ | CH₂C≡CH | N(CH₃)₂ | Br | S | Cl | Cl |
| CF₂H | CH₂C≡CH | CF₃ | H | O | Cl | F |
| CF₂H | CH₂C≡CH | CF₃ | H | S | Cl | F |
| CF₂H | CH₂C≡CH | N(CH₃)₂ | H | O | Cl | Cl |
| CF₂H | CH₂C≡CH | N(CH₃)₂ | Br | S | Cl | Cl |
| CF₂H | iPr | N(CH₃)₂ | H | S | Cl | F |
| CF₂H | iPr | N(CH₃)₂ | H | O | Cl | F |
| CF₂H | iPr | N(CH₃)₂ | H | O | Cl | Cl |
| CF₂H | iPr | N(CH₃)₂ | Br | O | Cl | F |
| n-Bu | CH₂C≡CH | CF₃ | H | S | Cl | F |
| n-Bu | CH₂C≡CH | CF₃ | H | O | Cl | Cl |
| n-Bu | CH₂C≡CH | CF₃ | H | O | Cl | F |
| n-Bu | iPr | N(CH₃)₂ | H | S | Cl | F |
| n-Bu | iPr | N(CH₃)₂ | H | O | Cl | Cl |
| n-Bu | iPr | N(CH₃)₂ | H | O | Cl | F |
| CHMeC≡CH | CH₂C≡CH | CF₃ | H | S | Cl | F |
| CHMeC≡CH | CH₂C≡CH | CF₃ | H | O | Cl | Cl |
| CHMeC≡CH | CH₂C≡CH | CF₃ | H | O | Cl | F |
| CHMeC≡CH | CH₂C≡CH | N(CH₃)₂ | H | S | Cl | F |
| CHMeC≡CH | CH₂C≡CH | N(CH₃)₂ | H | O | Cl | Cl |
| CHMeC≡CH | CH₂C≡CH | N(CH₃)₂ | H | O | Cl | F |

TABLE I-continued

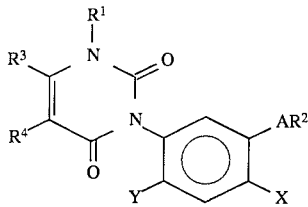

| R¹ | R² | R³ | R⁴ | A | X | Y |
|---|---|---|---|---|---|---|
| CHMeC≡CH | iPr | CF₃ | H | S | Cl | F |
| CHMeC≡CH | iPr | CF₃ | H | O | Cl | Cl |
| CHMeC≡CH | iPr | CF₃ | H | O | Cl | F |
| CHMeC≡CH | iPr | N(CH₃)₂ | H | S | Cl | F |
| CHMeC≡CH | iPr | N(CH₃)₂ | H | O | Cl | Cl |
| CHMeC≡CH | iPr | N(CH₃)₂ | H | O | Cl | F |
| CH₂CMe=CH₂ | CH₂C≡CH | N(CH₃)₂ | H | S | Cl | F |
| CH₂CMe=CH₂ | CH₂C≡CH | N(CH₃)₂ | H | O | Cl | Cl |
| CH₂CMe=CH₂ | CH₂C≡CH | N(CH₃)₂ | H | S | Cl | F |
| CH₂CMe=CH₂ | CH₂C≡CH | CF₃ | H | O | Cl | Cl |
| CH₂CMe=CH₂ | CH₂C≡CH | CF₃ | H | S | Cl | F |
| CH₂CMe=CH₂ | CH₂C≡CH | CF₃ | H | O | Cl | Cl |
| CH₂CMe=CH₂ | iPr | N(CH₃)₂ | H | S | Cl | F |
| CH₂CMe=CH₂ | iPr | N(CH₃)₂ | H | O | Cl | Cl |
| CH₂CMe=CH₂ | iPr | N(CH₃)₂ | H | S | Cl | F |
| CH₂CMe=CH₂ | iPr | CF₃ | H | O | Cl | Cl |
| CH₂CMe=CH₂ | iPr | CF₃ | H | S | Cl | F |
| CH₂CMe=CH₂ | iPr | CF₃ | H | O | Cl | Cl |
| CH₂CMe=CH₂ | CH₂C≡CH | N(CH₃)₂ | H | S | Cl | F |
| CH₂CMe=CH₂ | CH₂C≡CH | N(CH₃)₂ | H | O | Cl | Cl |
| CH₂CMe=CH₂ | CH₂C≡CH | N(CH₃)₂ | H | S | Cl | F |
| CH₂CMe=CH₂ | CH₂C≡CH | CF₃ | H | O | Cl | Cl |
| CH₂CMe=CH₂ | CH₂C≡CH | CF₃ | H | S | Cl | F |
| CH₂CMe=CH₂ | CH₂C≡CH | CF₃ | H | O | Cl | Cl |
| iPr | iPr | N(CH₃)₂ | H | S | Cl | F |
| iPr | iPr | N(CH₃)₂ | H | O | Cl | Cl |
| iPr | iPr | N(CH₃)₂ | H | S | Cl | F |
| iPr | iPr | CF₃ | H | O | Cl | Cl |
| iPr | iPr | CF₃ | H | S | Cl | F |
| iPr | iPr | CF₃ | H | O | Cl | Cl |

TABLE II

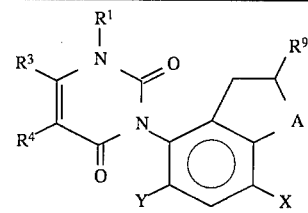

R⁹ = CH₃ unless otherwise noted

| R¹ | R³ | R⁴ | A | X | Y | R⁹ |
|---|---|---|---|---|---|---|
| CH₃ | CF₃ | H | O | Cl | F | |
| CH₃ | CF₃ | H | S | Cl | F | |
| CH₃ | CF₃ | H | O | Cl | Cl | |
| CH₃ | CF₃ | H | S | Cl | Cl | |
| CH₃ | N(CH₃)₂ | H | O | Cl | F | |
| CH₃ | N(CH₃)₂ | H | S | Cl | F | |
| CH₃ | N(CH₃)₂ | H | O | Cl | Cl | |
| CH₃ | N(CH₃)₂ | H | S | Cl | Cl | |
| CH₃ | CF₃ | Br | O | Cl | F | |
| CH₃ | CF₃ | Br | S | Cl | F | |
| CH₃ | CF₃ | Br | O | Cl | Cl | |
| CH₃ | CF₃ | Br | S | Cl | Cl | |
| CH₃ | N(CH₃)₂ | Br | O | Cl | F | |
| CH₃ | N(CH₃)₂ | Br | S | Cl | F | |
| CH₃ | N(CH₃)₂ | Br | O | Cl | Cl | |
| CH₃ | N(CH₃)₂ | Br | S | Cl | Cl | |
| CH₃ | —(CH₂)₃— | | O | Cl | F | |
| CH₃ | —(CH₂)₃— | | O | Cl | Cl | |
| CH₃ | —(CH₂)₃— | | S | Cl | F | |
| CH₃ | —(CH₂)₃— | | S | Cl | Cl | |
| CH₃ | —(CH₂)₄— | | O | Cl | F | |
| CH₃ | —(CH₂)₄— | | S | Cl | F | |
| CH₃ | —(CH₂)₄— | | S | Cl | F | |
| CF₃ | CF₃ | H | O | Cl | F | |
| CF₃ | CF₃ | H | S | Cl | F | |
| CF₃ | CF₃ | H | O | Cl | Cl | |
| CF₃ | CF₃ | H | S | Cl | Cl | |
| CF₃ | N(CH₃)₂ | H | O | Cl | F | |
| CF₃ | N(CH₃)₂ | H | S | Cl | F | |
| CF₃ | N(CH₃)₂ | H | O | Cl | Cl | |
| CF₃ | N(CH₃)₂ | H | S | Cl | Cl | |
| CF₃ | CF₃ | Br | O | Cl | F | |
| CF₃ | CF₃ | Br | S | Cl | F | |
| CF₃ | CF₃ | Br | O | Cl | Cl | |
| CF₃ | CF₃ | Br | S | Cl | Cl | |
| CF₃ | N(CH₃)₂ | Br | O | Cl | F | |
| CF₃ | N(CH₃)₂ | Br | S | Cl | F | |
| CF₃ | N(CH₃)₂ | Br | O | Cl | Cl | |
| CF₃ | N(CH₃)₂ | Br | S | Cl | Cl | |
| CF₃ | —(CH₂)₃— | | O | Cl | F | |
| CF₃ | —(CH₂)₃— | | O | Cl | Cl | |
| CF₃ | —(CH₂)₃— | | S | Cl | F | |
| CF₃ | —(CH₂)₃— | | S | Cl | Cl | |
| CF₃ | —(CH₂)₄— | | O | Cl | F | |
| CF₃ | —(CH₂)₄— | | O | Cl | F | |
| CF₃ | —(CH₂)₄— | | S | Cl | F | |
| CF₃ | —(CH₂)₄— | | S | Cl | F | |
| CH₂C=CH₂ | CF₃ | H | O | Cl | F | |
| CH₂C=CH₂ | CF₃ | H | S | Cl | F | |
| CH₂C=CH₂ | CF₃ | H | O | Cl | Cl | |
| CH₂C=CH₂ | CF₃ | H | O | Cl | F | |
| CH₂C=CH₂ | CHF₂ | H | O | Cl | F | |
| CH₂C=CH₂ | CHF₂ | H | O | Cl | Cl | |
| CH₂C=CH₂ | CHF₂ | H | S | Cl | F | |
| CH₂C=CH₂ | N(CH₃)₂ | H | O | Cl | F | |
| CH₂C=CH₂ | N(CH₃)₂ | H | S | Cl | F | |
| CH₂C=CH₂ | N(CH₃)₂ | H | O | Cl | Cl | |
| CH₂C=CH₂ | N(CH₃)₂ | H | S | Cl | Cl | |
| CH₂C=CH₂ | CF₃ | Br | O | Cl | F | |
| CH₂C=CH₂ | CF₃ | Br | S | Cl | F | |
| CH₂C=CH₂ | CF₃ | Br | O | Cl | Cl | |
| CH₂C=CH₂ | CF₃ | Br | S | Cl | Cl | |
| CH₂C=CH₂ | N(CH₃)₂ | Br | O | Cl | F | |
| CH₂C=CH₂ | N(CH₃)₂ | Br | S | Cl | F | |

TABLE II-continued

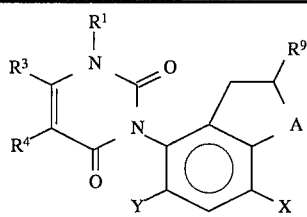

$R^9 = CH_3$ unless otherwise noted

| $R^1$ | $R^3$ | $R^4$ | A | X | Y | $R^9$ |
|---|---|---|---|---|---|---|
| $CH_2C=CH_2$ | $N(CH_3)_2$ | Br | O | Cl | Cl | |
| $CH_2C=CH_2$ | $N(CH_3)_2$ | Br | S | Cl | Cl | |
| $CH_2C=CH_2$ | $-(CH_2)_3-$ | | O | Cl | F | |
| $CH_2C=CH_2$ | $-(CH_2)_3-$ | | O | Cl | Cl | |
| $CH_2C=CH_2$ | $-(CH_2)_3-$ | | S | Cl | F | |
| $CH_2C=CH_2$ | $-(CH_2)_3-$ | | S | Cl | Cl | |
| $CH_2C=CH_2$ | $-(CH_2)_4-$ | | O | Cl | F | |
| $CH_2C=CH_2$ | $-(CH_2)_4-$ | | O | Cl | F | |
| $CH_2C=CH_2$ | $-(CH_2)_4-$ | | S | Cl | F | |
| $CH_2C=CH_2$ | $-(CH_2)_4-$ | | S | Cl | F | |
| $CH_2C\equiv CH$ | $CF_3$ | H | O | Cl | F | |
| $CH_2C\equiv CH$ | $CF_3$ | H | S | Cl | F | |
| $CH_2C\equiv CH$ | $CF_3$ | H | O | Cl | Cl | |
| $CH_2C\equiv CH$ | $CF_3$ | H | O | Cl | F | |
| $CH_2C\equiv CH$ | $CHF_2$ | H | O | Cl | F | |
| $CH_2C\equiv CH$ | $CHF_2$ | H | O | Cl | Cl | |
| $CH_2C\equiv CH$ | $CHF_2$ | H | S | Cl | F | |
| $CH_2C\equiv CH$ | $N(CH_3)_2$ | H | O | Cl | F | |
| $CH_2C\equiv CH$ | $N(CH_3)_2$ | H | S | Cl | F | |
| $CH_2C\equiv CH$ | $N(CH_3)_2$ | H | O | Cl | Cl | |
| $CH_2C\equiv CH$ | $N(CH_3)_2$ | H | S | Cl | Cl | |
| $CH_2C\equiv CH$ | $CF_3$ | Br | O | Cl | F | |
| $CH_2C\equiv CH$ | $CF_3$ | Br | S | Cl | F | |
| $CH_2C\equiv CH$ | $CF_3$ | Br | O | Cl | Cl | |
| $CH_2C\equiv CH$ | $CF_3$ | Br | S | Cl | Cl | |
| $CH_2C\equiv CH$ | $N(CH_3)_2$ | Br | O | Cl | F | |
| $CH_2C\equiv CH$ | $N(CH_3)_2$ | Br | S | Cl | F | |
| $CH_2C\equiv CH$ | $N(CH_3)_2$ | Br | O | Cl | Cl | |
| $CH_2C\equiv CH$ | $N(CH_3)_2$ | Br | S | Cl | Cl | |

TABLE II-continued

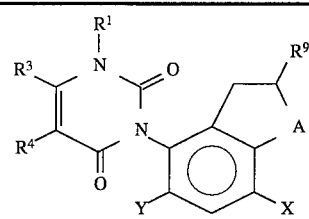

$R^9 = CH_3$ unless otherwise noted

| $R^1$ | $R^3$ | $R^4$ | A | X | Y | $R^9$ |
|---|---|---|---|---|---|---|
| $CH_2C\equiv CH$ | $-(CH_2)_3-$ | | O | Cl | F | |
| $CH_2C\equiv CH$ | $-(CH_2)_3-$ | | O | Cl | Cl | |
| $CH_2C\equiv CH$ | $-(CH_2)_3-$ | | S | Cl | F | |
| $CH_2C\equiv CH$ | $-(CH_2)_3-$ | | S | Cl | Cl | |
| $CH_2C\equiv CH$ | $-(CH_2)_4-$ | | O | Cl | F | |
| $CH_2C\equiv CH$ | $-(CH_2)_4-$ | | O | Cl | F | |
| $CH_2C\equiv CH$ | $-(CH_2)_4-$ | | S | Cl | F | |
| $CH_2C\equiv CH$ | $-(CH_2)_4-$ | | S | Cl | F | |
| $CH_2C\equiv CH$ | $CF_3$ | F | O | Cl | F | |
| $CH_2C\equiv CH$ | $CF_3$ | F | O | Cl | Cl | |
| n-Bu | $CF_3$ | H | O | Cl | F | |
| n-Bu | $CF_3$ | H | S | Cl | F | |
| $COCH_3$ | $CF_3$ | H | O | Cl | F | |
| $COCH_3$ | $CF_3$ | H | O | Cl | Cl | |
| CN | $CF_3$ | H | O | Cl | F | |
| CN | $CF_3$ | H | O | Cl | Cl | |
| $CHF_2$ | $CF_3$ | H | O | Cl | F | |
| $CHF_2$ | $CF_3$ | H | O | Cl | Cl | |
| $CH_3$ | $CHF_2$ | Br | O | Cl | F | |
| $CH_3$ | $CHF_2$ | Br | S | Cl | F | |
| $CH_3$ | $CF_3$ | F | O | Cl | F | |
| $CH_3$ | $CF_3$ | F | S | Cl | F | |
| $CH_3$ | $CHF_2$ | F | O | Cl | F | |
| $CH_3$ | $CHF_2$ | F | S | Cl | F | |
| $CH_3$ | $CH_2F$ | F | O | Cl | F | |
| $CH_3$ | $CH_2F$ | F | S | Cl | F | |
| $CH_3$ | $CF_3$ | Cl | O | Cl | F | |
| $CH_3$ | $CF_3$ | Cl | S | Cl | F | |
| $CH_3$ | $CF_3$ | Cl | O | Cl | F | |
| $CH_3$ | $CF_3$ | Cl | S | Cl | F | |
| $CH_3$ | $CF_3$ | H | O | Cl | F | $CH_2CH_3$ |
| $CH_3$ | $CF_3$ | H | S | Cl | F | $CH_2CH_3$ |
| $CH_3$ | $CF_3$ | H | O | Cl | Cl | $CH_2CH_3$ |
| $CH_3$ | $CF_3$ | H | S | Cl | Cl | $CH_2CH_3$ |
| $CH_3$ | $CF_3$ | H | O | Cl | F | $CH_2CH_2CH_3$ |
| $CH_3$ | $CF_3$ | H | S | Cl | F | $CH_2CH_2CH_3$ |
| $CH_3$ | $CF_3$ | H | O | Cl | Cl | $CH_2CH_2CH_3$ |
| $CH_3$ | $CF_3$ | H | S | Cl | Cl | $CH_2CH_2CH_3$ |
| $CH_3$ | $CF_3$ | H | O | Cl | F | $CF_3$ |
| $CH_3$ | $CF_3$ | H | S | Cl | F | $CF_3$ |
| $CH_3$ | $CF_3$ | H | O | Cl | Cl | $CF_3$ |
| $CH_3$ | $CF_3$ | H | S | Cl | Cl | $CF_3$ |
| $CH_3$ | $CF_3$ | H | O | Cl | F | $CF_2H$ |
| $CH_3$ | $CF_3$ | H | S | Cl | F | $CF_2H$ |

TABLE II-continued

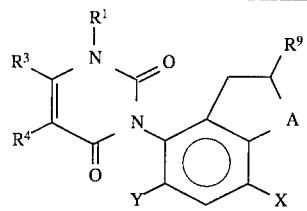

$R^9 = CH_3$ unless otherwise noted

| R¹ | R³ | R⁴ | A | X | Y | R⁹ |
|---|---|---|---|---|---|---|
| CH₃ | CF₃ | H | O | Cl | Cl | CF₂H |
| CH₃ | CF₃ | H | S | Cl | Cl | CF₂H |
| CH₃ | CF₃ | H | O | Cl | F | CFH₂ |
| CH₃ | CF₃ | H | S | Cl | F | CFH₂ |
| CH₃ | CF₃ | H | O | Cl | Cl | CFH₂ |
| CH₃ | CF₃ | H | S | Cl | Cl | CFH₂ |
| CH₃ | CF₃ | H | O | Cl | F | CH=CH₂ |
| CH₃ | CF₃ | H | S | Cl | F | CH=CH₂ |
| CH₃ | CF₃ | H | O | Cl | Cl | CH=CH₂ |
| CH₃ | CF₃ | H | S | Cl | Cl | CH=CH₂ |
| CH₃ | CF₃ | H | O | Cl | F | C≡CH |
| CH₃ | CF₃ | H | S | Cl | F | C≡CH |
| CH₃ | CF₃ | H | O | Cl | Cl | C≡CH |
| CH₃ | CF₃ | H | S | Cl | Cl | C≡CH |
| CH₃ | CF₃ | H | O | Cl | F | CN |
| CH₃ | CF₃ | H | S | Cl | F | CN |
| CH₃ | CF₃ | H | O | Cl | Cl | CN |
| CH₃ | CF₃ | H | S | Cl | Cl | CN |
| CF₃ | CF₃ | H | O | Cl | F | CH₂CH₃ |
| CF₃ | CF₃ | H | S | Cl | F | CH₂CH₃ |
| CF₃ | CF₃ | H | O | Cl | Cl | CH₂CH₃ |
| CF₃ | CF₃ | H | S | Cl | Cl | CH₂CH₃ |
| CF₃ | CF₃ | H | O | Cl | F | CH₂CH₂CH₃ |
| CF₃ | CF₃ | H | S | Cl | F | CH₂CH₂CH₃ |
| CF₃ | CF₃ | H | O | Cl | Cl | CH₂CH₂CH₃ |
| CF₃ | CF₃ | H | S | Cl | Cl | CH₂CH₂CH₃ |
| CF₃ | CF₃ | H | O | Cl | F | CF₃ |
| CF₃ | CF₃ | H | S | Cl | F | CF₃ |
| CF₃ | CF₃ | H | O | Cl | Cl | CF₃ |
| CF₃ | CF₃ | H | S | Cl | Cl | CF₃ |
| CF₃ | CF₃ | H | O | Cl | F | CF₂H |
| CF₃ | CF₃ | H | S | Cl | F | CF₂H |
| CF₃ | CF₃ | H | O | Cl | Cl | CF₂H |
| CF₃ | CF₃ | H | S | Cl | Cl | CF₂H |
| CF₃ | CF₃ | H | O | Cl | F | CFH₂ |
| CF₃ | CF₃ | H | S | Cl | F | CFH₂ |
| CF₃ | CF₃ | H | O | Cl | Cl | CFH₂ |
| CF₃ | CF₃ | H | S | Cl | Cl | CFH₂ |
| CF₃ | CF₃ | H | O | Cl | F | CH=CH₂ |
| CF₃ | CF₃ | H | S | Cl | F | CH=CH₂ |
| CF₃ | CF₃ | H | O | Cl | Cl | CH=CH₂ |
| CF₃ | CF₃ | H | S | Cl | Cl | CH=CH₂ |
| CF₃ | CF₃ | H | O | Cl | F | C≡CH |
| CF₃ | CF₃ | H | S | Cl | F | C≡CH |
| CF₃ | CF₃ | H | O | Cl | Cl | C≡CH |
| CF₃ | CF₃ | H | S | Cl | Cl | C≡CH |
| CF₃ | CF₃ | H | O | Cl | F | CN |
| CF₃ | CF₃ | H | S | Cl | F | CN |
| CF₃ | CF₃ | H | O | Cl | Cl | CN |
| CF₃ | CF₃ | H | S | Cl | Cl | CN |
| CH₃ | CF₃ | Br | O | Cl | F | CH₂CH₃ |
| CH₃ | CF₃ | Br | S | Cl | F | CH₂CH₃ |
| CH₃ | CF₃ | Br | O | Cl | Cl | CH₂CH₃ |
| CH₃ | CF₃ | Br | S | Cl | Cl | CH₂CH₃ |
| CH₃ | CF₃ | Br | O | Cl | F | CH₂CH₂CH₃ |
| CH₃ | CF₃ | Br | S | Cl | F | CH₂CH₂CH₃ |
| CH₃ | CF₃ | Br | O | Cl | Cl | CH₂CH₂CH₃ |
| CH₃ | CF₃ | Br | S | Cl | Cl | CH₂CH₂CH₃ |
| CH₃ | CF₃ | Br | O | Cl | F | CF₃ |
| CH₃ | CF₃ | Br | S | Cl | F | CF₃ |
| CH₃ | CF₃ | Br | O | Cl | Cl | CF₃ |
| CH₃ | CF₃ | Br | S | Cl | Cl | CF₃ |
| CH₃ | CF₃ | Br | O | Cl | F | CF₂H |
| CH₃ | CF₃ | Br | S | Cl | F | CF₂H |
| CH₃ | CF₃ | Br | O | Cl | Cl | CF₂H |
| CH₃ | CF₃ | Br | S | Cl | Cl | CF₂H |
| CH₃ | CF₃ | Br | O | Cl | F | CFH₂ |
| CH₃ | CF₃ | Br | S | Cl | F | CFH₂ |
| CH₃ | CF₃ | Br | O | Cl | Cl | CFH₂ |
| CH₃ | CF₃ | Br | S | Cl | Cl | CFH₂ |
| CH₃ | CF₃ | Br | O | Cl | F | CH=CH₂ |
| CH₃ | CF₃ | Br | S | Cl | F | CH=CH₂ |
| CH₃ | CF₃ | Br | O | Cl | Cl | CH=CH₂ |
| CH₃ | CF₃ | Br | S | Cl | Cl | CH=CH₂ |
| CH₃ | CF₃ | Br | O | Cl | F | C≡CH |
| CH₃ | CF₃ | Br | S | Cl | F | C≡CH |
| CH₃ | CF₃ | Br | O | Cl | Cl | C≡CH |
| CH₃ | CF₃ | Br | S | Cl | Cl | C≡CH |
| CH₃ | CF₃ | Cl | O | Cl | F | CH=CH₂ |
| CH₃ | CF₃ | Cl | S | Cl | F | CH=CH₂ |
| CH₃ | CF₃ | Cl | O | Cl | Cl | CH=CH₂ |
| CH₃ | CF₃ | Cl | S | Cl | Cl | CH=CH₂ |
| CH₃ | CF₃ | Cl | O | Cl | F | C≡CH |
| CH₃ | CF₃ | Cl | S | Cl | F | C≡CH |
| CH₃ | CF₃ | Cl | O | Cl | Cl | C≡CH |
| CH₃ | CF₃ | Cl | S | Cl | Cl | C≡CH |
| CH₃ | CF₃ | Br | O | Cl | F | CN |
| CH₃ | CF₃ | Br | S | Cl | F | CN |
| CH₃ | CF₃ | Br | O | Cl | Cl | CN |
| CH₃ | CF₃ | Br | S | Cl | Cl | CN |
| CH₃ | —(CH₂)₃— | | O | Cl | F | CH₂CH₃ |
| CH₃ | —(CH₂)₃— | | S | Cl | F | CH₂CH₃ |
| CH₃ | —(CH₂)₃— | | O | Cl | Cl | CH₂CH₃ |
| CH₃ | —(CH₂)₃— | | S | Cl | Cl | CH₂CH₃ |
| CH₃ | —(CH₂)₄— | | O | Cl | F | CH₂CH₃ |
| CH₃ | —(CH₂)₄— | | S | Cl | F | CH₂CH₃ |

TABLE II-continued

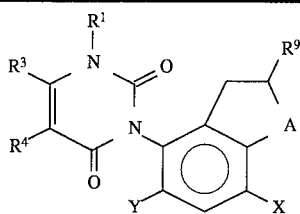

$R^9 = CH_3$ unless otherwise noted

| $R^1$ | $R^3$ | $R^4$ | A | X | Y | $R^9$ |
|---|---|---|---|---|---|---|
| CH₃ | —(CH₂)₄— | | O | Cl | Cl | CH₂CH₃ |
| CH₃ | —(CH₂)₄— | | S | Cl | Cl | CH₂CH₃ |
| CH₃ | —(CH₂)₃— | | O | Cl | F | CF₃ |
| CH₃ | —(CH₂)₃— | | S | Cl | F | CF₃ |
| CH₃ | —(CH₂)₃— | | O | Cl | Cl | CF₃ |
| CH₃ | —(CH₂)₃— | | S | Cl | Cl | CF₃ |
| CH₃ | —(CH₂)₄— | | S | Cl | F | CF₃ |
| CH₃ | —(CH₂)₄— | | O | Cl | F | CF₃ |
| CH₃ | —(CH₂)₄— | | S | Cl | Cl | CF₃ |
| CH₃ | —(CH₂)₄— | | O | Cl | Cl | CF₃ |
| CH₃ | —(CH₂)₃— | | O | Cl | F | CF₂H |
| CH₃ | —(CH₂)₃— | | S | Cl | F | CF₂H |
| CH₃ | —(CH₂)₃— | | O | Cl | Cl | CF₂H |
| CH₃ | —(CH₂)₃— | | S | Cl | Cl | CF₂H |
| CH₃ | —(CH₂)₄— | | O | Cl | F | CF₂H |
| CH₃ | —(CH₂)₄— | | S | Cl | F | CF₂H |
| CH₃ | —(CH₂)₄— | | O | Cl | Cl | CF₂H |
| CH₃ | —(CH₂)₄— | | S | Cl | Cl | CF₂H |
| CH₃ | —(CH₂)₃— | | O | Cl | F | CFH₂ |
| CH₃ | —(CH₂)₃— | | S | Cl | F | CFH₂ |
| CH₃ | —(CH₂)₃— | | O | Cl | Cl | CFH₂ |
| CH₃ | —(CH₂)₃— | | S | Cl | Cl | CFH₂ |
| CH₃ | —(CH₂)₄— | | O | Cl | F | CFH₂ |
| CH₃ | —(CH₂)₄— | | S | Cl | F | CFH₂ |
| CH₃ | —(CH₂)₄— | | O | Cl | Cl | CFH₂ |
| CH₃ | —(CH₂)₄— | | S | Cl | Cl | CFH₂ |
| CH₃ | —(CH₂)₃— | | O | Cl | F | CH=CH₂ |
| CH₃ | —(CH₂)₃— | | S | Cl | F | CH=CH₂ |
| CH₃ | —(CH₂)₃— | | O | Cl | Cl | CH=CH₂ |
| CH₃ | —(CH₂)₃— | | S | Cl | Cl | CH=CH₂ |
| CH₃ | —(CH₂)₄— | | O | Cl | F | CH=CH₂ |
| CH₃ | —(CH₂)₄— | | S | Cl | F | CH=CH₂ |
| CH₃ | —(CH₂)₄— | | O | Cl | Cl | CH=CH₂ |
| CH₃ | —(CH₂)₄— | | S | Cl | Cl | CH=CH₂ |
| CH₃ | —(CH₂)₃— | | O | Cl | F | C≡CH |
| CH₃ | —(CH₂)₃— | | S | Cl | F | C≡CH |
| CH₃ | —(CH₂)₃— | | O | Cl | Cl | C≡CH |
| CH₃ | —(CH₂)₃— | | S | Cl | Cl | C≡CH |
| CH₃ | —(CH₂)₄— | | O | Cl | F | C≡CH |
| CH₃ | —(CH₂)₄— | | S | Cl | F | C≡CH |
| CH₃ | —(CH₂)₄— | | O | Cl | Cl | C≡CH |
| CH₃ | —(CH₂)₄— | | S | Cl | Cl | C≡CH |
| CH₃ | —(CH₂)₃— | | O | Cl | F | CN |
| CH₃ | —(CH₂)₃— | | S | Cl | F | CN |
| CH₃ | —(CH₂)₃— | | O | Cl | Cl | CN |
| CH₃ | —(CH₂)₃— | | S | Cl | Cl | CN |
| CH₃ | —(CH₂)₄— | | O | Cl | F | CN |
| CH₃ | —(CH₂)₄— | | S | Cl | F | CN |
| CH₃ | —(CH₂)₄— | | O | Cl | Cl | CN |
| CH₃ | —(CH₂)₄— | | S | Cl | Cl | CN |
| CH₃ | CF₃ | H | O | Cl | F | CH₂OH |
| CH₃ | CF₃ | H | O | Cl | F | CH₂OC(O)CH₃ |
| CH₃ | CF₃ | H | O | Cl | F | CO₂CH₃ |
| CH₃ | CF₃ | H | O | Cl | F | CON(CH₃)₂ |
| CH₃ | N(CH₃)₂ | H | O | Cl | F | CH₂OH |
| CH₃ | N(CH₃)₂ | H | O | Cl | F | CH₂OC(O)CH₃ |
| CH₃ | N(CH₃)₂ | H | O | Cl | F | CO₂CH₃ |
| CH₃ | CF₃ | Br | O | Cl | F | CH₂OH |
| CH₃ | CF₃ | Br | O | Cl | F | CH₂OC(O)CH₃ |
| CH₃ | CF₃ | Br | O | Cl | F | CO₂CH₃ |
| CH₃ | CF₃ | Br | S | Cl | F | CH₂OH |

TABLE III

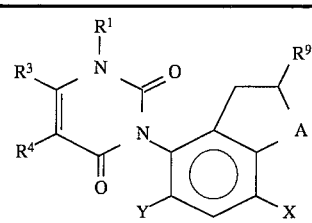

| $R^1$ | $R^3$ | A | X | Y | $R^2$ | Z |
|---|---|---|---|---|---|---|
| CH₃ | N(CH₃)₂ | O | Cl | F | H | H |
| CH₃ | N(CH₃)₂ | O | Cl | Cl | H | H |
| CH₃ | N(CH₃)₂ | S | Cl | F | H | H |
| CH₃ | N(CH₃)₂ | S | Cl | Cl | H | H |
| CH₃ | N(CH₃)₂ | O | Cl | F | CH₂C≡CH | H |
| CH₃ | N(CH₃)₂ | O | Cl | Cl | CH₂C≡CH | H |
| CH₃ | N(CH₃)₂ | S | Cl | F | CH₂C≡CH | H |
| CH₃ | N(CH₃)₂ | S | Cl | Cl | CH₂C≡CH | H |
| CH₃ | N(CH₃)₂ | O | Cl | F | CH₂Ph | H |
| CH₃ | N(CH₃)₂ | O | Cl | Cl | CH₂Ph | H |
| CH₃ | N(CH₃)₂ | S | Cl | F | CH₂Ph | H |
| CH₃ | N(CH₃)₂ | S | Cl | Cl | CH₂Ph | H |
| CH₃ | N(CH₃)₂ | O | Cl | F | iPr | H |
| CH₃ | N(CH₃)₂ | O | Cl | Cl | iPr | H |
| CH₃ | N(CH₃)₂ | S | Cl | F | iPr | H |
| CH₃ | N(CH₃)₂ | S | Cl | Cl | iPr | H |
| CH₃ | N(CH₃)₂ | O | Cl | F | CHMeC≡CH | H |
| CH₃ | N(CH₃)₂ | O | Cl | Cl | CHMeC≡CH | H |
| CH₃ | N(CH₃)₂ | S | Cl | F | CHMeC≡CH | H |
| CH₃ | N(CH₃)₂ | S | Cl | Cl | CHMeC≡CH | H |

TABLE III-continued

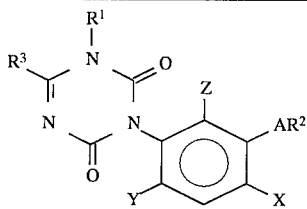

| R¹ | R³ | A | X | Y | R² | Z |
|---|---|---|---|---|---|---|
| CH₃ | N(CH₃)₂ | O | Cl | F | CH₂CH=CH₂ | H |
| CH₃ | N(CH₃)₂ | O | Cl | Cl | CH₂CH=CH₂ | H |
| CH₃ | N(CH₃)₂ | S | Cl | F | CH₂CH=CH₂ | H |
| CH₃ | N(CH₃)₂ | S | Cl | Cl | CH₂CH=CH₂ | H |
| CH₃ | N(CH₃)₂ | O | Cl | F | CHMeCO₂Me | H |
| CH₃ | N(CH₃)₂ | O | Cl | Cl | CHMeCO₂Me | H |
| CH₃ | N(CH₃)₂ | S | Cl | F | CHMeCO₂Me | H |
| CH₃ | N(CH₃)₂ | S | Cl | Cl | CHMeCO₂Me | H |
| CH₃ | N(CH₃)₂ | O | Cl | F | —CH(CH₃)CH₂— | |
| CH₃ | N(CH₃)₂ | O | Cl | Cl | —CH(CH₃)CH₂— | |
| CH₃ | N(CH₃)₂ | S | Cl | F | —CH(CH₃)CH₂— | |
| CH₃ | N(CH₃)₂ | S | Cl | Cl | —CH(CH₃)CH₂— | |
| CH₃ | CF₃ | O | Cl | F | H | H |
| CH₃ | CF₃ | O | Cl | Cl | H | H |
| CH₃ | CF₃ | S | Cl | F | H | H |
| CH₃ | CF₃ | S | Cl | Cl | H | H |
| CH₃ | CF₃ | O | Cl | F | CH₂C≡CH | H |
| CH₃ | CF₃ | O | Cl | Cl | CH₂C≡CH | H |
| CH₃ | CF₃ | S | Cl | F | CH₂C≡CH | H |
| CH₃ | CF₃ | S | Cl | Cl | CH₂C≡CH | H |
| CH₃ | CF₃ | O | Cl | F | CH₂Ph | H |
| CH₃ | CF₃ | O | Cl | Cl | CH₂Ph | H |
| CH₃ | CF₃ | S | Cl | F | CH₂Ph | H |
| CH₃ | CF₃ | S | Cl | Cl | CH₂Ph | H |
| CH₃ | CF₃ | O | Cl | F | iPr | H |
| CH₃ | CF₃ | O | Cl | Cl | iPr | H |
| CH₃ | CF₃ | S | Cl | F | iPr | H |
| CH₃ | CF₃ | S | Cl | Cl | iPr | H |
| CH₃ | CF₃ | O | Cl | F | CHMeC≡CH | H |
| CH₃ | CF₃ | O | Cl | Cl | CHMeC≡CH | H |
| CH₃ | CF₃ | S | Cl | F | CHMeC≡CH | H |
| CH₃ | CF₃ | S | Cl | Cl | CHMeC≡CH | H |
| CH₃ | CF₃ | O | Cl | F | CH₂CH=CH₂ | H |
| CH₃ | CF₃ | O | Cl | Cl | CH₂CH=CH₂ | H |
| CH₃ | CF₃ | S | Cl | F | CH₂CH=CH₂ | H |
| CH₃ | CF₃ | S | Cl | Cl | CH₂CH=CH₂ | H |
| CH₃ | CF₃ | O | Cl | F | CHMeCO₂Me | H |
| CH₃ | CF₃ | O | Cl | Cl | CHMeCO₂Me | H |
| CH₃ | CF₃ | S | Cl | F | CHMeCO₂Me | H |
| CH₃ | CF₃ | S | Cl | Cl | CHMeCO₂Me | H |
| CH₃ | CF₃ | O | Cl | F | —CH(CH₃)CH₂— | |
| CH₃ | CF₃ | O | Cl | Cl | —CH(CH₃)CH₂— | |
| CH₃ | CF₃ | S | Cl | F | —CH(CH₃)CH₂— | |
| CH₃ | CF₃ | S | Cl | Cl | —CH(CH₃)CH₂— | |
| CF₃ | N(CH₃)₂ | O | Cl | F | H | H |
| CF₃ | N(CH₃)₂ | O | Cl | Cl | H | H |
| CF₃ | N(CH₃)₂ | S | Cl | F | H | H |
| CF₃ | N(CH₃)₂ | S | Cl | Cl | H | H |
| CF₃ | N(CH₃)₂ | O | Cl | F | CH₂C≡CH | H |
| CF₃ | N(CH₃)₂ | O | Cl | Cl | CH₂C≡CH | H |
| CF₃ | N(CH₃)₂ | S | Cl | F | CH₂C≡CH | H |
| CF₃ | N(CH₃)₂ | S | Cl | Cl | CH₂C≡CH | H |
| CF₃ | N(CH₃)₂ | O | Cl | F | CH₂Ph | H |
| CF₃ | N(CH₃)₂ | O | Cl | Cl | CH₂Ph | H |
| CF₃ | N(CH₃)₂ | S | Cl | F | CH₂Ph | H |
| CF₃ | N(CH₃)₂ | S | Cl | Cl | CH₂Ph | H |
| CF₃ | N(CH₃)₂ | O | Cl | F | iPr | H |
| CF₃ | N(CH₃)₂ | O | Cl | Cl | iPr | H |
| CF₃ | N(CH₃)₂ | S | Cl | F | iPr | H |
| CF₃ | N(CH₃)₂ | S | Cl | Cl | iPr | H |
| CF₃ | N(CH₃)₂ | O | Cl | F | CHMeC≡CH | H |
| CF₃ | N(CH₃)₂ | O | Cl | Cl | CHMeC≡CH | H |
| CF₃ | N(CH₃)₂ | S | Cl | F | CHMeC≡CH | H |
| CF₃ | N(CH₃)₂ | S | Cl | Cl | CHMeC≡CH | H |
| CF₃ | N(CH₃)₂ | O | Cl | F | CH₂CH=CH₂ | H |
| CF₃ | N(CH₃)₂ | O | Cl | Cl | CH₂CH=CH₂ | H |
| CF₃ | N(CH₃)₂ | S | Cl | F | CH₂CH=CH₂ | H |
| CF₃ | N(CH₃)₂ | S | Cl | Cl | CH₂CH=CH₂ | H |
| CF₃ | N(CH₃)₂ | O | Cl | F | CHMeCO₂Me | H |
| CF₃ | N(CH₃)₂ | O | Cl | Cl | CHMeCO₂Me | H |
| CF₃ | N(CH₃)₂ | S | Cl | F | CHMeCO₂Me | H |
| CF₃ | N(CH₃)₂ | S | Cl | Cl | CHMeCO₂Me | H |
| CF₃ | N(CH₃)₂ | O | Cl | F | —CH(CH₃)CH₂— | |
| CF₃ | N(CH₃)₂ | O | Cl | Cl | —CH(CH₃)CH₂— | |
| CF₃ | N(CH₃)₂ | S | Cl | F | —CH(CH₃)CH₂— | |
| CF₃ | N(CH₃)₂ | S | Cl | Cl | —CH(CH₃)CH₂— | |
| CF₃ | CF₃ | O | Cl | F | H | H |
| CF₃ | CF₃ | O | Cl | Cl | H | H |
| CF₃ | CF₃ | S | Cl | F | H | H |
| CF₃ | CF₃ | S | Cl | Cl | H | H |
| CF₃ | CF₃ | O | Cl | F | CH₂C≡CH | H |
| CF₃ | CF₃ | O | Cl | Cl | CH₂C≡CH | H |
| CF₃ | CF₃ | S | Cl | F | CH₂C≡CH | H |
| CF₃ | CF₃ | S | Cl | Cl | CH₂C≡CH | H |
| CF₃ | CF₃ | O | Cl | F | CH₂Ph | H |
| CF₃ | CF₃ | O | Cl | Cl | CH₂Ph | H |
| CF₃ | CF₃ | S | Cl | F | CH₂Ph | H |
| CF₃ | CF₃ | S | Cl | Cl | CH₂Ph | H |
| CF₃ | CF₃ | O | Cl | F | Pr | H |
| CF₃ | CF₃ | O | Cl | Cl | Pr | H |
| CF₃ | CF₃ | S | Cl | F | Pr | H |

TABLE III-continued

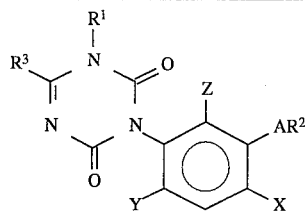

| R¹ | R³ | A | X | Y | R² | Z |
|---|---|---|---|---|---|---|
| CF₃ | CF₃ | S | Cl | Cl | Pr | H |
| CF₃ | CF₃ | O | Cl | F | CHMeC≡CH | H |
| CF₃ | CF₃ | O | Cl | Cl | CHMeC≡CH | H |
| CF₃ | CF₃ | S | Cl | F | CHMeC≡CH | H |
| CF₃ | CF₃ | S | Cl | Cl | CHMeC≡CH | H |
| CF₃ | CF₃ | O | Cl | F | CH₂CH=CH₂ | H |
| CF₃ | CF₃ | O | Cl | Cl | CH₂CH=CH₂ | H |
| CF₃ | CF₃ | S | Cl | F | CH₂CH=CH₂ | H |
| CF₃ | CF₃ | S | Cl | Cl | CH₂CH=CH₂ | H |
| CF₃ | CF₃ | O | Cl | F | CHMeCO₂Me | H |
| CF₃ | CF₃ | O | Cl | Cl | CHMeCO₂Me | H |
| CF₃ | CF₃ | S | Cl | F | CHMeCO₂Me | H |
| CF₃ | CF₃ | S | Cl | Cl | CHMeCO₂Me | H |
| CF₃ | CF₃ | O | Cl | F | —CH(CH₃)CH₂— | |
| CF₃ | CF₃ | O | Cl | Cl | —CH(CH₃)CH₂— | |
| CF₃ | CF₃ | S | Cl | F | —CH(CH₃)CH₂— | |
| CF₃ | CF₃ | S | Cl | Cl | —CH(CH₃)CH₂— | |
| i-Pr | N(CH₃)₂ | O | Cl | F | H | H |
| i-Pr | N(CH₃)₂ | O | Cl | Cl | H | H |
| i-Pr | N(CH₃)₂ | S | Cl | F | H | H |
| i-Pr | N(CH₃)₂ | S | Cl | Cl | H | H |
| i-Pr | N(CH₃)₂ | O | Cl | F | CH₂C≡CH | H |
| i-Pr | N(CH₃)₂ | O | Cl | Cl | CH₂C≡CH | H |
| i-Pr | N(CH₃)₂ | S | Cl | F | CH₂C≡CH | H |
| i-Pr | N(CH₃)₂ | S | Cl | Cl | CH₂C≡CH | H |
| i-Pr | N(CH₃)₂ | O | Cl | F | CH₂Ph | H |
| i-Pr | N(CH₃)₂ | O | Cl | Cl | CH₂Ph | H |
| i-Pr | N(CH₃)₂ | S | Cl | F | CH₂Ph | H |
| i-Pr | N(CH₃)₂ | S | Cl | Cl | CH₂Ph | H |
| i-Pr | N(CH₃)₂ | O | Cl | F | iPr | H |
| i-Pr | N(CH₃)₂ | O | Cl | Cl | iPr | H |
| i-Pr | N(CH₃)₂ | S | Cl | F | iPr | H |
| i-Pr | N(CH₃)₂ | S | Cl | Cl | iPr | H |
| i-Pr | N(CH₃)₂ | O | Cl | F | CHMeC≡CH | H |
| i-Pr | N(CH₃)₂ | O | Cl | Cl | CHMeC≡CH | H |
| i-Pr | N(CH₃)₂ | S | Cl | F | CHMeC≡CH | H |
| i-Pr | N(CH₃)₂ | S | Cl | Cl | CHMeC≡CH | H |
| i-Pr | N(CH₃)₂ | O | Cl | F | CH₂CH=CH₂ | H |
| i-Pr | N(CH₃)₂ | O | Cl | Cl | CH₂CH=CH₂ | H |
| i-Pr | N(CH₃)₂ | S | Cl | F | CH₂CH=CH₂ | H |
| i-Pr | N(CH₃)₂ | S | Cl | Cl | CH₂CH=CH₂ | H |
| i-Pr | N(CH₃)₂ | O | Cl | F | CHMeCO₂Me | H |
| i-Pr | N(CH₃)₂ | O | Cl | Cl | CHMeCO₂Me | H |
| i-Pr | N(CH₃)₂ | S | Cl | F | CHMeCO₂Me | H |
| i-Pr | N(CH₃)₂ | S | Cl | Cl | CHMeCO₂Me | H |
| i-Pr | N(CH₃)₂ | O | Cl | F | —CH(CH₃)CH₂— | |
| i-Pr | N(CH₃)₂ | O | Cl | Cl | —CH(CH₃)CH₂— | |
| i-Pr | N(CH₃)₂ | S | Cl | F | —CH(CH₃)CH₂— | |
| i-Pr | N(CH₃)₂ | S | Cl | Cl | —CH(CH₃)CH₂— | |
| i-Pr | CF₃ | O | Cl | F | H | H |
| i-Pr | CF₃ | O | Cl | Cl | H | H |
| i-Pr | CF₃ | S | Cl | F | H | H |
| i-Pr | CF₃ | S | Cl | Cl | H | H |
| i-Pr | CF₃ | O | Cl | F | CH₂C≡CH | H |
| i-Pr | CF₃ | O | Cl | Cl | CH₂C≡CH | H |
| i-Pr | CF₃ | S | Cl | F | CH₂C≡CH | H |
| i-Pr | CF₃ | S | Cl | Cl | CH₂C≡CH | H |
| i-Pr | CF₃ | O | Cl | F | CH₂Ph | H |
| i-Pr | CF₃ | O | Cl | Cl | CH₂Ph | H |
| i-Pr | CF₃ | S | Cl | F | CH₂Ph | H |
| i-Pr | CF₃ | S | Cl | Cl | CH₂Ph | H |
| i-Pr | CF₃ | O | Cl | F | iPr | H |
| i-Pr | CF₃ | O | Cl | Cl | iPr | H |
| i-Pr | CF₃ | S | Cl | F | iPr | H |
| i-Pr | CF₃ | S | Cl | Cl | iPr | H |
| i-Pr | CF₃ | O | Cl | F | CHMeC≡CH | H |
| i-Pr | CF₃ | O | Cl | Cl | CHMeC≡CH | H |
| i-Pr | CF₃ | S | Cl | F | CHMeC≡CH | H |
| i-Pr | CF₃ | S | Cl | Cl | CHMeC≡CH | H |
| i-Pr | CF₃ | O | Cl | F | CH₂CH=CH₂ | H |
| i-Pr | CF₃ | O | Cl | Cl | CH₂CH=CH₂ | H |
| i-Pr | CF₃ | S | Cl | F | CH₂CH=CH₂ | H |
| i-Pr | CF₃ | S | Cl | Cl | CH₂CH=CH₂ | H |
| i-Pr | CF₃ | O | Cl | F | CHMeCO₂Me | H |
| i-Pr | CF₃ | O | Cl | Cl | CHMeCO₂Me | H |
| i-Pr | CF₃ | S | Cl | F | CHMeCO₂Me | H |
| i-Pr | CF₃ | S | Cl | Cl | CHMeCO₂Me | H |
| i-Pr | CF₃ | O | Cl | F | —CH(CH₃)CH₂— | |
| i-Pr | CF₃ | O | Cl | Cl | —CH(CH₃)CH₂— | |
| i-Pr | CF₃ | S | Cl | F | —CH(CH₃)CH₂— | |
| i-Pr | CF₃ | S | Cl | Cl | —CH(CH₃)CH₂— | |
| CH₂C≡CH | N(CH₃)₂ | O | Cl | F | H | H |
| CH₂C≡CH | N(CH₃)₂ | O | Cl | Cl | H | H |
| CH₂C≡CH | N(CH₃)₂ | S | Cl | F | H | H |
| CH₂C≡CH | N(CH₃)₂ | S | Cl | Cl | H | H |

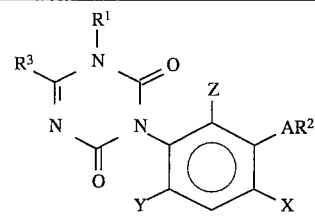

TABLE III-continued

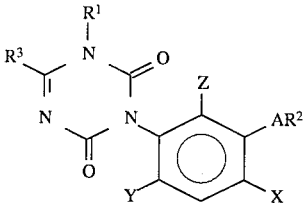

| R¹ | R³ | A | X | Y | R² | Z |
|---|---|---|---|---|---|---|
| CH₂C≡CH | N(CH₃)₂ | O | Cl | F | CH₂C≡CH | H |
| CH₂C≡CH | N(CH₃)₂ | O | Cl | Cl | CH₂C≡CH | H |
| CH₂C≡CH | N(CH₃)₂ | S | Cl | F | CH₂C≡CH | H |
| CH₂C≡CH | N(CH₃)₂ | S | Cl | Cl | CH₂C≡CH | H |
| CH₂C≡CH | N(CH₃)₂ | O | Cl | F | CH₂Ph | H |
| CH₂C≡CH | N(CH₃)₂ | O | Cl | Cl | CH₂Ph | H |
| CH₂C≡CH | N(CH₃)₂ | S | Cl | F | CH₂Ph | H |
| CH₂C≡CH | N(CH₃)₂ | S | Cl | Cl | CH₂Ph | H |
| CH₂C≡CH | N(CH₃)₂ | O | Cl | F | iPr | H |
| CH₂C≡CH | N(CH₃)₂ | O | Cl | Cl | iPr | H |
| CH₂C≡CH | N(CH₃)₂ | S | Cl | F | iPr | H |
| CH₂C≡CH | N(CH₃)₂ | S | Cl | Cl | iPr | H |
| CH₂C≡CH | N(CH₃)₂ | O | Cl | F | CHMeC≡CH | H |
| CH₂C≡CH | N(CH₃)₂ | O | Cl | Cl | CHMeC≡CH | H |
| CH₂C≡CH | N(CH₃)₂ | S | Cl | F | CHMeC≡CH | H |
| CH₂C≡CH | N(CH₃)₂ | S | Cl | Cl | CHMeC≡CH | H |
| CH₂C≡CH | N(CH₃)₂ | O | Cl | F | CH₂CH=CH₂ | H |
| CH₂C≡CH | N(CH₃)₂ | O | Cl | Cl | CH₂CH=CH₂ | H |
| CH₂C≡CH | N(CH₃)₂ | S | Cl | F | CH₂CH=CH₂ | H |
| CH₂C≡CH | N(CH₃)₂ | S | Cl | Cl | CH₂CH=CH₂ | H |
| CH₂C≡CH | N(CH₃)₂ | O | Cl | F | CHMeCO₂Me | H |
| CH₂C≡CH | N(CH₃)₂ | O | Cl | Cl | CHMeCO₂Me | H |

TABLE III-continued

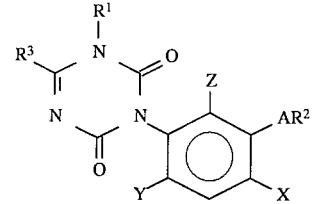

| R¹ | R³ | A | X | Y | R² | Z |
|---|---|---|---|---|---|---|
| CH₂C≡CH | N(CH₃)₂ | S | Cl | F | CHMeCO₂Me | H |
| CH₂C≡CH | N(CH₃)₂ | S | Cl | Cl | CHMeCO₂Me | H |
| CH₂C≡CH | N(CH₃)₂ | O | Cl | F | —CH(CH₃)CH₂— | |
| CH₂C≡CH | N(CH₃)₂ | O | Cl | Cl | —CH(CH₃)CH₂— | |
| CH₂C≡CH | N(CH₃)₂ | S | Cl | F | —CH(CH₃)CH₂— | |
| CH₂C≡CH | N(CH₃)₂ | S | Cl | Cl | —CH(CH₃)CH₂— | |
| CH₂C≡CH | CF₃ | O | Cl | F | H | H |
| CH₂C≡CH | CF₃ | O | Cl | Cl | H | H |
| CH₂C≡CH | CF₃ | S | Cl | F | H | H |
| CH₂C≡CH | CF₃ | S | Cl | Cl | H | H |
| CH₂C≡CH | CF₃ | O | Cl | F | CH₂C≡CH | H |
| CH₂C≡CH | CF₃ | O | Cl | Cl | CH₂C≡CH | H |
| CH₂C≡CH | CF₃ | S | Cl | F | CH₂C≡CH | H |
| CH₂C≡CH | CF₃ | S | Cl | Cl | CH₂C≡CH | H |
| CH₂C≡CH | CF₃ | O | Cl | F | CH₂Ph | H |
| CH₂C≡CH | CF₃ | O | Cl | Cl | CH₂Ph | H |
| CH₂C≡CH | CF₃ | S | Cl | F | CH₂Ph | H |
| CH₂C≡CH | CF₃ | S | Cl | Cl | CH₂Ph | H |
| CH₂C≡CH | CF₃ | O | Cl | F | iPr | H |
| CH₂C≡CH | CF₃ | O | Cl | Cl | iPr | H |
| CH₂C≡CH | CF₃ | S | Cl | F | iPr | H |
| CH₂C≡CH | CF₃ | S | Cl | Cl | iPr | H |
| CH₂C≡CH | CF₃ | O | Cl | F | CHMeC≡CH | H |

TABLE III-continued

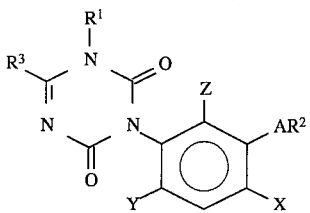

| R¹ | R³ | A | X | Y | R² | Z |
|---|---|---|---|---|---|---|
| CH₂C≡CH | CF₃ | O | Cl | Cl | CHMeC≡CH | H |
| CH₂C≡CH | CF₃ | S | Cl | F | CHMeC≡CH | H |
| CH₂C≡CH | CF₃ | S | Cl | Cl | CHMeC≡CH | H |
| CH₂C≡CH | CF₃ | O | Cl | F | CH₂CH=CH₂ | H |
| CH₂C≡CH | CF₃ | O | Cl | Cl | CH₂CH=CH₂ | H |
| CH₂C≡CH | CF₃ | S | Cl | F | CH₂CH=CH₂ | H |
| CH₂C≡CH | CF₃ | S | Cl | Cl | CH₂CH=CH₂ | H |
| CH₂C≡CH | CF₃ | O | Cl | F | CHMeCO₂Me | H |
| CH₂C≡CH | CF₃ | O | Cl | Cl | CHMeCO₂Me | H |
| CH₂C≡CH | CF₃ | S | Cl | F | CHMeCO₂Me | H |
| CH₂C≡CH | CF₃ | S | Cl | Cl | CHMeCO₂Me | H |
| CH₂C≡CH | CF₃ | O | Cl | F | —CH(CH₃)CH₂— | |
| CH₂C≡CH | CF₃ | O | Cl | Cl | —CH(CH₃)CH₂— | |
| CH₂C≡CH | CF₃ | S | Cl | F | —CH(CH₃)CH₂— | |
| CH₂C≡CH | CF₃ | S | Cl | Cl | —CH(CH₃)CH₂— | |
| CHO | CF₃ | O | Cl | F | CHMeC≡CH | H |
| CHO | CF₃ | O | Cl | Cl | CHMeC≡CH | H |
| CHO | CF₃ | O | Cl | F | —CH(CH₃)CH₂— | |
| CHO | CF₃ | O | Cl | Cl | —CH(CH₃)CH₂— | |
| COCH₃ | CF₃ | O | Cl | F | CHMeC≡CH | H |
| COCH₃ | CF₃ | O | Cl | Cl | CHMeC≡CH | H |
| COCH₃ | CF₃ | O | Cl | F | —CH(CH₃)CH₂— | |
| COCH₃ | CF₃ | O | Cl | Cl | —CH(CH₃)CH₂— | |
| COCH₃ | N(CH₃)₂ | O | Cl | F | CHMeC≡CH | H |
| COCH₃ | N(CH₃)₂ | O | Cl | Cl | CHMeC≡CH | H |

TABLE III-continued

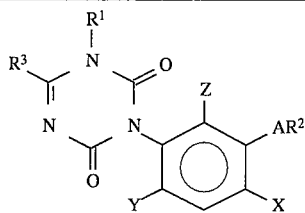

| R¹ | R³ | A | X | Y | R² | Z |
|---|---|---|---|---|---|---|
| COCH₃ | N(CH₃)₂ | O | Cl | F | —CH(CH₃)CH₂— | |
| COCH₃ | N(CH₃)₂ | O | Cl | Cl | —CH(CH₃)CH₂— | |
| CHF₂ | CF₃ | O | Cl | F | CHMeC≡CH | H |
| CHF₂ | CF₃ | O | Cl | Cl | CHMeC≡CH | H |
| CHF₂ | CF₃ | O | Cl | F | —CH(CH₃)CH₂— | |
| CHF₂ | CF₃ | O | Cl | Cl | —CH(CH₃)CH₂— | |
| CHF₂ | N(CH₃)₂ | O | Cl | F | CHMeC≡CH | H |
| CHF₂ | N(CH₃)₂ | O | Cl | Cl | CHMeC≡CH | H |
| CHF₂ | N(CH₃)₂ | O | Cl | F | —CH(CH₃)CH₂— | |
| CHF₂ | N(CH₃)₂ | O | Cl | Cl | —CH(CH₃)CH₂— | |
| CH₂F | CF₃ | O | Cl | F | CHMeC≡CH | H |
| CH₂F | CF₃ | O | Cl | Cl | CHMeC≡CH | H |
| CH₂F | CF₃ | O | Cl | F | —CH(CH₃)CH₂— | |
| CH₂F | CF₃ | O | Cl | Cl | —CH(CH₃)CH₂— | |
| CH₂F | N(CH₃)₂ | O | Cl | F | CHMeC≡CH | H |
| CH₂F | N(CH₃)₂ | O | Cl | Cl | CHMeC≡CH | H |
| CH₂F | N(CH₃)₂ | O | Cl | F | —CH(CH₃)CH₂— | |
| CH₂F | N(CH₃)₂ | O | Cl | Cl | —CH(CH₃)CH₂— | |
| CHMeC≡CH | N(CH₃)₂ | O | Cl | F | CHMeC≡CH | H |
| CHMeC≡CH | N(CH₃)₂ | O | Cl | Cl | CHMeC≡CH | H |
| CHMeC≡CH | N(CH₃)₂ | O | Cl | F | —CH(CH₃)CH₂— | |
| CHMeC≡CH | N(CH₃)₂ | O | Cl | Cl | —CH(CH₃)CH₂— | |
| CH₃ | N(CH₃)₂ | O | Cl | F | —CH(CF₃)CH₂— | |
| CH₃ | N(CH₃)₂ | O | Cl | Cl | —CH(CF₃)CH₂— | |
| CH₃ | N(CH₃)₂ | S | Cl | F | —CH(CF₃)CH₂— | |
| CH₃ | N(CH₃)₂ | S | Cl | Cl | —CH(CF₃)CH₂— | |
| CH₃ | CF₃ | O | Cl | F | —CH(CF₃)CH₂— | |
| CH₃ | CF₃ | O | Cl | Cl | —CH(CF₃)CH₂— | |
| CH₃ | CF₃ | S | Cl | F | —CH(CF₃)CH₂— | |
| CH₃ | CF₃ | S | Cl | Cl | —CH(CF₃)CH₂— | |
| CF₃ | N(CH₃)₂ | O | Cl | F | —CH(CF₃)CH₂— | |
| CF₃ | N(CH₃)₂ | O | Cl | Cl | —CH(CF₃)CH₂— | |
| CF₃ | N(CH₃)₂ | S | Cl | F | —CH(CF₃)CH₂— | |
| CF₃ | N(CH₃)₂ | S | Cl | Cl | —CH(CF₃)CH₂— | |
| CF₃ | CF₃ | O | Cl | F | —CH(CF₃)CH₂— | |
| CF₃ | CF₃ | O | Cl | Cl | —CH(CF₃)CH₂— | |
| CF₃ | CF₃ | S | Cl | F | —CH(CF₃)CH₂— | |
| CF₃ | CF₃ | S | Cl | Cl | —CH(CF₃)CH₂— | |
| CH₂F | N(CH₃)₂ | O | Cl | F | —CH(CF₃)CH₂— | |
| CH₂F | N(CH₃)₂ | O | Cl | Cl | —CH(CF₃)CH₂— | |

TABLE III-continued

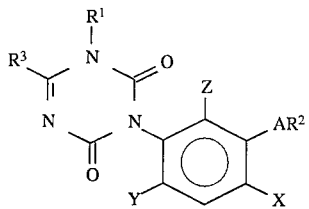

| R¹ | R³ | A | X | Y | R² Z |
|---|---|---|---|---|---|
| CH₂F | N(CH₃)₂ | S | Cl | F | —CH(CF₃)CH₂— |
| CH₂F | N(CH₃)₂ | S | Cl | Cl | —CH(CF₃)CH₂— |
| CH₂F | CF₃ | O | Cl | F | —CH(CF₃)CH₂— |
| CH₂F | CF₃ | O | Cl | Cl | —CH(CF₃)CH₂— |
| CH₂F | CF₃ | S | Cl | F | —CH(CF₃)CH₂— |
| CH₂F | CF₃ | S | Cl | Cl | —CH(CF₃)CH₂— |
| CH₃ | N(CH₃)₂ | O | Cl | F | —CH(CH=CH₂)CH₂— |
| CH₃ | N(CH₃)₂ | O | Cl | Cl | —CH(CH=CH₂)CH₂— |
| CH₃ | N(CH₃)₂ | S | Cl | F | —CH(CH=CH₂)CH₂— |
| CH₃ | N(CH₃)₂ | S | Cl | Cl | —CH(CH=CH₂)CH₂— |
| CH₃ | CF₃ | O | Cl | F | —CH(CH=CH₂)CH₂— |
| CH₃ | CF₃ | O | Cl | Cl | —CH(CH=CH₂)CH₂— |
| CH₃ | CF₃ | S | Cl | F | —CH(CH=CH₂)CH₂— |
| CH₃ | CF₃ | S | Cl | Cl | —CH(CH=CH₂)CH₂— |
| CF₃ | N(CH₃)₂ | O | Cl | F | —CH(CH=CH₂)CH₂— |
| CF₃ | N(CH₃)₂ | O | Cl | Cl | —CH(CH=CH₂)CH₂— |
| CF₃ | N(CH₃)₂ | S | Cl | F | —CH(CH=CH₂)CH₂— |
| CF₃ | N(CH₃)₂ | S | Cl | Cl | —CH(CH=CH₂)CH₂— |
| CF₃ | CF₃ | O | Cl | F | —CH(CH=CH₂)CH₂— |
| CF₃ | CF₃ | O | Cl | Cl | —CH(CH=CH₂)CH₂— |
| CF₃ | CF₃ | S | Cl | F | —CH(CH=CH₂)CH₂— |
| CF₃ | CF₃ | S | Cl | Cl | —CH(CH=CH₂)CH₂— |
| CH₂F | N(CH₃)₂ | O | Cl | F | —CH(CH=CH₂)CH₂— |
| CH₂F | N(CH₃)₂ | O | Cl | Cl | —CH(CH=CH₂)CH₂— |
| CH₂F | N(CH₃)₂ | S | Cl | F | —CH(CH=CH₂)CH₂— |
| CH₂F | N(CH₃)₂ | S | Cl | Cl | —CH(CH=CH₂)CH₂— |
| CH₂F | CF₃ | O | Cl | F | —CH(CH=CH₂)CH₂— |
| CH₂F | CF₃ | O | Cl | Cl | —CH(CH=CH₂)CH₂— |
| CH₂F | CF₃ | S | Cl | F | —CH(CH=CH₂)CH₂— |
| CH₂F | CF₃ | S | Cl | Cl | —CH(CH=CH₂)CH₂— |
| CH₃ | N(CH₃)₂ | O | Cl | F | —CH(C≡CH)CH₂— |
| CH₃ | N(CH₃)₂ | O | Cl | Cl | —CH(C≡CH)CH₂— |
| CH₃ | N(CH₃)₂ | S | Cl | F | —CH(C≡CH)CH₂— |
| CH₃ | N(CH₃)₂ | S | Cl | Cl | —CH(C≡CH)CH₂— |
| CH₃ | CF₃ | O | Cl | F | —CH(C≡CH)CH₂— |
| CH₃ | CF₃ | O | Cl | Cl | —CH(C≡CH)CH₂— |
| CH₃ | CF₃ | S | Cl | F | —CH(C≡CH)CH₂— |
| CH₃ | CF₃ | S | Cl | Cl | —CH(C≡CH)CH₂— |
| CF₃ | N(CH₃)₂ | O | Cl | F | —CH(C≡CH)CH₂— |
| CF₃ | N(CH₃)₂ | O | Cl | Cl | —CH(C≡CH)CH₂— |
| CF₃ | N(CH₃)₂ | S | Cl | F | —CH(C≡CH)CH₂— |
| CF₃ | N(CH₃)₂ | S | Cl | Cl | —CH(C≡CH)CH₂— |
| CF₃ | CF₃ | O | Cl | F | —CH(C≡CH)CH₂— |
| CF₃ | CF₃ | O | Cl | Cl | —CH(C≡CH)CH₂— |
| CF₃ | CF₃ | S | Cl | F | —CH(C≡CH)CH₂— |
| CF₃ | CF₃ | S | Cl | Cl | —CH(C≡CH)CH₂— |
| CH₂F | N(CH₃)₂ | O | Cl | F | —CH(C≡CH)CH₂— |
| CH₂F | N(CH₃)₂ | O | Cl | Cl | —CH(C≡CH)CH₂— |
| CH₂F | N(CH₃)₂ | S | Cl | F | —CH(C≡CH)CH₂— |
| CH₂F | N(CH₃)₂ | S | Cl | Cl | —CH(C≡CH)CH₂— |
| CH₂F | CF₃ | O | Cl | F | —CH(C≡CH)CH₂— |
| CH₂F | CF₃ | O | Cl | Cl | —CH(C≡CH)CH₂— |
| CH₂F | CF₃ | S | Cl | F | —CH(C≡CH)CH₂— |
| CH₂F | CF₃ | S | Cl | Cl | —CH(C≡CH)CH₂— |
| CH₃ | N(CH₃)₂ | O | Cl | F | —CH(CH₂CH₃)CH₂— |
| CH₃ | N(CH₃)₂ | O | Cl | Cl | —CH(CH₂CH₃)CH₂— |
| CH₃ | N(CH₃)₂ | S | Cl | F | —CH(CH₂CH₃)CH₂— |
| CH₃ | N(CH₃)₂ | S | Cl | Cl | —CH(CH₂CH₃)CH₂— |
| CH₃ | CF₃ | O | Cl | F | —CH(CH₂CH₃)CH₂— |
| CH₃ | CF₃ | O | Cl | Cl | —CH(CH₂CH₃)CH₂— |
| CH₃ | CF₃ | S | Cl | F | —CH(CH₂CH₃)CH₂— |
| CH₃ | CF₃ | S | Cl | Cl | —CH(CH₂CH₃)CH₂— |
| CF₃ | N(CH₃)₂ | O | Cl | F | —CH(CH₂CH₃)CH₂— |
| CF₃ | N(CH₃)₂ | O | Cl | Cl | —CH(CH₂CH₃)CH₂— |
| CF₃ | N(CH₃)₂ | S | Cl | F | —CH(CH₂CH₃)CH₂— |
| CF₃ | N(CH₃)₂ | S | Cl | Cl | —CH(CH₂CH₃)CH₂— |
| CF₃ | CF₃ | O | Cl | F | —CH(CH₂CH₃)CH₂— |
| CF₃ | CF₃ | O | Cl | Cl | —CH(CH₂CH₃)CH₂— |
| CF₃ | CF₃ | S | Cl | F | —CH(CH₂CH₃)CH₂— |
| CF₃ | CF₃ | S | Cl | Cl | —CH(CH₂CH₃)CH₂— |
| CH₂F | N(CH₃)₂ | O | Cl | F | —CH(CH₂CH₃)CH₂— |
| CH₂F | N(CH₃)₂ | O | Cl | Cl | —CH(CH₂CH₃)CH₂— |
| CH₂F | N(CH₃)₂ | S | Cl | F | —CH(CH₂CH₃)CH₂— |
| CH₂F | N(CH₃)₂ | S | Cl | Cl | —CH(CH₂CH₃)CH₂— |
| CH₂F | CF₃ | O | Cl | F | —CH(CH₂CH₃)CH₂— |
| CH₂F | CF₃ | O | Cl | Cl | —CH(CH₂CH₃)CH₂— |
| CH₂F | CF₃ | S | Cl | F | —CH(CH₂CH₃)CH₂— |
| CH₂F | CF₃ | S | Cl | Cl | —CH(CH₂CH₃)CH₂— |
| CH₃ | N(CH₃)₂ | O | Cl | F | —CH(CH₂F)CH₂— |
| CH₃ | N(CH₃)₂ | O | Cl | Cl | —CH(CH₂F)CH₂— |
| CH₃ | N(CH₃)₂ | S | Cl | F | —CH(CH₂F)CH₂— |
| CH₃ | N(CH₃)₂ | S | Cl | Cl | —CH(CH₂F)CH₂— |
| CH₃ | CF₃ | O | Cl | F | —CH(CH₂F)CH₂— |
| CH₃ | CF₃ | O | Cl | Cl | —CH(CH₂F)CH₂— |
| CH₃ | CF₃ | S | Cl | F | —CH(CH₂F)CH₂— |
| CH₃ | CF₃ | S | Cl | Cl | —CH(CH₂F)CH₂— |

TABLE III-continued $$\begin{array}{c} R^1 \\ | \\ R^3 \diagdown N \diagdown \diagup O \\ \phantom{R^3}\diagdown \phantom{N} \diagdown Z \\ N \diagdown N \diagup \diagdown AR^2 \\ \phantom{N}\diagup O \phantom{N} \diagdown Y \diagup X \end{array}$$

| $R^1$ | $R^3$ | A | X | Y | $R^2$ | Z |
|---|---|---|---|---|---|---|
| $CF_3$ | $N(CH_3)_2$ | O | Cl | F | | $-CH(CH_2F)CH_2-$ |
| $CF_3$ | $N(CH_3)_2$ | O | Cl | Cl | | $-CH(CH_2F)CH_2-$ |
| $CF_3$ | $N(CH_3)_2$ | S | Cl | F | | $-CH(CH_2F)CH_2-$ |
| $CF_3$ | $N(CH_3)_2$ | S | Cl | Cl | | $-CH(CH_2F)CH_2-$ |
| $CF_3$ | $CF_3$ | O | Cl | F | | $-CH(CH_2F)CH_2-$ |
| $CF_3$ | $CF_3$ | O | Cl | Cl | | $-CH(CH_2F)CH_2-$ |
| $CF_3$ | $CF_3$ | S | Cl | F | | $-CH(CH_2F)CH_2-$ |
| $CF_3$ | $CF_3$ | S | Cl | Cl | | $-CH(CH_2F)CH_2-$ |
| $CH_2F$ | $N(CH_3)_2$ | O | Cl | F | | $-CH(CH_2F)CH_2-$ |
| $CH_2F$ | $N(CH_3)_2$ | O | Cl | Cl | | $-CH(CH_2F)CH_2-$ |
| $CH_2F$ | $N(CH_3)_2$ | S | Cl | F | | $-CH(CH_2F)CH_2-$ |
| $CH_2F$ | $N(CH_3)_2$ | S | Cl | Cl | | $-CH(CH_2F)CH_2-$ |
| $CH_2F$ | $CF_3$ | O | Cl | F | | $-CH(CH_2F)CH_2-$ |
| $CH_2F$ | $CF_3$ | O | Cl | Cl | | $-CH(CH_2F)CH_2-$ |
| $CH_2F$ | $CF_3$ | S | Cl | F | | $-CH(CH_2F)CH_2-$ |
| $CH_2F$ | $CF_3$ | S | Cl | Cl | | $-CH(CH_2F)CH_2-$ |
| $CH_3$ | $N(CH_3)_2$ | O | Cl | F | | $-CH(CN)CH_2-$ |
| $CH_3$ | $N(CH_3)_2$ | O | Cl | Cl | | $-CH(CN)CH_2-$ |
| $CH_3$ | $N(CH_3)_2$ | S | Cl | F | | $-CH(CN)CH_2-$ |
| $CH_3$ | $N(CH_3)_2$ | S | Cl | Cl | | $-CH(CN)CH_2-$ |
| $CH_3$ | $CF_3$ | O | Cl | F | | $-CH(CN)CH_2-$ |
| $CH_3$ | $CF_3$ | O | Cl | Cl | | $-CH(CN)CH_2-$ |
| $CH_3$ | $CF_3$ | S | Cl | F | | $-CH(CN)CH_2-$ |
| $CH_3$ | $CF_3$ | S | Cl | Cl | | $-CH(CN)CH_2-$ |
| $CF_3$ | $N(CH_3)_2$ | O | Cl | F | | $-CH(CN)CH_2-$ |
| $CF_3$ | $N(CH_3)_2$ | O | Cl | Cl | | $-CH(CN)CH_2-$ |
| $CF_3$ | $N(CH_3)_2$ | S | Cl | F | | $-CH(CN)CH_2-$ |
| $CF_3$ | $N(CH_3)_2$ | S | Cl | Cl | | $-CH(CN)CH_2-$ |
| $CF_3$ | $CF_3$ | O | Cl | F | | $-CH(CN)CH_2-$ |
| $CF_3$ | $CF_3$ | O | Cl | Cl | | $-CH(CN)CH_2-$ |
| $CF_3$ | $CF_3$ | S | Cl | F | | $-CH(CN)CH_2-$ |
| $CF_3$ | $CF_3$ | S | Cl | Cl | | $-CH(CN)CH_2-$ |
| $CH_2F$ | $N(CH_3)_2$ | O | Cl | F | | $-CH(CN)CH_2-$ |
| $CH_2F$ | $N(CH_3)_2$ | O | Cl | Cl | | $-CH(CN)CH_2-$ |
| $CH_2F$ | $N(CH_3)_2$ | S | Cl | F | | $-CH(CN)CH_2-$ |
| $CH_2F$ | $N(CH_3)_2$ | S | Cl | Cl | | $-CH(CN)CH_2-$ |
| $CH_2F$ | $CF_3$ | O | Cl | F | | $-CH(CN)CH_2-$ |
| $CH_2F$ | $CF_3$ | O | Cl | Cl | | $-CH(CN)CH_2-$ |
| $CH_2F$ | $CF_3$ | S | Cl | F | | $-CH(CN)CH_2-$ |
| $CH_2F$ | $CF_3$ | S | Cl | Cl | | $-CH(CN)CH_2-$ |
| $CH_3$ | $N(CH_3)_2$ | O | Cl | F | | $-CH(CF_2H)CH_2-$ |
| $CH_3$ | $N(CH_3)_2$ | O | Cl | Cl | | $-CH(CF_2H)CH_2-$ |
| $CH_3$ | $N(CH_3)_2$ | S | Cl | F | | $-CH(CF_2H)CH_2-$ |
| $CH_3$ | $N(CH_3)_2$ | S | Cl | Cl | | $-CH(CF_2H)CH_2-$ |
| $CH_3$ | $CF_3$ | O | Cl | F | | $-CH(CF_2H)CH_2-$ |
| $CH_3$ | $CF_3$ | O | Cl | Cl | | $-CH(CF_2H)CH_2-$ |
| $CH_3$ | $CF_3$ | S | Cl | F | | $-CH(CF_2H)CH_2-$ |
| $CH_3$ | $CF_3$ | S | Cl | Cl | | $-CH(CF_2H)CH_2-$ |
| $CF_3$ | $N(CH_3)_2$ | O | Cl | F | | $-CH(CF_2H)CH_2-$ |
| $CF_3$ | $N(CH_3)_2$ | O | Cl | Cl | | $-CH(CF_2H)CH_2-$ |
| $CF_3$ | $N(CH_3)_2$ | S | Cl | F | | $-CH(CF_2H)CH_2-$ |
| $CF_3$ | $N(CH_3)_2$ | S | Cl | Cl | | $-CH(CF_2H)CH_2-$ |
| $CF_3$ | $CF_3$ | O | Cl | F | | $-CH(CF_2H)CH_2-$ |
| $CF_3$ | $CF_3$ | O | Cl | Cl | | $-CH(CF_2H)CH_2-$ |
| $CF_3$ | $CF_3$ | S | Cl | F | | $-CH(CF_2H)CH_2-$ |
| $CF_3$ | $CF_3$ | S | Cl | Cl | | $-CH(CF_2H)CH_2-$ |
| $CH_2F$ | $N(CH_3)_2$ | O | Cl | F | | $-CH(CF_2H)CH_2-$ |
| $CH_2F$ | $N(CH_3)_2$ | O | Cl | Cl | | $-CH(CF_2H)CH_2-$ |
| $CH_2F$ | $N(CH_3)_2$ | S | Cl | F | | $-CH(CF_2H)CH_2-$ |
| $CH_2F$ | $N(CH_3)_2$ | S | Cl | Cl | | $-CH(CF_2H)CH_2-$ |
| $CH_2F$ | $CF_3$ | O | Cl | F | | $-CH(CF_2H)CH_2-$ |
| $CH_2F$ | $CF_3$ | O | Cl | Cl | | $-CH(CF_2H)CH_2-$ |
| $CH_2F$ | $CF_3$ | S | Cl | F | | $-CH(CF_2H)CH_2-$ |
| $CH_2F$ | $CF_3$ | S | Cl | Cl | | $-CH(CF_2H)CH_2-$ |

FORMULATION

Compounds of this invention will generally be used in formulation with an agriculturally suitable carrier comprising a liquid or solid diluent or an organic solvent. Use formulations include dusts, granules, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents and solvents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced be agglomerating a fine powder composition; see for example, Cross et al., *Pesticide Formulations*, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are worked up in conventional ways. Compound numbers refer to compounds in Table IV.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 1 | 10.0% |
| attapulgite granules (low volatile matter, 0.71/0.30 mm; U.S.S. No. 25–50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

UTILITY

The compounds of the present invention are active postemergence and preemergence herbicides and especially for broadleaf and grass weed control in plantation crops including citrus, sugarcane, coffee, oil palm, rubber, pineapple, grapes, banana and conifers, such as loblolly pine. Most of the plantation crops are very important in mankind's diet while others are sources of useful raw materials. The compounds can be applied as preemergence or postemergence treatments using techniques of banding, directed sprays or broadcast applications. By selecting effective application rates, application techniques and adjuvants, compounds of this invention can be used for selective weed control in plantation crops.

Alternatively, compounds of this invention can be used in areas where complete control of all vegetation is desired, such as around fuel storage tanks, ammunition depots, industrial storage areas, oil well sites, drive-in theaters, around billboards, highways and railroad structures and in fence rows.

Effective application rates for the compounds of this invention are 5 to 5000 g/ha with a preferred rate range of 10 to 2000 g/ha. One skilled in the art can select the effective rates for a given situation.

The compounds of this invention may be used alone or in combination with other commercial herbicides, insecticides or fungicides. The following list exemplifies some of the herbicides suitable for use in mixtures. A combination of a compound from this invention with one or more of the following herbicides may be particularly useful for weed control in plantation crops.

Compounds of this invention can be used alone or in combination with other commercial herbicides, insecticides or fungicides. A mixture of one or more of the following herbicides with a compound of this invention may be particularly useful for weed control. Examples of other herbicides with which compounds of this invention can be formulated are: acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumesulam, flumipropyn, fluometuron, fluorochloridone, fluorodifen, fluoroglycofen, flupoxam, fluridone, fluroxypyr, fluazsulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(a,a-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, triallate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similar spectrum of control but a different mode of action will be particularly advantageous for resistance management.

A herbicidally effective amount of the compounds of this invention is determined by a number of factors. These factors include: formulation selected, method of application, amount and type of vegetation present, growing conditions, etc. In general, a herbicidally effective amount of a compound(s) of this invention is applied at rates from about 0.001 to 20 kg/ha with a preferred rate range of 0.004 to 0.25 kg/ha. One skilled in the art can easily determine application rates necessary for the desired level of weed control.

The following Tests demonstrate the control efficacy of the compounds of this invention specific weeds. The weed control afforded by the compounds is not limited, however, to these species. See Index Tables IV through VI for compound descriptions.

Selective herbicidal properties of the subject compounds were discovered in greenhouse tests as described below. Test procedures and results follows.

TABLE IV

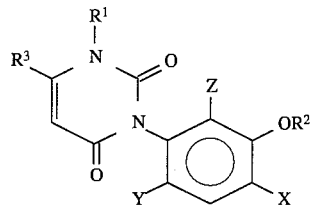

| No. | $R^1$ | $R^2$ | $R^3$ | X | Y | m.p. (°C.) | $^1$H-NMR |
|---|---|---|---|---|---|---|---|
| 1 | $CH_3$ | $CH_2Ph$ | $CF_3$ | Cl | F | 145–147 | 7.4 (m, 6H) 6.85 (d, 1H) 6.4 (s, 1H) 5.1 (s, 2H) 3.55 (s, 3H) |
| 2 | $CH_3$ | H | $CF_3$ | Cl | F | Foam | 7.15 (d, 1H) 6.9 (d, 1H) 6.4 (s, 1H) 5.8 (s, 1H) 3.6 (s, 3H) |
| 3 | $CH_3$ | $CH_2C\equiv CH$ | $CF_3$ | Cl | F | Foam | 7.35 (d, 1H) 7.0 (d, 1H) 6.4 (s, 1H) 4.78 (d, 2H) 3.58 (s, 3H) 2.6 (d, 1H) |
| 4 | $CH_2C\equiv CH$ | $CH_2C\equiv CH$ | $CF_3$ | Cl | F | Oil | 7.35 (d, 1H) 7.0 (d,1H) 6.4 (s, 1H) 4.75 (m, 4H) 2.6 (m, 1H) 2.4 (m, 1H) |
| 7 | $CH_2CH=CH_2$ | $CH_2CH=CH_2$ | $CF_3$ | Cl | F | Oil | 7.3 (d, 1H) 6.8 (d, 1H) 6.4 (s, 1H) 6.0 (m, 2H) 5.4 (m, 4H) 4.6 (d, 4H) |
| 9 | $CH_3$ | $CH_2CH=CH_2$ | $CF_3$ | Cl | F | 102–105 | 7.3 (d, 1H) 6.8 (d, 1H) 6.4 (s, 1H) 6.0 (m, 1H) 5.4 (m, 2H) 4.6 (d, 2H) 3.6 (s, 3H) |

TABLE V

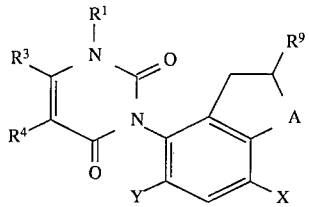

| No. | R¹ | R³ | R⁴ | R⁹ | X | Y | m.p. (°C.) | ¹H-NMR |
|---|---|---|---|---|---|---|---|---|
| 11 | $CH_3$ | $CF_3$ | H | $CH_3$ | Cl | F | Foam | 7.05 (d, 1H)<br>6.4 (s, 1H)<br>5.1 (m, 1H)<br>3.55 (s, 3H)<br>3.1 (m, 1H)<br>2.8 (m, 1H)<br>1.5 (d, 3H) |
| 12 | $CH_3$ | $CF_3$ | H | $CH_3$ | Cl | Cl | 64–66 | 7.3 (s, 1H)<br>6.4 (s, 1H)<br>5.1 (m, 1H)<br>3.6 (d, 3H)<br>3.25 (m, 1H)<br>2.75 (m, 1H)<br>1.54 (d, d 3H) |
| 13 | $CH_2C\equiv CH$ | $CF_3$ | H | $CH_3$ | Cl | F | Oil | 7.05 (d, 1H)<br>6.4 (s, 1H)<br>5.1 (m, 1H)<br>4.7 (d, 2H)<br>3.2 (m, 1H)<br>2.8 (m, 1H)<br>2.4 (s, 1H)<br>1.5 (s, 3H) |
| 14 | $CH_2CH_2CH_2$ | $CF_3$ | H | $CH_3$ | Cl | F | Oil | 7.05 (d, 1H)<br>6.4 (s, 1H)<br>5.9 (m, 1H)<br>5.3 (m, 2H)<br>5.1 (m, 1H)<br>4.6 (d, 1H)<br>3.2 (m, 1H)<br>2.8 (m, 1H)<br>1.5 (d, 3H) |
| 15 | $CH_2Ph$ | $CF_3$ | H | $CH_3$ | Cl | F | Oil | 7.2 (m, 7H)<br>7.0 (d, 1H)<br>6.4 (s, 1H)<br>5.2 (d, 2H)<br>5.1 (m, 1H)<br>3.1 (m, 1H)<br>2.7 (m, 1H)<br>1.5 (d, 3H) |
| 17 | $CH_3$ | $CH_3$ | H | $CH_3$ | Cl | F | Oil | 7.0 (d, 1H)<br>5.7 (s, 1H)<br>5.0 (m, 1H)<br>3.4 (s, 3H)<br>3.2 (d, d 1H)<br>2.8 (d, d 1H)<br>2.3 (s, 3H)<br>1.5 (d, 3H) |
| 19 | $CH_2CH_3$ | $CH_3$ | H | $CH_3$ | Cl | F | 140–142 | 7.0 (d, 1H)<br>5.68 (s, 1H)<br>5.05 (m, 1H)<br>3.95 (q, 1H)<br>3.2 (qu, 1H)<br>2.8 (qu, 1H)<br>2.35 (s, 3H)<br>1.55 (d, 3H)<br>1.3 (t, 3H) |
| 20 | $CH_3$ | $CF_3$ | H | $CO_2H$ | Cl | F | 190–194 | |
| 21 | $CH_3$ | $CF_3$ | H | $CO_2tBu$ | Cl | F | 65–67 | |
| 22 | $CH_3$ | $CF_3$ | H | $CO_2CH_3$ | Cl | F | 77–79 | |
| 23 | $CH_3$ | $CF_3$ | H | $CO_2iPr$ | Cl | F | 56–59 | |
| 24 | $CH_3$ | $CF_3$ | H | $CON(CH_3)_2$ | Cl | F | 92–94 | |
| 25 | $CH_3$ | $CF_3$ | H | $CH_2OC(O)CH_3$ | Cl | F | 58–61 | |

TABLE VI

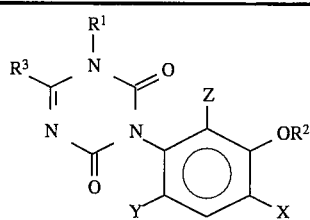

| No. | R¹ | R³ | X | Y | R² | m.p. (°C.) | ¹H-NMR |
|---|---|---|---|---|---|---|---|
| 5 | $CH_3$ | $N(CH_3)_2$ | Cl | F | H | 247–249 | 7.45 (d, 1H)<br>6.95 (d, 1H)<br>3.3 (s, 3H)<br>3.0 (s, 6H) |
| 6 | $CH_3$ | $N(CH_3)_2$ | Cl | F | $CH_2Ph$ | 193–194 | 7.4 (m, 6H)<br>6.95 (d, 1H)<br>5.05 (d, 2H)<br>3.45 (s, 3H)<br>3.1 (s, 6H) |
| 8 | $CH_3$ | $N(CH_3)_2$ | Cl | F | $CH_2C{\equiv}CH$ | 61–65 | 7.0 (d, 1H)<br>4.75 (m, 2H)<br>3.45 (s, 3H)<br>3.1 (s, 6H)<br>2.6 (m, 1H) |
| 16 | $CH_3$ | $N(CH_3)_2$ | Cl | F | H | 134–135 | 7.28 (s, 1H)<br>6.84 (d, 1H)<br>6.05 (m, 1H)<br>5.45 (d, 1H)<br>5.3 (d, 1H)<br>4.55 (s, 2H)<br>3.45 (s, 3H)<br>3.12 (s, 6H) |
| 18 | $CH_3$ | $N(CH_3)_2$ | Cl | F | $-CH(CH_3)CH_2-$ | 191–195 | 7.3 (d, 1H)<br>6.8 (d, 1H)<br>6.36 (s, 1H)<br>6.0 (m, 1H)<br>5.4 (m, 2H)<br>4.55 (d, 2H)<br>3.56 (s, 3H) |

TEST A

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*, cotton (*Gossypium hirsutum*), crabgrass (*Digitaria spp.*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response indicates no test result.

TABLE A

| Rate 400 g/ha | COMPOUND | | | | | | | | | |
|---|---|---|---|---|---|---|---|---|---|---|
|  | 1 | 2 | 3 | 5 | 6 | 8 | 11 | 16 | 17 | 18 |
| POSTEMERGENCE | | | | | | | | | | |
| Barley | 6 | 9 | 10 | 3 | 4 | 5 | 10 | — | 6 | 8 |
| Barnyardgrass | 9 | 10 | 10 | 5 | 3 | 10 | 10 | 7 | 9 | 10 |
| Bedstraw | 10 | 10 | 10 | 3 | 4 | 8 | 10 | — | 8 | 10 |
| Blackgrass | 10 | 9 | 10 | 3 | 4 | 5 | 10 | — | 5 | 9 |
| Cheatgrass | 7 | 8 | 10 | 4 | 4 | 5 | 10 | — | 5 | 10 |
| Chickweed | 10 | 10 | 10 | 3 | 4 | 8 | 10 | — | 5 | 10 |
| Cocklebur | 10 | 10 | 10 | 3 | 6 | 8 | 10 | 8 | 7 | 9 |
| Corn | 6 | 9 | 10 | 2 | 3 | 10 | 10 | 3 | 6 | 9 |
| Cotton | 10 | 10 | 10 | 9 | 9 | 10 | 10 | 10 | 10 | 10 |
| Crabgrass | 5 | 7 | 10 | 3 | 4 | 10 | 10 | 5 | 9 | 9 |
| Giant foxtail | 8 | 10 | 10 | 3 | 6 | 9 | 10 | 9 | 9 | 10 |
| Lambsquarter | 10 | 10 | 10 | 5 | 8 | 10 | 10 | — | 10 | 10 |
| Morningglory | 10 | 10 | 10 | 8 | 7 | 9 | 10 | 10 | 9 | 10 |
| Nutsedge | 5 | — | — | 1 | 0 | 9 | 7 | 2 | 2 | 5 |
| Rape | 10 | 7 | 10 | 1 | 5 | 9 | 10 | — | 7 | 10 |
| Rice | 6 | 7 | 10 | 3 | 3 | 9 | 10 | 7 | 9 | 9 |
| Sorghum | 6 | 9 | 10 | 2 | 3 | 6 | 10 | 4 | 9 | 10 |
| Soybean | 10 | 10 | 10 | 4 | 6 | 9 | 10 | 9 | 9 | 9 |
| Sugar beet | 10 | 10 | 10 | 5 | 9 | 10 | 10 | — | 10 | 10 |
| Velvetleaf | 10 | 10 | 10 | 2 | 9 | 10 | 10 | 10 | 10 | 10 |
| Wheat | 5 | — | — | 3 | 4 | 6 | 10 | — | 7 | 10 |

TABLE A-continued

| | | | | | | | | | | |
|---|---|---|---|---|---|---|---|---|---|---|
| Wild buckwheat | — | — | — | 6 | 6 | 10 | 10 | — | 10 | 10 |
| Wild oat | 9 | 9 | 10 | 2 | 4 | 6 | 10 | — | 8 | 10 |

PREEMERGENCE

| | | | | | | | | | | |
|---|---|---|---|---|---|---|---|---|---|---|
| Barley | 3 | 3 | 9 | 0 | 0 | 8 | 9 | — | 4 | 5 |
| Barnyardgrass | 9 | 9 | 10 | 0 | 0 | 9 | 10 | 9 | 10 | 10 |
| Bedstraw | 10 | 10 | 10 | 3 | 10 | 10 | 10 | — | 10 | 9 |
| Blackgrass | 10 | 7 | 10 | 0 | 5 | 9 | 10 | — | 4 | 10 |
| Cheatgrass | 10 | 10 | 10 | 0 | 0 | 9 | 10 | — | 9 | 10 |
| Chickweed | 10 | 9 | 10 | 0 | 3 | 10 | 10 | — | 4 | 9 |
| Cocklebur | 0 | 7 | 10 | 0 | 0 | 10 | 10 | 6 | 6 | 10 |
| Corn | 3 | 4 | 10 | 0 | 0 | 6 | 10 | 8 | 8 | 10 |
| Cotton | 8 | 8 | 10 | 0 | 0 | 10 | 10 | 6 | 8 | 10 |
| Crabgrass | 10 | 9 | 10 | 0 | 9 | 10 | 10 | 10 | 10 | 10 |
| Giant foxtail | 10 | 10 | 10 | 0 | 9 | 10 | 10 | 10 | 10 | 10 |
| Lambsquarter | 10 | 10 | 10 | 0 | 10 | 10 | 10 | — | 10 | 10 |
| Morningglory | 5 | 10 | 10 | 0 | 0 | 10 | 10 | 10 | 9 | 10 |
| Nutsedge | 2 | 10 | 10 | 0 | 10 | 1 | 7 | 3 | 4 | 5 |
| Rape | 10 | 10 | 10 | 1 | 2 | 10 | 10 | — | 10 | 10 |
| Rice | 5 | 3 | 10 | 0 | 0 | 10 | 10 | 6 | 9 | 10 |
| Sorghum | 7 | 9 | 10 | 0 | 0 | 4 | 10 | 8 | 9 | 10 |
| Soybean | 3 | 9 | 10 | 0 | 0 | 6 | 10 | 4 | 9 | 9 |
| Sugar beet | 10 | 10 | 10 | 1 | 9 | 10 | 10 | — | 10 | 10 |
| Velvetleaf | 10 | 10 | 10 | 0 | 10 | 10 | 10 | 10 | 10 | 10 |
| Wheat | 3 | 7 | 10 | 0 | 0 | 9 | 9 | — | 6 | 8 |
| Wild buckwheat | 10 | 10 | 10 | 0 | 10 | 10 | 10 | — | 10 | 10 |
| Wild oat | 9 | 9 | 10 | 0 | 0 | 10 | 10 | — | 3 | 10 |

| | COMPOUND | | |
|---|---|---|---|
| Rate 200 g/ha | 4 | 9 | 12 |

POSTEMERGENCE

| | | | |
|---|---|---|---|
| Barley | 5 | 7 | 7 |
| Barnyardgrass | 10 | 10 | 6 |
| Bedstraw | 9 | 10 | 9 |
| Blackgrass | 6 | 9 | 4 |
| Cheatgrass | 7 | 9 | 5 |
| Chickweed | 10 | 10 | 6 |
| Cocklebur | 7 | 10 | 7 |
| Corn | 9 | 9 | 7 |
| Cotton | 10 | 10 | 10 |
| Crabgrass | 9 | 10 | 7 |
| Giant foxtail | 9 | 10 | 8 |
| Lambsquarter | 10 | 10 | 10 |
| Morningglory | 9 | 10 | 9 |
| Nutsedge | 5 | 5 | 1 |
| Rape | 10 | 10 | 9 |
| Rice | 10 | 9 | 9 |
| Sorghum | 9 | 9 | 9 |
| Soybean | 9 | 9 | 10 |
| Sugar beet | 10 | 10 | 10 |
| Velvetleaf | 10 | 10 | 8 |
| Wheat | 7 | 6 | 7 |
| Wild buckwheat | 10 | 10 | 10 |
| Wild oat | 9 | 10 | 8 |

PREEMERGENCE

| | | | |
|---|---|---|---|
| Barley | 2 | 6 | 1 |
| Barnyardgrass | 10 | 10 | 9 |
| Bedstraw | 9 | 10 | 10 |
| Blackgrass | 9 | 10 | 8 |
| Cheatgrass | 9 | 10 | 3 |
| Chickweed | 10 | 10 | 1 |
| Cocklebur | 6 | 10 | 7 |
| Corn | 9 | 9 | 9 |
| Cotton | 7 | 9 | 3 |
| Crabgrass | 10 | 10 | 10 |
| Giant foxtail | 10 | 10 | 10 |
| Lambsquarter | 10 | 10 | 10 |
| Morningglory | 10 | 10 | 10 |
| Nutsedge | 10 | 2 | 0 |
| Rape | 8 | 10 | 10 |
| Rice | 9 | 9 | 8 |
| Sorghum | 9 | 10 | 7 |
| Soybean | 9 | 10 | 8 |
| Sugar beet | 9 | 10 | 10 |
| Velvetleaf | 10 | 10 | 10 |

TABLE A-continued

| | | | |
|---|---|---|---|
| Wheat | 7 | 9 | 2 |
| Wild buckwheat | 10 | 10 | 10 |
| Wild oat | 8 | 10 | 6 |

| | COMPOUND | | | | | | | | | |
|---|---|---|---|---|---|---|---|---|---|---|
| Rate 100 g/ha | 1 | 2 | 3 | 5 | 6 | 8 | 11 | 16 | 17 | 18 |

POSTEMERGENCE

| | | | | | | | | | | |
|---|---|---|---|---|---|---|---|---|---|---|
| Barley | 5 | 5 | 7 | 3 | 3 | 5 | 7 | — | 4 | 7 |
| Barnyardgrass | 8 | 7 | 10 | 1 | 2 | 4 | 10 | 3 | 8 | 9 |
| Bedstraw | 8 | 9 | 10 | 2 | 3 | 5 | 10 | — | 7 | 9 |
| Blackgrass | 6 | 5 | 10 | 2 | 2 | 5 | 10 | — | 4 | 6 |
| Cheatgrass | 6 | 5 | 9 | 1 | 3 | 4 | 10 | — | 3 | 5 |
| Chickweed | — | — | 10 | 2 | 2 | 6 | 10 | — | 4 | 8 |
| Cocklebur | 8 | 6 | 10 | 2 | 4 | 6 | 10 | 7 | 6 | 8 |
| Corn | 5 | 3 | 9 | 2 | 2 | 7 | 9 | 3 | 4 | 6 |
| Cotton | 10 | 10 | 10 | 9 | 10 | 10 | 10 | 10 | 10 | 10 |
| Crabgrass | 4 | 2 | 10 | 2 | — | 7 | 10 | 2 | 5 | 8 |
| Giant foxtail | 5 | 9 | 10 | 2 | 5 | 7 | 10 | 4 | 7 | 8 |
| Lambsquarter | 10 | 10 | 10 | 3 | 7 | 9 | 10 | — | 10 | 10 |
| Morningglory | 10 | 10 | 10 | 5 | 7 | 9 | 10 | 8 | 8 | 10 |
| Nutsedge | 5 | 2 | — | 0 | 0 | — | 8 | 0 | 2 | 3 |
| Rape | 10 | 3 | 10 | 1 | 2 | 7 | 10 | — | 5 | 9 |
| Rice | 5 | 6 | 9 | 3 | 3 | 6 | 10 | 4 | 9 | 8 |
| Sorghum | 5 | 4 | 9 | 1 | 2 | 5 | 10 | 4 | 5 | 8 |
| Soybean | 8 | 8 | 10 | 3 | 5 | 8 | 9 | 8 | 9 | 9 |
| Sugar beet | 10 | 10 | 10 | 3 | 7 | 10 | 10 | — | 9 | 10 |
| Velvetleaf | 10 | 10 | 10 | 2 | 6 | 7 | 10 | 10 | 9 | 10 |
| Wheat | 4 | 4 | 9 | 3 | 2 | 4 | 8 | — | 5 | 9 |
| Wild buckwheat | — | — | 10 | 3 | 3 | 10 | 10 | — | 9 | 9 |
| Wild oat | 7 | 5 | 9 | 3 | 3 | 4 | 9 | — | 6 | 9 |

PREEMERGENCE

| | | | | | | | | | | |
|---|---|---|---|---|---|---|---|---|---|---|
| Barley | 0 | 0 | 4 | 0 | 0 | 1 | 8 | — | 0 | 2 |
| Barnyardgrass | 8 | 3 | 10 | 0 | 0 | 3 | 10 | 2 | 8 | 9 |
| Bedstraw | 10 | 5 | 10 | 0 | 0 | 2 | 10 | — | 4 | 8 |
| Blackgrass | 9 | 3 | 10 | 0 | 0 | 5 | 10 | — | 2 | 6 |
| Cheatgrass | 5 | 2 | 8 | 0 | 0 | 4 | 10 | — | 1 | 8 |
| Chickweed | 10 | — | 10 | 0 | 2 | 5 | 10 | — | 2 | 9 |
| Cocklebur | 0 | 0 | 10 | 0 | 0 | 2 | 10 | 2 | 2 | 5 |
| Corn | 3 | 0 | 9 | 0 | 0 | 0 | 9 | 1 | 2 | 7 |
| Cotton | 0 | 0 | 10 | 0 | 0 | 1 | 10 | 2 | 4 | 10 |
| Crabgrass | 9 | 6 | 10 | 0 | 9 | 10 | 10 | 2 | 9 | 9 |
| Giant foxtail | 9 | 10 | 10 | 0 | 0 | 2 | 10 | 5 | 5 | 10 |
| Lambsquarter | 10 | 10 | 10 | 0 | 10 | 10 | 10 | — | 10 | 9 |
| Morningglory | 0 | 2 | 10 | 0 | 0 | 3 | 10 | 6 | 4 | 10 |
| Nutsedge | 0 | 8 | 7 | 0 | 0 | 0 | 5 | 2 | 1 | 4 |
| Rape | 10 | 3 | 10 | 0 | 0 | 9 | 10 | — | 6 | 9 |
| Rice | 1 | 1 | 9 | 0 | 0 | 6 | 9 | 3 | 4 | 8 |
| Sorghum | 3 | 1 | 9 | 0 | 0 | 3 | 10 | 1 | 1 | 6 |
| Soybean | 1 | 2 | 9 | 0 | 0 | 2 | 10 | 1 | 8 | 5 |
| Sugar beet | 5 | 7 | 10 | 0 | 0 | 7 | 10 | — | 9 | 9 |
| Velvetleaf | 2 | 10 | 10 | 0 | 0 | 10 | 10 | 6 | 10 | 10 |
| Wheat | 0 | 1 | 8 | 0 | 0 | 1 | 7 | — | 0 | 4 |
| Wild buckwheat | 10 | 0 | 10 | 0 | 0 | 8 | 10 | — | 10 | 9 |
| Wild oat | 7 | 3 | 9 | 0 | 0 | 0 | 9 | — | 0 | 5 |

| | COMPOUND | | |
|---|---|---|---|
| Rate 50 g/ha | 4 | 9 | 12 |

POSTEMERGENCE

| | | | |
|---|---|---|---|
| Barley | 4 | 5 | 5 |
| Barnyardgrass | 7 | 9 | 4 |
| Bedstraw | 9 | 10 | 6 |
| Blackgrass | 4 | 6 | 2 |
| Cheatgrass | 5 | 6 | 3 |
| Chickweed | 10 | 10 | 3 |
| Cocklebur | 6 | 10 | 4 |
| Corn | 5 | 7 | 4 |
| Cotton | 9 | 10 | 9 |
| Crabgrass | 6 | 9 | 5 |
| Giant foxtail | 7 | 9 | 7 |
| Lambsquarter | 10 | 10 | 9 |
| Morningglory | 8 | 10 | 6 |
| Nutsedge | 5 | 3 | 1 |

TABLE A-continued

| | | | |
|---|---|---|---|
| Rape | 10 | 10 | 5 |
| Rice | 8 | 8 | 7 |
| Sorghum | 7 | 8 | 5 |
| Soybean | 9 | 9 | 6 |
| Sugar beet | 10 | 10 | 9 |
| Velvetleaf | 8 | 10 | 5 |
| Wheat | 5 | 7 | 3 |
| Wild buckwheat | 10 | 10 | 9 |
| Wild oat | 5 | 7 | 4 |
| PREEMERGENCE | | | |
| Barley | 0 | 2 | 0 |
| Barnyardgrass | 7 | 9 | 7 |
| Bedstraw | 10 | 10 | 8 |
| Blackgrass | 5 | 9 | 5 |
| Cheatgrass | 5 | 8 | 2 |
| Chickweed | 10 | 10 | 0 |
| Cocklebur | 0 | 9 | 0 |
| Corn | 5 | 9 | 6 |
| Cotton | 2 | 7 | 2 |
| Crabgrass | 9 | 10 | 10 |
| Giant foxtail | 8 | 10 | 9 |
| Lambsquarter | 10 | 10 | 10 |
| Morningglory | 2 | 10 | 5 |
| Nutsedge | 5 | 3 | 0 |
| Rape | 2 | 10 | 7 |
| Rice | 2 | 9 | 7 |
| Sorghum | 3 | 9 | 6 |
| Soybean | 2 | 10 | 5 |
| Sugar beet | 9 | 10 | 10 |
| Velvetleaf | 9 | 10 | 9 |
| Wheat | 0 | 7 | 1 |
| Wild buckwheat | 9 | 10 | 5 |
| Wild oat | 5 | 8 | 1 |

TEST B

The compounds evaluated in this test were formulated in a non-phytoxic solvent and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (Amaranthusretroflexus), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*).

All plant species were planted one day before application of the compound for the preemergence portion of this test. Plantings of these species were adjusted to produce plants of appropriate size for the post-emergence portion of the test. Plant species in the flood test consisted of barnyardgrass (*Echinochloa crus-galli*), rice (*Oryza sativa*), umbrella sedge (*Cyperus difformis*) and duck salad (*Heteranthera limosa*). All plant species were grown using normal greenhouse practices. Visual evaluations of injury expressed on treated plants, when compared to untreated controls, were recorded approximately fourteen to twenty one days after application of the test compound. Plant response ratings, summarized in Table B, were recorded on a 0 to 100 scale where 0 is no effect and 100 is complete control. A dash (-) response indicates no test result.

TABLE B

| Rate 250 g/ha | COMPOUND 4 |
|---|---|
| POSTEMERGENCE | |
| Barley Igri | 70 |
| Barnyard 2 leaf | — |
| Barnyardgrass | 100 |
| Bedstraw | 100 |
| Blackgrass | 100 |
| Chickweed | 100 |
| Corn | 90 |
| Cotton | 100 |
| Crabgrass | 100 |
| Downy Brome | 100 |
| Duck salad | 15 |
| Giant foxtail | 100 |
| Lambsquarters | 100 |
| Morningglory | 100 |
| Pigweed | 100 |
| Rape | 100 |
| Rice Japonica | 100 |
| Ryegrass | 90 |
| Sorghum | 100 |
| Soybean | 100 |
| Speedwell | — |
| Sugar beet | 100 |
| Umbrella sedge | 10 |
| Velvetleaf | 100 |
| Wheat | 90 |
| Wild buckwheat | 100 |
| Wild oat | 90 |
| PREEMERGENCE | |
| Barley Igri | 50 |
| Bedstraw | 100 |
| Blackgrass | 100 |
| Chickweed | 100 |
| Corn | 100 |
| Cotton | 100 |
| Crabgrass | 100 |
| Downy Brome | 95 |
| Giant foxtail | 100 |
| Lambsquarters | 10) |
| Morningglory | 100 |
| Pigweed | 100 |
| Rape | 100 |
| Ryegrass | 100 |
| Sorghum | 100 |
| Soybean | 100 |
| Speedwell | — |
| Sugar beet | 100 |
| Velvetleaf | 100 |
| Wheat | 90 |
| Wild buckwheat | 100 |
| Wild oat | 95 |

| | COMPOUND | | | | |
|---|---|---|---|---|---|
| Rate 125 g/ha | 1 | 3 | 4 | 9 | 12 |
| POSTEMERGENCE | | | | | |
| Barley Igri | 0 | 100 | 60 | 95 | — |
| Barnyard 2 leaf | — | — | — | — | — |
| Barnyardgrass | 100 | 100 | 100 | 100 | 100 |
| Bedstraw | 100 | 100 | 100 | 100 | — |
| Blackgrass | 50 | 100 | 100 | 100 | — |
| Chickweed | 100 | 100 | 100 | 100 | — |
| Corn | 25 | 98 | 90 | 98 | — |
| Cotton | 100 | 100 | 100 | 100 | — |
| Crabgrass | 50 | 100 | 95 | 100 | — |

TABLE B-continued

| | | | | | |
|---|---|---|---|---|---|
| Downy Brome | 0 | 100 | 85 | 100 | — |
| Duck salad | 0 | 90 | 0 | 95 | 30 |
| Giant foxtail | 100 | 100 | 100 | 100 | — |
| Lambsquarters | 100 | 100 | 100 | 100 | — |
| Morningglory | 100 | 100 | 100 | 100 | — |
| Pigweed | 100 | 100 | 100 | 100 | — |
| Rape | 100 | 100 | 100 | 100 | — |
| Rice Japonica | 95 | 100 | 100 | 100 | 95 |
| Ryegrass | 40 | 100 | 70 | 100 | — |
| Sorghum | 60 | 100 | 90 | 100 | — |
| Soybean | 98 | 100 | 90 | 100 | — |
| Speedwell | 100 | 100 | — | 100 | — |
| Sugar beet | 100 | 100 | 100 | 100 | — |
| Umbrella sedge | 100 | 100 | 0 | 100 | 85 |
| Velvetleaf | 100 | 100 | 100 | 100 | — |
| Wheat | 0 | 100 | 60 | 95 | — |
| Wild buckwheat | 100 | 100 | 100 | 100 | — |
| Wild oat | 40 | 100 | 80 | 95 | — |

| | COMPOUND | | | |
|---|---|---|---|---|
| Rate 125 g/ha | 1 | 3 | 4 | 12 |
| PREEMERGENCE | | | | |
| Barley Igri | 0 | 100 | 30 | 50 |
| Bedstraw | 100 | 100 | 100 | 100 |
| Blackgrass | 30 | 100 | 90 | 90 |
| Chickweed | 100 | 100 | 100 | 0 |
| Corn | 50 | 100 | 70 | 90 |
| Cotton | 70 | 100 | 100 | 10 |
| Crabgrass | 100 | 100 | 100 | 100 |
| Downy Brome | 0 | 100 | 90 | 50 |
| Giant foxtail | 100 | 100 | 100 | 100 |
| Lambsquarters | 100 | 100 | 100 | 100 |
| Morningglory | 100 | 100 | 100 | 100 |
| Pigweed | 100 | 100 | 100 | 100 |
| Rape | 100 | 100 | 100 | 100 |
| Ryegrass | 20 | 100 | 95 | 90 |
| Sorghum | 60 | 100 | 90 | 100 |
| Soybean | 100 | 100 | 100 | 100 |
| Speedwell | 100 | 100 | — | 100 |
| Sugar beet | 100 | 100 | 100 | 100 |
| Velvetleaf | 100 | 100 | 100 | 100 |
| Wheat | 0 | 100 | 85 | 100 |
| Wild buckwheat | 100 | 100 | 100 | 100 |
| Wild oat | 0 | 100 | 75 | 90 |

| | COMPOUND | | | |
|---|---|---|---|---|
| Rate 62 g/ha | 1 | 3 | 4 | 11 |
| POSTEMERGENCE | | | | |
| Barley Igri | 0 | 95 | 50 | 90 |
| Barnyard 2 leaf | — | — | 100 | — |
| Barnyardgrass | 100 | 100 | 100 | 100 |
| Bedstraw | 100 | 100 | 100 | 100 |
| Blackgrass | 50 | 100 | 95 | 100 |
| Chickweed | 100 | 100 | 100 | 100 |
| Corn | 20 | 98 | 80 | 100 |
| Cotton | 100 | 100 | 100 | 100 |
| Crabgrass | 20 | 100 | 90 | 100 |
| Downy Brome | 0 | 100 | 75 | 90 |
| Duck salad | 0 | 90 | 0 | 90 |
| Giant foxtail | 80 | 100 | 95 | 100 |
| Lambsquarters | 100 | 100 | 100 | 100 |
| Morningglory | 100 | 100 | 100 | 100 |
| Pigweed | 100 | 100 | 100 | 100 |
| Rape | 100 | 100 | 100 | 100 |
| Rice Japonica | 90 | 100 | 95 | 100 |
| Ryegrass | 40 | 100 | 70 | 90 |
| Sorghum | 30 | 100 | 85 | 100 |
| Soybean | 98 | 100 | 100 | 100 |
| Speedwell | 100 | 100 | 100 | — |
| Sugar beet | 100 | 100 | 100 | 100 |
| Umbrella sedge | 90 | 100 | 0 | 90 |
| Velvetleaf | 100 | 100 | 100 | 100 |
| Wheat | 0 | 100 | 60 | 90 |

TABLE B-continued

| | | | | | |
|---|---|---|---|---|---|
| Wild buckwheat | 100 | 100 | 100 | 100 | |
| Wild oat | 40 | 100 | 60 | 95 | |
| PREEMERGENCE | | | | | |
| Barley Igri | 0 | 100 | 60 | 90 | |
| Bedstraw | 100 | 100 | 100 | 100 | |
| Blackgrass | — | 100 | 85 | 100 | |
| Chickweed | 100 | 100 | 100 | 100 | |
| Corn | 0 | 100 | 70 | 100 | |
| Cotton | 0 | 98 | 100 | 100 | |
| Crabgrass | 80 | 100 | 100 | 100 | |
| Downy Brome | 0 | 100 | 75 | 100 | |
| Giant foxtail | 100 | 100 | 100 | 100 | |
| Lambsquarters | 100 | 100 | 100 | 100 | |
| Morningglory | 100 | 100 | 100 | 100 | |
| Pigweed | 100 | 100 | 100 | 100 | |
| Rape | 50 | 100 | 100 | 100 | |
| Ryegrass | 0 | 100 | 95 | 100 | |
| Sorghum | 50 | 100 | 80 | 100 | |
| Soybean | 30 | 100 | 70 | 100 | |
| Speedwell | 100 | 100 | 100 | — | |
| Sugar beet | 100 | 100 | 100 | 100 | |
| Velvetleaf | 100 | 100 | 100 | 100 | |
| Wheat | 0 | 100 | 100 | 100 | |
| Wild buckwheat | 100 | 100 | 100 | 100 | |
| Wild oat | 0 | 100 | 70 | 100 | |

| | COMPOUND | | | | |
|---|---|---|---|---|---|
| Rate 31 g/ha | 1 | 3 | 4 | 9 | 12 |
| POSTEMERGENCE | | | | | |
| Barley Igri | 0 | 90 | 40 | 80 | — |
| Barnyard 2 leaf | — | — | — | — | — |
| Barnyardgrass | 100 | 100 | 95 | 100 | 70 |
| Bedstraw | 100 | 100 | 100 | 100 | — |
| Blackgrass | 30 | 100 | 60 | 80 | — |
| Chickweed | 90 | 100 | 100 | 100 | — |
| Corn | 20 | 70 | 60 | 90 | — |
| Cotton | 100 | 100 | 100 | 100 | — |
| Crabgrass | 0 | 100 | 70 | 90 | — |
| Downy Brome | 0 | 100 | 50 | 80 | — |
| Duck salad | 0 | 75 | 0 | 95 | 0 |
| Giant foxtail | 20 | 100 | 75 | 98 | — |
| Lambsquarters | 100 | 100 | 100 | 100 | — |
| Morningglory | 100 | 100 | 90 | 100 | — |
| Pigweed | 100 | 100 | 100 | 100 | — |
| Rape | 100 | 100 | 100 | 100 | — |
| Rice Japonica | 75 | 100 | 90 | 100 | 90 |
| Ryegrass | 30 | 100 | 60 | 95 | — |
| Sorghum | 20 | 100 | 70 | 95 | — |
| Soybean | 80 | 100 | 90 | 100 | — |
| Speedwell | 100 | 100 | — | 100 | — |
| Sugar beet | 100 | 100 | 100 | 100 | — |
| Umbrella sedge | 0 | 85 | 0 | 100 | 80 |
| Velvetleaf | 100 | 100 | 100 | 100 | — |
| Wheat | 0 | 100 | 50 | 50 | — |
| Wild buckwheat | 100 | 100 | 100 | 100 | — |
| Wild oat | 0 | 100 | 50 | 50 | — |

| | COMPOUND | | | |
|---|---|---|---|---|
| Rate 31 g/ha | 1 | 3 | 4 | 12 |
| PREEMERGENCE | | | | |
| Barley Igri | 0 | 90 | 0 | 20 |
| Bedstraw | 100 | 100 | 100 | 90 |
| Blackgrass | 0 | 100 | 70 | 40 |
| Chickweed | 100 | 100 | 100 | 0 |
| Corn | 0 | 100 | 40 | 60 |
| Cotton | 0 | 98 | 20 | 0 |
| Crabgrass | 80 | 100 | 100 | 98 |
| Downy Brome | 0 | 100 | 40 | 20 |
| Giant foxtail | 80 | 100 | 95 | 100 |
| Lambsquarters | 100 | 100 | 100 | 100 |
| Morningglory | 30 | 100 | 100 | 50 |
| Pigweed | 100 | 100 | 100 | 100 |

TABLE B-continued

| | COMPOUND | | | |
|---|---|---|---|---|
| Rate 16 g/ha | | | | |
| Rape | 20 | 100 | 40 | 50 |
| Ryegrass | 0 | 100 | 80 | 50 |
| Sorghum | 30 | 100 | 70 | 90 |
| Soybean | 20 | 100 | 70 | 40 |
| Speedwell | 100 | 100 | — | 100 |
| Sugar beet | 100 | 100 | 100 | 100 |
| Velvetleaf | 100 | 100 | 100 | 100 |
| Wheat | 0 | 100 | 40 | 50 |
| Wild buckwheat | 100 | 100 | 100 | 80 |
| Wild oat | 0 | 100 | 30 | 30 |

| | COMPOUND | | | |
|---|---|---|---|---|
| Rate 16 g/ha | 1 | 3 | 4 | 11 |
| POSTEMERGENCE | | | | |
| Barley Igri | 0 | 30 | 30 | 70 |
| Barnyard 2 leaf | — | — | 70 | — |
| Barnyardgrass | 100 | 100 | — | 100 |
| Bedstraw | 100 | 100 | 100 | 100 |
| Blackgrass | 0 | 100 | 40 | 95 |
| Chickweed | 90 | 100 | — | 100 |
| Corn | 10 | 60 | 40 | 80 |
| Cotton | 100 | 100 | 100 | 100 |
| Crabgrass | 0 | 70 | 30 | 70 |
| Downy Brome | 0 | 90 | 50 | 70 |
| Duck salad | 0 | 70 | 0 | 70 |
| Giant foxtail | 0 | 100 | 50 | 90 |
| Lambsquarters | 90 | 100 | — | 100 |
| Morningglory | 100 | 100 | 50 | 100 |
| Pigweed | 100 | 100 | 100 | 100 |
| Rape | 100 | 100 | 80 | 100 |
| Rice Japonica | 65 | 100 | 70 | 95 |
| Ryegrass | 0 | 100 | 40 | 90 |
| Sorghum | 0 | 98 | 50 | 90 |
| Soybean | 70 | 100 | 60 | 90 |
| Speedwell | 100 | 100 | 100 | — |
| Sugar beet | 100 | 100 | 100 | 100 |
| Umbrella sedge | 0 | 55 | 0 | 75 |
| Velvetleaf | 100 | 100 | 100 | 100 |
| Wheat | 0 | 60 | 30 | 90 |
| Wild buckwheat | 100 | 100 | 100 | 100 |
| Wild oat | 0 | 60 | 40 | 85 |
| PREEMERGENCE | | | | |
| Barley Igri | 0 | 50 | 0 | 70 |
| Bedstraw | 100 | 100 | 100 | 100 |
| Blackgrass | — | 100 | 50 | 90 |
| Chickweed | 80 | 100 | 100 | 90 |
| Corn | 0 | 80 | 0 | 90 |
| Cotton | 0 | 98 | 0 | 100 |
| Crabgrass | 50 | 100 | 50 | 100 |
| Downy Brome | 0 | 90 | 10 | 90 |
| Giant foxtail | 80 | 100 | 60 | 100 |
| Lambsquarters | 95 | 100 | 100 | 100 |
| Morningglory | 0 | 100 | 10 | 100 |
| Pigweed | 100 | 100 | 100 | 100 |
| Rape | 20 | 100 | 30 | 100 |
| Ryegrass | 0 | 100 | 60 | 95 |
| Sorghum | 20 | 100 | 10 | 100 |
| Soybean | 0 | 100 | 0 | 100 |
| Speedwell | 100 | 100 | 100 | — |
| Sugar beet | 80 | 100 | 90 | 100 |
| Velvetleaf | 95 | 100 | 100 | 100 |
| Wheat | 0 | 60 | 0 | 90 |
| Wild buckwheat | 100 | 100 | 100 | 100 |
| Wild oat | 0 | 95 | 0 | 90 |

| | COMPOUND | |
|---|---|---|
| Rate 8 g/ha | 9 | 12 |
| POSTEMERGENCE | | |
| Barley Igri | 60 | — |
| Barnyard 2 leaf | — | — |
| Barnyardgrass | 100 | 20 |
| Bedstraw | 100 | — |
| Blackgrass | 50 | — |
| Chickweed | 100 | — |
| Corn | 60 | — |
| Cotton | 100 | — |
| Crabgrass | 60 | — |
| Downy Brome | 50 | — |
| Duck salad | 80 | 0 |
| Giant foxtail | 80 | — |
| Lambsquarters | 100 | — |
| Morningglory | 100 | — |
| Pigweed | 100 | — |
| Rape | 90 | — |
| Rice Japonica | 95 | 45 |
| Ryegrass | 50 | — |
| Sorghum | 70 | — |
| Soybean | 100 | — |
| Speedwell | 100 | — |
| Sugar beet | 100 | — |
| Umbrella sedge | 90 | 0 |
| Velvetleaf | 100 | — |
| Wheat | 30 | — |
| Wild buckwheat | 100 | — |
| Wild oat | 30 | — |

| | COMPOUND |
|---|---|
| Rate 8 g/ha | 12 |
| PREEMERGENCE | |
| Barley Igri | 0 |
| Bedstraw | 20 |
| Blackgrass | 20 |
| Chickweed | 0 |
| Corn | 20 |
| Cotton | 0 |
| Crabgrass | 50 |
| Downy Brome | 0 |
| Giant foxtail | 60 |
| Lambsquarters | 70 |
| Morningglory | 20 |
| Pigweed | 100 |
| Rape | 20 |
| Ryegrass | 20 |
| Sorghum | 20 |
| Soybean | 20 |
| Speedwell | 70 |
| Sugar beet | 20 |
| Velvetleaf | 100 |
| Wheat | 20 |
| Wild buckwheat | 30 |
| Wild oat | 20 |

| | COMPOUND | | |
|---|---|---|---|
| Rate 4 g/ha | 3 | 4 | 11 |
| POSTEMERGENCE | | | |
| Barley Igri | — | 20 | 40 |
| Barnyard 2 leaf | — | 20 | — |
| Barnyardgrass | 50 | — | 80 |
| Bedstraw | — | 70 | 80 |
| Blackgrass | — | 40 | 50 |
| Chickweed | — | — | 60 |
| Corn | — | 30 | 50 |
| Cotton | — | 60 | 100 |
| Crabgrass | — | 20 | 50 |
| Downy Brome | — | 30 | 50 |
| Duck salad | 0 | 0 | 0 |
| Giant foxtail | — | 30 | 60 |
| Lambsquarters | — | — | 100 |
| Morningglory | — | 50 | 90 |
| Pigweed | — | 30 | 60 |
| Rape | — | 50 | 80 |
| Rice Japonica | 25 | 35 | 90 |
| Ryegrass | — | 30 | 75 |
| Sorghum | — | 40 | 50 |
| Soybean | — | 40 | 80 |
| Speedwell | — | 70 | — |

TABLE B-continued

| | | |
|---|---|---|
| Sugar beet | — | 90 | 85 |
| Umbrella sedge | 0 | 0 | 30 |
| Velvetleaf | — | 30 | 100 |
| Wheat | — | 30 | 50 |
| Wild buckwheat | — | 60 | 90 |
| Wild oat | — | 20 | 60 |

| | COMPOUND | |
|---|---|---|
| Rate 4 g/ha | 4 | 11 |
| PREEMERGENCE | | |
| Barley Igri | 0 | 30 |
| Bedstraw | 20 | 100 |
| Blackgrass | 10 | 30 |
| Chickweed | 70 | 70 |
| Corn | 0 | 60 |
| Cotton | 0 | 80 |
| Crabgrass | 0 | 85 |
| Downy Brome | 0 | 50 |
| Giant foxtail | 20 | 90 |
| Lambsquarters | 50 | 100 |
| Morningglory | 0 | 30 |
| Pigweed | 100 | 100 |
| Rape | 0 | 70 |
| Ryegrass | 0 | 60 |
| Sorghum | 0 | 60 |
| Soybean | 0 | 60 |
| Speedwell | 30 | — |
| Sugar beet | 0 | 95 |
| Velvetleaf | 20 | 100 |
| Wheat | 0 | 40 |
| Wild buckwheat | 0 | 100 |
| Wild oat | 0 | 50 |

| | COMPOUND | |
|---|---|---|
| Rate 2 g/ha | 9 | 12 |
| POSTEMERGENCE | | |
| Barley Igri | 30 | — |
| Barnyard 2 leaf | — | — |
| Barnyardgrass | 85 | 0 |
| Bedstraw | 100 | — |
| Blackgrass | 40 | — |
| Chickweed | 100 | — |
| Corn | 40 | — |
| Cotton | 90 | — |
| Crabgrass | 40 | — |
| Downy Brome | 30 | — |
| Duck salad | 30 | 0 |
| Giant foxtail | 50 | — |
| Lambsquarters | 100 | — |
| Morningglory | 70 | — |
| Pigweed | 100 | — |
| Rape | 60 | — |
| Rice Japonica | 80 | 20 |
| Ryegrass | 30 | — |
| Sorghum | 50 | — |
| Soybean | 80 | — |
| Speedwell | 100 | — |
| Sugar beet | 85 | — |
| Umbrella sedge | 90 | 0 |
| Velvetleaf | 100 | — |
| Wheat | 25 | — |
| Wild buckwheat | 100 | — |
| Wild oat | 25 | — |

| | COMPOUND |
|---|---|
| Rate 2 g/ha | 12 |
| PREEMERGENCE | |
| Barley Igri | 0 |
| Bedstraw | 0 |
| Blackgrass | 0 |
| Chickweed | 0 |
| Corn | 0 |
| Cotton | 0 |
| Crabgrass | 20 |
| Downy Brome | 0 |
| Giant foxtail | 20 |
| Lambsquarters | 0 |
| Morningglory | 20 |
| Pigweed | 20 |
| Rape | 0 |
| Ryegrass | 0 |
| Sorghum | 0 |
| Soybean | 0 |
| Speedwell | 0 |
| Sugar beet | 0 |
| Velvetleaf | 20 |
| Wheat | 0 |
| Wild buckwheat | 20 |
| Wild oat | 0 |

| | COMPOUND | | |
|---|---|---|---|
| Rate 1 g/ha | 3 | 4 | 11 |
| POSTEMERGENCE | | | |
| Barley Igri | — | 10 | 20 |
| Barnyard 2 leaf | — | 10 | — |
| Barnyardgrass | 20 | — | 0 |
| Bedstraw | — | 30 | 70 |
| Blackgrass | — | 20 | 30 |
| Chickweed | — | — | 30 |
| Corn | — | 20 | 30 |
| Cotton | — | 20 | 90 |
| Crabgrass | — | 10 | 10 |
| Downy Brome | — | 10 | 20 |
| Duck salad | 0 | 0 | 0 |
| Giant foxtail | — | 20 | 20 |
| Lambsquarters | — | — | 100 |
| Morningglory | — | 40 | 85 |
| Pigweed | — | 30 | 60 |
| Rape | — | 10 | 40 |
| Rice Japonica | 0 | 20 | 45 |
| Ryegrass | — | 10 | 30 |
| Sorghum | — | 20 | 20 |
| Soybean | — | 20 | 50 |
| Speedwell | — | 10 | — |
| Sugar beet | — | 40 | 70 |
| Umbrella sedge | 0 | 0 | 20 |
| Velvetleaf | — | 20 | 60 |
| Wheat | — | 10 | 20 |
| Wild buckwheat | — | 20 | 50 |
| Wild oat | — | 10 | 20 |

| | COMPOUND | |
|---|---|---|
| Rate 1 g/ha | 4 | 11 |
| PREEMERGENCE | | |
| Barley Igri | 0 | 0 |
| Bedstraw | 0 | 10 |
| Blackgrass | 0 | 0 |
| Chickweed | 0 | 70 |
| Corn | 0 | 0 |
| Cotton | 0 | 10 |
| Crabgrass | 0 | 10 |
| Downy Brome | 0 | 0 |
| Giant foxtail | 10 | 20 |
| Lambsquarters | 0 | 100 |
| Morningglory | 0 | 10 |
| Pigweed | 60 | 50 |
| Rape | 0 | 0 |
| Ryegrass | 0 | 10 |
| Sorghum | 0 | 0 |
| Soybean | 0 | 0 |
| Speedwell | 0 | — |
| Sugar beet | 0 | 20 |
| Velvetleaf | — | 100 |
| Wheat | 0 | 0 |

TABLE B-continued

| | | |
|---|---|---|
| Wild buckwheat | 0 | 60 |
| Wild oat | 0 | 10 |

TEST C

Compounds evaluated in this test were formulated in a non-phytoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), field violet (*Viola arvensis*), galium (*Galium aparine*), green foxtail (*Setaria viridis*), kochia (*Kochia scoparia*), lambsquarters (*Chenopodium album*), speedwell (*Veronica persica*), rape (*Brassica napus*), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*).

Blackgrass, galium and wild oat were treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table C, are based upon a 0 to 100 scale where 0 is no effect and 100 is complete control. A dash response (-) indicates no test result.

TABLE C

| Rate 125 g/ha | COMPOUND 12 |
|---|---|
| PREEMERGENCE | |
| Blackgrass (1) | 30 |
| Blackgrass (2) | 30 |
| Chickweed | 0 |
| Downy brome | 40 |
| Field violet | 100 |
| Galium (1) | 100 |
| Galium (2) | 100 |
| Green foxtail | 100 |
| Kochia | 100 |
| Lambsquarters | 100 |
| Persn Speedwell | 100 |
| Rape | 80 |
| Ryegrass | 90 |
| Sugar beet | 100 |
| Sunflower | 25 |
| Wheat (Spring) | 50 |
| Wheat (Winter) | 60 |

TABLE C-continued

| | |
|---|---|
| Wild buckwheat | 100 |
| Wild mustard | 100 |
| Wild oat (1) | 80 |
| Wild oat (2) | 90 |
| Wild radish | 100 |
| Winter Barley | 50 |

| Rate 64 g/ha | COMPOUND 1 |
|---|---|
| POSTEMERGENCE | |
| Blackgrass (1) | 0 |
| Blackgrass (2) | 0 |
| Chickweed | 55 |
| Downy brome | 0 |
| Field violet | 100 |
| Galium (1) | 94 |
| Galium (2) | 100 |
| Green foxtail | 35 |
| Kochia | 90 |
| Lambsquarters | — |
| Persn Speedwell | 70 |
| Rape | 90 |
| Ryegrass | 60 |
| Sugar beet | 100 |
| Sunflower | 55 |
| Wheat (Spring) | 0 |
| Wheat (Winter) | 0 |
| Wild buckwheat | 100 |
| Wild mustard | 100 |
| Wild oat (1) | 0 |
| Wild oat (2) | 0 |
| Wild radish | 85 |
| Winter Barley | 0 |

| Rate 64 g/ha | COMPOUND 1 | 12 |
|---|---|---|
| PREEMERGENCE | | |
| Blackgrass (1) | 20 | 10 |
| Blackgrass (2) | 20 | 20 |
| Chickweed | 100 | 0 |
| Downy brome | 20 | 20 |
| Field violet | 80 | 100 |
| Galium (1) | 100 | 100 |
| Galium (2) | 100 | 100 |
| Green foxtail | 100 | 100 |
| Kochia | 100 | 90 |
| Lambsquarters | — | 100 |
| Persn Speedwell | 100 | 100 |
| Rape | 65 | 60 |
| Ryegrass | 85 | 60 |
| Sugar beet | 100 | 100 |
| Sunflower | 25 | 20 |
| Wheat (Spring) | 0 | 40 |
| Wheat (Winter) | 0 | 45 |
| Wild buckwheat | 100 | 100 |
| Wild mustard | 100 | 100 |
| Wild oat (1) | 25 | 50 |
| Wild oat (2) | 30 | 55 |
| Wild radish | 60 | 80 |
| Winter Barley | 0 | 30 |

| Rate 32 g/ha | COMPOUND 1 | 9 |
|---|---|---|
| POSTEMERGENCE | | |
| Blackgrass (1) | 0 | 40 |
| Blackgrass (2) | 0 | 50 |
| Chickweed | 25 | 100 |
| Downy brome | 0 | 40 |
| Field violet | 100 | 100 |
| Galium (1) | 60 | 100 |
| Galium (2) | 65 | 100 |

TABLE C-continued

| | | |
|---|---|---|
| Green foxtail | 0 | 100 |
| Kochia | 60 | 100 |
| Lambsquarters | — | 100 |
| Persn Speedwell | 55 | 100 |
| Rape | 50 | 100 |
| Ryegrass | 30 | 100 |
| Sugar beet | 100 | 100 |
| Sunflower | 30 | 60 |
| Wheat (Spring) | 0 | 55 |
| Wheat (Winter) | 0 | 40 |
| Wild buckwheat | 95 | 100 |
| Wild mustard | 90 | 100 |
| Wild oat (1) | 0 | 60 |
| Wild oat (2) | 0 | 80 |
| Wild radish | 50 | — |
| Winter Barley | 0 | 40 |

| | COMPOUND | |
|---|---|---|
| Rate 32 g/ha | 1 | 12 |
| PREEMERGENCE | | |
| Blackgrass (1) | 0 | 0 |
| Blackgrass (2) | 0 | 0 |
| Chickweed | 85 | 0 |
| Downy brome | 0 | 20 |
| Field violet | 60 | 80 |
| Galium (1) | 75 | 80 |
| Galium (2) | 70 | 100 |
| Green foxtail | 100 | — |
| Kochia | 90 | 90 |
| Lambsquarters | — | 100 |
| Persn Speedwell | 90 | 100 |
| Rape | 35 | 0 |
| Ryegrass | 70 | 10 |
| Sugar beet | 95 | 100 |
| Sunflower | 0 | 0 |
| Wheat (Spring) | 0 | 20 |
| Wheat (Winter) | 0 | 25 |
| Wild buckwheat | 85 | 100 |
| Wild mustard | 70 | 100 |
| Wild oat (1) | 0 | 20 |
| Wild oat (2) | 0 | 40 |
| Wild radish | 45 | 50 |
| Winter Barley | 0 | 25 |

| | COMPOUND | |
|---|---|---|
| Rate 16 g/ha | 1 | 9 |
| POSTEMERGENCE | | |
| Blackgrass (1) | 0 | 35 |
| Blackgrass (2) | 0 | 20 |
| Chickweed | 0 | 100 |
| Downy brome | 0 | 40 |
| Field violet | 75 | 100 |
| Galium (1) | 30 | 100 |
| Galium (2) | 30 | 100 |
| Green foxtail | 0 | 100 |
| Kochia | 20 | 100 |
| Lambsquarters | — | 100 |
| Persn Speedwell | 30 | 100 |
| Rape | 25 | 80 |
| Ryegrass | 0 | 70 |
| Sugar beet | 90 | 100 |
| Sunflower | 0 | — |
| Wheat (Spring) | 0 | 50 |
| Wheat (Winter) | 0 | 30 |
| Wild buckwheat | 65 | 100 |
| Wild mustard | 55 | 100 |
| Wild oat (1) | 0 | 60 |
| Wild oat (2) | 0 | 60 |
| Wild radish | 25 | 100 |
| Winter Barley | 0 | 40 |

| | COMPOUND | |
|---|---|---|
| Rate 16 g/ha | 1 | 12 |
| PREEMERGENCE | | |
| Blackgrass (1) | 0 | 0 |
| Blackgrass (2) | 0 | 0 |
| Chickweed | 55 | 0 |
| Downy brome | 0 | 10 |
| Field violet | 30 | 40 |
| Galium (1) | 50 | 30 |
| Galium (2) | 45 | 40 |
| Green foxtail | 80 | 70 |
| Kochia | 60 | 0 |
| Lambsquarters | — | 80 |
| Persn Speedwell | 45 | 100 |
| Rape | 0 | 0 |
| Ryegrass | 40 | 0 |
| Sugar beet | 65 | 100 |
| Sunflower | 0 | 0 |
| Wheat (Spring) | 0 | 10 |
| Wheat (Winter) | 0 | 10 |
| Wild buckwheat | 60 | 70 |
| Wild mustard | 50 | 70 |
| Wild oat (1) | 0 | 0 |
| Wild oat (2) | 0 | 30 |
| Wild radish | 20 | 0 |
| Winter Barley | 0 | 10 |

| | COMPOUND | |
|---|---|---|
| Rate 8 g/ha | 1 | 9 |
| POSTEMERGENCE | | |
| Blackgrass (1) | 0 | 35 |
| Blackgrass (2) | 0 | 0 |
| Chickweed | 0 | 100 |
| Downy brome | 0 | 40 |
| Field violet | 35 | 100 |
| Galium (1) | 0 | 100 |
| Galium (2) | 0 | 100 |
| Green foxtail | 0 | 75 |
| Kochia | 0 | 100 |
| Lambsquarters | — | 100 |
| Persn Speedwell | 0 | 100 |
| Rape | 0 | 50 |
| Ryegrass | 0 | 30 |
| Sugar beet | 60 | 100 |
| Sunflower | 0 | 60 |
| Wheat (Spring) | 0 | 30 |
| Wheat (Winter) | 0 | 20 |
| Wild buckwheat | 25 | 100 |
| Wild mustard | 20 | 60 |
| Wild oat (1) | 0 | 20 |
| Wild oat (2) | 0 | 40 |
| Wild radish | 0 | 50 |
| Winter Barley | 0 | 20 |

| | COMPOUND |
|---|---|
| Rate 8 g/ha | 1 |
| PREEMERGENCE | |
| Blackgrass (1) | 0 |
| Blackgrass (2) | 0 |
| Chickweed | 25 |
| Downy brome | 0 |
| Field violet | 0 |
| Galium (1) | 30 |
| Galium (2) | 25 |
| Green foxtail | 35 |
| Kochia | 35 |
| Lambsquarters | — |
| Persn Speedwell | 20 |
| Rape | 0 |
| Ryegrass | 20 |
| Sugar beet | 45 |

TABLE C-continued

| | |
|---|---|
| Sunflower | 0 |
| Wheat (Spring) | 0 |
| Wheat (Winter) | 0 |
| Wild buckwheat | 30 |
| Wild mustard | 20 |
| Wild oat (1) | 0 |
| Wild oat (2) | 0 |
| Wild radish | 0 |
| Winter Barley | 0 |

| Rate 4 g/ha | COMPOUND 9 |
|---|---|
| POSTEMERGENCE | |
| Blackgrass (1) | 30 |
| Blackgrass (2) | 0 |
| Chickweed | 100 |
| Downy brome | 10 |
| Field violet | 100 |
| Galium (1) | 100 |
| Galium (2) | 100 |
| Green foxtail | 75 |
| Kochia | 100 |
| Lambsquarters | 100 |
| Persn Speedwell | 100 |
| Rape | 50 |
| Ryegrass | 0 |
| Sugar beet | 100 |
| Sunflower | 50 |
| Wheat (Spring) | 20 |
| Wheat (Winter) | 20 |
| Wild buckwheat | 50 |
| Wild mustard | 60 |
| Wild oat (1) | 10 |
| Wild oat (2) | 20 |
| Wild radish | 50 |
| Winter Barley | 15 |

| Rate 2 g/ha | COMPOUND 9 |
|---|---|
| POSTEMERGENCE | |
| Blackgrass (1) | 20 |
| Blackgrass (2) | 0 |
| Chickweed | 100 |
| Downy brome | 10 |
| Field violet | 50 |
| Galium (1) | 100 |
| Galium (2) | 40 |
| Green foxtail | 40 |
| Kochia | 70 |
| Lambsquarters | 70 |
| Persn Speedwell | 40 |

TABLE C-continued

| | |
|---|---|
| Rape | 0 |
| Ryegrass | 0 |
| Sugar beet | 80 |
| Sunflower | — |
| Wheat (Spring) | 20 |
| Wheat (Winter) | 20 |
| Wild buckwheat | — |
| Wild mustard | 40 |
| Wild oat (1) | 10 |
| Wild oat (2) | 10 |
| Wild radish | 30 |
| Winter Barley | 15 |

TEST D

Seeds, rhizomes, or plant parts of alfalfa (*Medicago sativa*), bermudagrass (*Cynodon dactylon*), broadleaf signalgrass (*Brachiaria plantyphylla*), common ragweed (*Ambrosia elatior*), dallisgrass (*Paspalum Dilatatum*), goosegrass (*Eleusine indica*), guineagrass (*Panicum maximum*), itchgrass (*Rottboellia exaltata*), johnsongrass (*Sorghum halepense*), ann bluegrass (*Poa annua*), large crabgrass (*Digitaria sanguinalis*), P. J. legume (*Pueraria javanica*), pitted morningglory (*Ipomoea lacunosa*), peanuts (*Arachis hypogaea*), purple nutsedge (*Cyperus rotundus*), sandbur (*Cenchrus echinatus*), smooth crabgrass (*Digitaria ischaemum*), common purslane (*Portulaca oleracea*), TX panicum (*Panicum texanum*) and yellow nutsedge (*Cyperus esculentus*) were planted into greenhouse pots containing greenhouse planting medium.

Each pot contained only one plant species. The test compound was dissolved in a non-phytotoxic solvent and applied preemergence and/or postemergence to the plants.

Preemergence applications were made within one day of planting the seeds or plant parts. Postemergence applications were applied when the plants were in the two to four leaf stage (three to twenty cm).

Test chemicals were dissolved in a non-phytotoxic solvent and applied preemergence and postemergence to the plants. Untreated control plants and treated plants were placed in the greenhouse and visually evaluated for injury at 13 to 21 days after herbicide application.

Plant response ratings, summarized in Table D, are based on a 0 to 100 scale where 0 is no injury and 100 is complete control. A dash (-) response indicates no test result.

TABLE D

| Rate 1000 g/ha | COMPOUND 8 |
|---|---|
| POSTEMERGENCE | |
| Alfalfa Var. | 30 |
| Ann Bluegrass | 30 |
| Bermudagrass | 60 |
| Brdlf Sgnlgrass | 70 |
| Cmn Purslane | 90 |
| Cmn Ragweed | — |
| Dallisgrass | 60 |
| Goosegrass | 60 |
| Guineagrass | 20 |
| Itchgrass | 30 |
| Johnsongrass | 50 |
| Large Crabgrass | 50 |
| P J Legume | — |
| Peanuts | 70 |

TABLE D-continued

|  | | |
|---|---|---|
| Pit Morninglory | 60 | |
| Purple Nutsedge | — | |
| S. Sandbur | 60 | |
| Smooth Crabgras | 40 | |
| Texas Panicum | 40 | |
| Yellow Nutsedge | — | |

| Rate 500 g/ha | COMPOUND | | |
|---|---|---|---|
|  | 3 | 8 | 16 |
| POSTEMERGENCE | | | |
| Alfalfa Var. | 100 | 40 | 0 |
| Ann Bluegrass | 100 | 40 | 0 |
| Bermudagrass | 100 | 80 | 0 |
| Brdlf Sgnlgrass | 100 | 100 | 0 |
| Cmn Purslane | 100 | 100 | 30 |
| Cmn Ragweed | — | — | 0 |
| Dallisgrass | 100 | 90 | 0 |
| Goosegrass | 100 | 90 | 0 |
| Guineagrass | 100 | 50 | 0 |
| Itchgrass | 100 | 50 | 0 |
| Johnsongrass | 100 | 70 | 0 |
| Large Crabgrass | 100 | 30 | 0 |
| P J Legume | — | — | — |
| Peanuts | 90 | 60 | 20 |
| Pit Morninglory | 100 | 70 | 0 |
| Purple Nutsedge | — | 0 | — |
| S. Sandbur | 100 | 20 | 0 |
| Smooth Crabgras | 100 | 50 | 0 |
| Texas Panicum | 100 | 20 | — |
| Yellow Nutsedge | — | 0 | — |

| Rate 500 g/ha | COMPOUND | |
|---|---|---|
|  | 8 | 16 |
| PREEMERGENCE | | |
| Alfalfa Var. | 80 | 0 |
| Ann Bluegrass | 100 | 0 |
| Bermudagrass | 100 | 90 |
| Brdlf Sgnlgrass | 100 | 0 |
| Cmn Purslane | 100 | 0 |
| Cmn Ragweed | — | 20 |
| Dallisgrass | 100 | 90 |
| Goosegrass | 100 | 80 |
| Guineagrass | 100 | 100 |
| Itchgrass | 80 | 0 |
| Johnsongrass | 100 | 0 |
| Large Crabgrass | 100 | 90 |
| Peanuts | 70 | 0 |
| Pit Morninglory | 90 | 0 |
| Purple Nutsedge | 80 | — |
| S. Sandbur | 100 | 0 |
| Smooth Crabgras | 100 | 100 |
| Texas Panicum | 90 | — |
| Yellow Nutsedge | 80 | — |

| Rate 250 g/ha | COMPOUND | | | | | | | | | | | | | | |
|---|---|---|---|---|---|---|---|---|---|---|---|---|---|---|---|
|  | 1 | 3 | 4 | 5 | 6 | 8 | 9 | 11 | 12 | 13 | 14 | 15 | 16 | 17 | 18 |
| POSTEMERGENCE | | | | | | | | | | | | | | | |
| Alfalfa Var. | 50 | 100 | 60 | 0 | 10 | 40 | 100 | 100 | 0 | 40 | 30 | 10 | 10 | 0 | 0 |
| Ann Bluegrass | 100 | 100 | 50 | 0 | 0 | 20 | — | 20 | 0 | — | — | — | 0 | 0 | 0 |
| Bermudagrass | 0 | 100 | 60 | 0 | 0 | 40 | 100 | 100 | 0 | 70 | 0 | 0 | 0 | 0 | 0 |
| Brdlf Sgnlgrass | 0 | 100 | 770 | 0 | 0 | 20 | 100 | 100 | 0 | 10 | 0 | 0 | 0 | 0 | 0 |
| Cmn Purslane | 100 | 100 | 100 | 0 | 0 | 100 | 100 | 100 | 90 | 100 | 80 | 70 | 20 | 20 | 20 |
| Cmn Ragweed | 90 | 100 | — | — | — | — | — | — | — | — | — | — | 0 | 100 | 100 |
| Dallisgrass | 50 | 100 | 90 | 0 | 0 | 0 | 100 | 100 | 0 | 70 | 0 | 0 | 0 | 0 | 0 |
| Goosegrass | 20 | 100 | 70 | 0 | 0 | 0 | 100 | 100 | 0 | 90 | 0 | 0 | 0 | 0 | 0 |
| Guineagrass | 0 | 100 | 50 | 0 | 0 | 10 | 100 | 100 | 0 | 0 | 0 | 0 | 0 | 0 | 0 |
| Itchgrass | 0 | 100 | 50 | 0 | 0 | 0 | 100 | 100 | 0 | 40 | 0 | 0 | 0 | 0 | 0 |
| Johnsongrass | 20 | 100 | 100 | 0 | 0 | 80 | 100 | 100 | 0 | 90 | 0 | 0 | 0 | 0 | 0 |
| Large Crabgrass | 0 | 100 | 60 | 0 | 0 | 20 | 100 | 100 | 0 | 100 | 0 | 0 | 0 | 0 | 0 |
| P J Legume | 20 | 100 | — | — | — | — | — | — | — | — | — | — | — | — | — |

TABLE D-continued

| Peanuts | 20 | 100 | 50 | 0 | 10 | 20 | 80 | 90 | 20 | 50 | 0 | 20 | 0 | 30 | 60 |
| Pit Morninglory | 0 | 100 | 90 | 0 | 0 | 30 | 100 | 100 | 0 | 50 | 0 | 0 | 0 | 0 | 30 |
| Purple Nutsedge | 0 | 90 | 0 | 0 | 0 | 0 | 70 | 90 | — | 0 | 0 | 10 | — | 0 | 0 |
| S. Sandbur | 0 | 100 | 60 | 0 | 0 | 0 | 100 | 100 | 0 | 0 | 0 | 0 | 0 | 0 | 0 |
| Smooth Crabgras | 0 | 100 | 60 | 0 | 0 | 0 | 100 | 100 | 0 | 0 | 0 | 0 | 0 | 0 | 0 |
| Texas Panicum | 0 | 100 | 90 | 0 | 0 | 0 | — | — | — | — | — | — | — | — | — |
| Yellow Nutsedge | 0 | 100 | 0 | 0 | 0 | 0 | 100 | 100 | — | 0 | 0 | 20 | — | 0 | 0 |
| PREEMERGENCE | | | | | | | | | | | | | | | |
| Alfalfa Var. | 80 | 100 | 100 | 0 | 0 | 50 | 100 | 100 | 100 | 0 | 0 | 0 | 0 | 20 | 60 |
| Ann Bluegrass | 20 | 100 | 100 | 0 | 0 | 70 | 100 | 100 | 60 | 70 | 0 | 0 | 0 | 0 | 100 |
| Bermudagrass | 20 | 100 | 100 | 0 | 0 | 100 | 100 | 100 | 100 | 100 | 90 | 30 | 40 | 30 | 100 |
| Brdlf Sgnlgrass | 0 | 100 | 100 | 0 | 0 | 70 | 100 | 100 | 90 | 0 | 0 | 0 | 0 | 0 | 100 |
| Cmn Purslane | 100 | 100 | 100 | 0 | 0 | 100 | 100 | 100 | 100 | 60 | 0 | 0 | 0 | 0 | 0 |
| Cmn Ragweed | 100 | 100 | — | — | — | — | — | — | — | — | — | — | 0 | 0 | 80 |
| Dallisgrass | 100 | 100 | 100 | 0 | 0 | 100 | 100 | 100 | 100 | 100 | 90 | 100 | 80 | 20 | 100 |
| Goosegrass | 100 | 100 | 100 | 0 | 0 | 100 | 100 | 100 | 100 | 100 | 90 | 100 | 0 | 90 | 100 |
| Guineagrass | 70 | 100 | 100 | 0 | 0 | 100 | 100 | 100 | 100 | 70 | 0 | 0 | 0 | 60 | 100 |
| Itchgrass | 0 | 100 | 100 | 0 | 0 | 60 | 100 | 100 | 80 | 20 | 0 | 0 | 0 | 0 | 70 |
| Johnsongrass | 30 | 100 | 100 | 0 | 0 | 90 | 100 | 100 | 100 | 0 | 0 | 0 | 0 | 0 | 770 |
| Large Crabgrass | 100 | 100 | 100 | 0 | 0 | 100 | 100 | 100 | 100 | 100 | 90 | 80 | 30 | 70 | 100 |
| Peanuts | 0 | 100 | 40 | 0 | 0 | 10 | 30 | 100 | 0 | 10 | 0 | 0 | 0 | 20 | 50 |
| Pit Morninglory | 50 | 100 | 80 | 0 | 0 | 70 | 100 | 100 | 60 | 0 | 0 | 0 | 0 | 20 | 60 |
| Purple Nutsedge | 0 | 100 | 10 | 0 | 0 | 80 | 50 | 90 | — | 0 | 0 | 0 | — | 0 | 0 |
| S. Sandbur | 0 | 100 | 100 | 0 | 0 | 70 | 100 | 100 | 100 | 90 | 0 | 0 | 0 | 0 | 100 |
| Smooth Crabgras | 100 | 70 | 100 | 0 | 0 | 100 | 100 | 100 | 100 | 100 | 30 | 100 | 80 | 70 | 100 |
| Texas Panicum | 90 | 100 | 100 | 0 | 0 | 90 | — | — | — | — | — | — | — | — | — |
| Yellow Nutsedge | 0 | 90 | 20 | 0 | 0 | 70 | 80 | 90 | — | 20 | 0 | 0 | — | 0 | 60 |

| | COMPOUND | | | | | | | | | | |
| --- | --- | --- | --- | --- | --- | --- | --- | --- | --- | --- | --- |
| Rate 125 g/ha | 1 | 2 | 3 | 8 | 9 | 11 | 12 | 13 | 14 | 15 | 16 |
| POSTEMERGENCE | | | | | | | | | | | |
| Alfalfa Var. | 50 | 70 | 100 | 0 | 100 | 100 | 0 | 0 | 0 | 0 | 10 |
| Ann Bluegrass | — | — | 100 | 0 | — | 0 | 0 | — | — | — | 0 |
| Bermudagrass | 0 | — | 100 | 0 | 80 | 100 | 0 | 0 | 0 | 0 | 0 |
| Brdlf Sgnlgrass | 0 | 0 | 100 | 0 | 100 | 100 | 0 | 0 | 0 | 0 | 0 |
| Cmn Purslane | 100 | 100 | 100 | 60 | 100 | 100 | 0 | 100 | 70 | 60 | 20 |
| Cmn Ragweed | 50 | 90 | 100 | — | — | — | — | — | — | — | 0 |
| Dallisgrass | 0 | 100 | 100 | 0 | 100 | 100 | 0 | 0 | 0 | 0 | 0 |
| Goosegrass | 0 | 80 | 100 | 0 | 100 | 100 | 0 | 0 | 0 | 0 | 0 |
| Guineagrass | 0 | 0 | 100 | 0 | 80 | 100 | 0 | 0 | 0 | 0 | 0 |
| Itchgrass | 0 | 0 | 100 | 0 | 60 | 90 | 0 | 0 | 0 | 0 | 0 |
| Johnsongrass | 20 | 0 | 100 | 0 | 100 | 100 | 0 | 0 | 0 | 0 | 0 |
| Large Crabgrass | 0 | 0 | 100 | 0 | 990 | 100 | 0 | 0 | 0 | 0 | 0 |
| P J Legume | 20 | 80 | 90 | — | — | — | — | — | — | — | — |
| Peanuts | 10 | 0 | 100 | 20 | 80 | 80 | 0 | 0 | 0 | 0 | 0 |
| Pit Morninglory | 0 | 40 | 100 | 30 | 100 | 100 | 0 | 0 | 0 | 0 | 0 |
| Purple Nutsedge | 0 | 0 | 90 | 0 | 60 | 80 | — | 0 | 0 | 0 | — |
| S. Sandbur | 0 | 0 | 100 | 0 | 100 | 100 | 0 | 0 | 0 | 0 | 0 |
| Smooth Crabgras | 0 | — | 100 | 0 | 80 | 80 | 0 | 0 | 0 | 0 | 0 |
| Texas Panicum | 0 | 0 | 100 | 0 | — | — | — | — | — | — | — |
| Yellow Nutsedge | 0 | 0 | 100 | 0 | 100 | 100 | — | 0 | 0 | 0 | — |
| PREEMERGENCE | | | | | | | | | | | |
| Alfalfa Var. | 0 | 50 | 100 | 0 | 100 | 100 | 80 | 0 | 0 | 0 | 0 |
| Ann Bluegrass | 0 | 0 | 100 | 10 | 100 | 100 | 0 | 60 | 0 | 0 | 0 |
| Bermudagrass | 0 | 30 | 100 | 100 | 100 | 100 | 100 | 100 | 70 | 30 | 0 |
| Brdlf Sgnlgrass | 0 | 0 | 100 | 10 | 100 | 100 | 0 | 0 | 0 | 0 | 0 |
| Cmn Purslane | 50 | 100 | 100 | 90 | 100 | 100 | 30 | 20 | 0 | 0 | 0 |
| Cmn Ragweed | 100 | 100 | 100 | — | — | — | — | — | — | — | 0 |
| Dallisgrass | 10 | 30 | 100 | 100 | 100 | 100 | 70 | 100 | 20 | 20 | 0 |
| Goosegrass | 10 | 90 | 100 | 100 | 100 | 100 | 100 | 100 | 90 | 90 | 0 |
| Guineagrass | 0 | 0 | 100 | 100 | 100 | 100 | 30 | 100 | 0 | 0 | 0 |
| Itchgrass | 0 | 0 | 100 | 50 | 100 | 100 | 0 | 0 | 0 | 0 | 0 |
| Johnsongrass | 0 | 0 | 100 | 50 | 100 | 100 | 0 | 30 | 0 | 0 | 0 |
| Large Crabgrass | 90 | 0 | 100 | 100 | 100 | 100 | 100 | 100 | 90 | 80 | 0 |
| Peanuts | 0 | 0 | 80 | 0 | 80 | 70 | 0 | 0 | 0 | 0 | 0 |
| Pit Morninglory | 0 | 0 | 100 | 0 | 100 | 100 | 50 | 0 | 0 | 0 | 0 |
| Purple Nutsedge | 0 | 70 | 90 | 10 | 10 | 80 | — | 0 | 0 | 0 | — |
| S. Sandbur | 0 | 90 | 100 | 0 | 100 | 100 | 0 | 0 | 0 | 0 | 0 |
| Smooth Crabgras | 20 | 0 | 100 | 100 | 100 | 100 | 90 | 100 | 0 | 0 | 0 |
| Texas Panicum | 20 | 0 | 100 | 0 | — | — | — | — | — | — | — |
| Yellow Nutsedge | 0 | 0 | 80 | 0 | 30 | 90 | — | 0 | 0 | 0 | — |

TABLE D-continued

| | COMPOUND | | |
|---|---|---|---|
| Rate 64 g/ha | 3 | 11 | 12 |
| POSTEMERGENCE | | | |
| Alfalfa Var. | 90 | 60 | 0 |
| Ann Bluegrass | 60 | 0 | 0 |
| Bermudagrass | 70 | 0 | 0 |
| Brdlf Sgnlgrass | 100 | 30 | 0 |
| Cmn Purslane | 100 | 100 | 40 |
| Cmn Ragweed | — | — | — |
| Dallisgrass | 100 | 0 | 0 |
| Goosegrass | 100 | 30 | 0 |
| Guineagrass | 100 | 0 | 0 |
| Itchgrass | 70 | 0 | 0 |
| Johnsongrass | 100 | 40 | 0 |
| Large Crabgrass | 100 | 0 | 0 |
| P J Legume | — | — | — |
| Peanuts | 100 | 30 | 0 |
| Pit Morninglory | 100 | 30 | 0 |
| Purple Nutsedge | 80 | — | — |
| S. Sandbur | 90 | 0 | 0 |
| Smooth Crabgras | 80 | 0 | 0 |
| Texas Panicum | 100 | — | — |
| Yellow Nutsedge | 100 | — | — |
| PREEMERGENCE | | | |
| Alfalfa Var. | 100 | 100 | 20 |
| Ann Bluegrass | 100 | 60 | 0 |
| Bermudagrass | 100 | 100 | 90 |
| Brdlf Sgnlgrass | 100 | 100 | 0 |
| Cmn Purslane | 100 | 100 | 80 |
| Cmn Ragweed | — | — | — |
| Dallisgrass | 100 | 100 | 100 |
| Goosegrass | 100 | 100 | 100 |
| Guineagrass | 100 | 100 | 90 |
| Itchgrass | 100 | 100 | 0 |
| Johnsongrass | 100 | 100 | 50 |
| Large Crabgrass | 100 | 100 | 100 |
| Peanuts | 40 | 60 | 0 |
| Pit Morninglory | 100 | 100 | 0 |
| Purple Nutsedge | 80 | — | — |
| S. Sandbur | 100 | 100 | 0 |
| Smooth Crabgras | 100 | 100 | 70 |
| Texas Panicum | 100 | — | — |
| Yellow Nutsedge | 80 | — | — |

| | COMPOUND | |
|---|---|---|
| Rate 32 g/ha | 3 | 11 |
| POSTEMERGENCE | | |
| Alfalfa Var. | 80 | 30 |
| Ann Bluegrass | 50 | 0 |
| Bermudagrass | 70 | 0 |
| Brdlf Sgnlgrass | 90 | 0 |
| Cmn Purslane | 100 | 100 |
| Cmn Ragweed | — | — |
| Dallisgrass | 90 | 0 |
| Goosegrass | 80 | 0 |
| Guineagrass | 40 | 0 |
| Itchgrass | 50 | 0 |
| Johnsongrass | 100 | 20 |
| Large Crabgrass | 20 | 0 |
| P J Legume | — | — |
| Peanuts | 70 | 50 |
| Pit Morninglory | 100 | 50 |
| Purple Nutsedge | 20 | — |
| S. Sandbur | 20 | 0 |
| Smooth Crabgras | 40 | 0 |
| Texas Panicum | 80 | — |
| Yellow Nutsedge | 20 | — |
| PREEMERGENCE | | |
| Alfalfa Var. | 70 | 100 |
| Ann Bluegrass | 90 | 30 |
| Bermudagrass | 100 | 100 |

TABLE D-continued

| | | |
|---|---|---|
| Brdlf Sgnlgrass | 90 | 30 |
| Cmn Purslane | 100 | 100 |
| Cmn Ragweed | — | — |
| Dallisgrass | 100 | 100 |
| Goosegrass | 100 | 100 |
| Guineagrass | 100 | 90 |
| Itchgrass | 100 | 60 |
| Johnsongrass | 90 | 70 |
| Large Crabgrass | 100 | 100 |
| Peanuts | 50 | 0 |
| Pit Morninglory | 100 | 20 |
| Purple Nutsedge | 60 | — |
| S. Sandbur | 100 | 80 |
| Smooth Crabgras | 100 | 100 |
| Texas Panicum | 90 | — |
| Yellow Nutsedge | 70 | — |

TEST E

Plastic windowsill flats were filled with planting medium and sprayed with the test compounds formulated in a non-phytotoxic spray solution. Treated soil was then placed in plastic bags and shaken thoroughly to incorporate the compounds in the soil. Seedings of cabbage (Early Copenhagen variety) and tomato (Rutgers Select and Ramapo VF FL hybrid varieties) were transplanted into the spiked soil. Untreated or antidote (naphthalic anyhdride) treated corn seeds were also planted into the spiked soil.

Plants were visually rated and compared with the appropriate controls. Injury ratings were based on a scale of 0 to 100 where 0 indicates no effect, 20 indicates minimal effect and 100 indicates complete control. Results are shown in Table E.

(*Imperata cylindrica*) rhizomes were planted in 20.3 cm plastic pots which also had volunteer fern (*Nephrolepis pectinata*) plants growing in them. In another test, guineagrass (*Panicum maximum*), *Paspalum conjugatum*, *Asystasia intrusa* and *Nephrolepis pectinata* plants were grown in planting medium in plastic pots. The plants were treated postemergence with the test compounds formulated in a non-phytotoxic spray solution.

Treated plants were visually rated at the end of the test and compared with the appropriate controls. Injury ratings were based on a scale of 0 to 100 where 0 indicates no effect, 20 indicates minimal effect and 100 indicates complete control. Results are shown in Table F.

TABLE E

| COMPOUND | Rate g/ha | Cabbage | Tomato Rutgers | Tomato Ramapo | Corn Untreated | Corn Treated |
|---|---|---|---|---|---|---|
| | | (14 DAT) | | | (10 DAT) | |
| 3 | 4 | 10 | 15 | 15 | 0 | 0 |
| | 8 | 45 | 85 | 75 | 0 | 0 |
| | 16 | 70 | 100 | 100 | 40 | 0 |
| | 32 | 100 | 100 | 100 | 70 | 10 |
| | 64 | 100 | 100 | 100 | 80 | 30 |
| | | (32 DAT) | | | (28 DAT) | |
| 3 | 4 | 0 | 0 | 0 | 0 | 0 |
| | 8 | 10 | 100 | 45 | 0 | 0 |
| | 16 | 60 | 100 | 100 | 25 | 0 |
| | 32 | 100 | 100 | 100 | 65 | 40 |
| | 64 | 100 | 100 | 100 | 90 | 70 |
| | | (14 DAT) | | | (10 DAT) | |
| 8 | 32 | 0 | 0 | 0 | 0 | 0 |
| | 64 | 0 | 0 | 0 | 0 | 0 |
| | 125 | 10 | 0 | 0 | 0 | 0 |
| | 250 | 65 | 15 | 5 | 0 | 0 |
| | 500 | 60 | 55 | 55 | 0 | 0 |
| | | (32 DAT) | | | (28 DAT) | |
| 8 | 32 | 0 | 0 | 0 | 0 | 0 |
| | 64 | 0 | 0 | 0 | 0 | 0 |
| | 125 | 0 | 0 | 0 | 0 | 0 |
| | 250 | 50 | 0 | 0 | 10 | 0 |
| | 500 | 55 | 30 | 20 | 10 | 0 |

TEST F

Sugarcane varieties CP70-321 and CP70-330 were planted in 15.2 cm plastic pots which were also seeded with large crabgrass (*Digitaria sanguinalis*) and Lalang

TABLE F

| COMPOUND | Rate g/ha | Sugarcane CP70-321 | Sugarcane CP70-330 | Large Crabgrass | Lalang | Fern |
|---|---|---|---|---|---|---|
| 3 | 32 | 0 | 0 | 50 | 30 | 0 |
|   | 64 | 0 | 0 | 60 | 30 | 0 |
|   | 125 | 0 | 0 | 85 | 30 | 0 |
| 8 | 500 | 0 | 0 | 0 | 0 | 0 |
|   | 1000 | 0 | 0 | 30 | 30 | 0 |
|   | 2000 | 0 | 0 | 60 | 60 | 20 |

| COMPOUND | Rate g/ha | Guineagrass | Paspalum Conjugalum | Asystasia intrusa | Nephrolepis pectinate |
|---|---|---|---|---|---|
| 11 | 64 | 40 | 0 | 45 | 0 |
|    | 125 | 50 | 0 | 40 | 0 |
|    | 250 | 75 | 30 | 50 | 0 |
|    | 500 | 80 | 45 | 60 | 0 |
| 12 | 64 | 0 | 0 | 0 | 0 |
|    | 125 | 0 | 0 | 0 | 0 |
|    | 250 | 30 | 0 | 0 | 0 |
|    | 500 | 30 | 0 | 0 | 0 |

TEST G

Sugarcane (*Saccharum officinarum*), purple nutsedge (*Cyperus rotundus*), *Brachiaria decumbens* and *Brachiaria plantaginea* were planted in fiberglass trays. Plants were treated postemergence with the test compounds formulated in a non-phytotoxic spray solution.

Treated plants were visually rated and compared with appropriate controls. Injury ratings were based on a scale of 0 to 100 where 0 indicates no effect, 20 indicates minimal effect and 100 indicates complete control. Results are shown in Table G.

TABLE G

| COMPOUND | Rate g/ha | Sugarcane | Purple nutsedge | Brachiaria decumbens | Brachiaria plantaginea |
|---|---|---|---|---|---|
| 8 | 500 | 0 | 20 | 90 | 60 |
|   | 1000 | 0 | 30 | 100 | 100 |
|   | 2000 | 20 | 60 | 100 | 100 |
| 11 | 32 | 0 | 0 | 0 | 0 |
|    | 64 | 10 | 0 | 70 | 60 |
|    | 125 | 30 | 0 | 90 | 90 |
| 12 | 64 | 0 | 0 | 0 | 0 |
|    | 125 | 0 | 0 | 0 | 0 |

TEST H

Pineapple (*Ananas comosus*), guineagrass (*Panicum maximum*) and swollen fingergrass (*Chloris inflata*) were planted in potting medium. Plants were treated postemergence with the test compound formulated in a non-phytotoxic spray solution.

Treatments were visually rated and compared with the appropriate controls. Injury ratings were based on a scale of 0 to 100 where 0 indicates no effect, 20 indicates minimal effect and 100 indicates complete control. Results are shown in Table H.

TABLE H

| COMPOUND | Rate g/ha | Pineapple | Guineagrass | Swollen fingergrass |
|---|---|---|---|---|
| 8 | 250 | 0 | 0 | 0 |
|   | 500 | 0 | 0 | 0 |
|   | 1000 | 0 | 30 | 0 |
|   | 2000 | 0 | 40 | 80 |

TEST I

Cuttings of turf species Zoysia spp., and St. Augustine (*Stenotaphrum secundatum*) were planted in 11.4 cm plastic pots filled with planting medium. Smooth crabgrass (*Digitaria ischaemum*) and large crabgrass (*Digitaria sanguinalis*) seeds were also planted and grown in 11.4 cm plastic pots. Plants were treated postemergence with the test compounds.

Treatments were visually rated at the end of the test and compared with the appropriate controls. Injury ratings were based on a scale of 0 to 100 where 0 indicates no effect, 20 indicates minimal effect and 100 indicates complete control. Results are shown in Table I.

TABLE I

| COMPOUND | Rate g/ha | Zoysia | St. Augustine | Smooth Crabgrass | Large Crabgrass |
|---|---|---|---|---|---|
| 3 | 4 | 0 | 0 | 0 | 0 |
|   | 8 | 0 | 0 | 0 | 0 |
|   | 16 | 0 | 0 | 10 | 40 |
|   | 32 | 0 | 0 | 10 | 50 |
|   | 64 | 0 | 0 | 30 | 70 |
| 8 | 64 | 0 | 0 | 0 | 0 |
|   | 125 | 30 | 0 | 0 | 50 |
|   | 250 | 50 | 20 | 20 | 90 |
|   | 500 | 50 | 20 | 40 | 90 |

TEST J

Fifteen different soybean varieties including Williams, W-20 and the Asgrow varieties A3242, A3935, A4715, A5979, A3322, A4009, A4906, A6297, A3205, A3733, A4595, A5403 and A6961 were planted separately in plastic pots filled with planting medium. The pots were tested preemergence with the test chemicals formulated in a non-phytotoxic spray solution.

Plants were visually rated at the end of the test and compared with the appropriate controls. Injury ratings were based on a scale of 0 to 100 where 0 indicates no effect, 20 indicates minimal effect and 100 indicates complete control. Results are shown in Table J.

the test chemicals formulated in a non-phytotoxic spray solvent.

Plants were visually rated at the end of the test and compared with appropriate controls. Injury ratings were based on a scale of 0 to 100 where 0 indicates no effect, 20 indicates minimal effect and 100 indicates complete control. Results are shown in Table K.

TABLE J

| COMPOUND | Rate g/ha | Williams | W20 | A3205 | A3242 | A3322 | A3733 | A3935 | A4009 |
|---|---|---|---|---|---|---|---|---|---|
| 11 | 16 | 20 | 20 | 20 | 20 | 20 | 30 | 20 | 40 |
|  | 32 | 60 | 50 | 50 | 60 | 50 | 50 | 70 | 70 |
|  | 64 | 90 | 90 | 80 | 90 | 90 | 90 | 90 | 90 |
|  | 125 | 100 | 100 | 100 | 100 | 100 | 100 | 100 | 100 |

| COMPOUND | Rate g/ha | A4595 | A4715 | A4906 | A5403 | A5979 | A6297 | A6961 |
|---|---|---|---|---|---|---|---|---|
| 11 | 16 | 20 | 30 | 60 | 50 | 40 | 60 | 20 |
|  | 32 | 60 | 70 | 60 | 60 | 70 | 100 | 100 |
|  | 64 | 90 | 90 | 90 | 90 | 90 | 90 | 90 |
|  | 125 | 100 | 100 | 100 | 100 | 100 | 100 | 100 |
| 12 | 16 | 0 | 0 | 0 | 0 | 0 | 0 | 0 |
|  | 32 | 0 | 0 | 0 | 0 | 0 | 0 | 0 |
|  | 64 | 0 | 0 | 0 | 0 | 0 | 0 | 0 |
|  | 125 | 20 | 20 | 20 | 20 | 20 | 20 | 20 |

TEST K

Corn, soybean, tomato, morningglory, different nightshade varieties [*Solanum nigrum* (entire and serrated leaf), *S. nigrum* subsp. nigrum, *S. interius, S. ptycanthus* (green berries and black berries), *S. nigrum* subsp. schultesii and triazine-tolerant nightshade] seeds and potato eye cuttings were planted in separate 11.4 cm plastic pots filled with planting medium. The pots were sprayed preemergence with

TABLE K

| COMPOUND | Rate g/ha | Corn | Soybean | Tomato | Morningglory | Triazine Tolerant Nightshade | Potato |
|---|---|---|---|---|---|---|---|
| 11 | 2 | 0 | 0 | 0 | 0 | 0 | 0 |
|  | 4 | 30 | 20 | 20 | 40 | 0 | 20 |
| 12 | 16 | 0 | 0 | 0 | 0 | 0 | 0 |
|  | 32 | 0 | 0 | 0 | 20 | — | 0 |
|  | 64 | 0 | 0 | 20 | 40 | 70 | 20 |
|  | 125 | 0 | 0 | 60 | 50 | 100 | 60 |

| COMPOUND | Rate g/ha | S. Nigrum Entire Leaf | S. Nigrum Serrated Leaf | S. Nigrum Subs. Nigrum | S. Interius | S. Ptyanthus Green Berries |
|---|---|---|---|---|---|---|
| 11 | 2 | 0 | 0 | 0 | 0 | 0 |
|  | 4 | 0 | 0 | 0 | 0 | 0 |
| 12 | 16 | 0 | 0 | 0 | 0 | 0 |
|  | 32 | 0 | 30 | 20 | 70 | 40 |
|  | 64 | 0 | 70 | 60 | 100 | 100 |
|  | 125 | 60 | 100 | 80 | 100 | 100 |

| COMPOUND | Rate g/ha | S. Ptyanthus Black Berries | S. Nigrum Sub. Schultesii |
|---|---|---|---|
| 11 | 2 | 0 | 0 |
|  | 4 | 0 | 0 |
| 12 | 16 | 0 | 0 |
|  | 32 | 0 | 0 |
|  | 64 | 50 | 20 |
|  | 125 | 70 | 60 |

TEST L

Rooted cuttings of rough lemon (*Citrus sp.*) were planted in 30 liter plastic pots. These pots were also seeded with guineagrass (*Panicum maximum*), sandbur (*Cenchrus enchinatus*) and pigweed (*Amaranthus viridis*). The weeds were cutback many times to simulate mowing and the citrus plant also trimmed.

The citrus was sprayed to simulate field type post-directed herbicide application while the weeds were treated postemergence over the top with the test compounds formulated in a non-phytotoxic spray solvent. In a separate test, loblolly pine seedlings were also sprayed over-the-top with the test compounds formulated in a non-phytotoxic spray solvent. Treated plants were visually rated and compared with appropriate controls. The injury ratings are based on the scale of 0 to 100 where 0 indicates no effect, 20 indicates minimal effect and 100 indicates complete control. The results are shown in Tables L1 and L2. The differences in results may be due to the fact that the tests were conducted using plants at different stages of growth.

TABLE L1

| | COMPOUND | | |
|---|---|---|---|
| Rate (500 g/ha) | 1 | 2 | 3 |
| POST-DIRECTED | | | |
| Rough Lemon | 0 | 0 | 0 |

| | COMPOUND | | |
|---|---|---|---|
| Rate (50 g/ha) | 1 | 2 | 3 |
| OVER-THE-TOP | | | |
| Guineagrass | 0 | 0 | 70 |
| Pigweed | 0 | 0 | 70 |
| Sandbur | 0 | 0 | 0 |

| | COMPOUND | | |
|---|---|---|---|
| Rate (250 g/ha) | 1 | 2 | 3 |
| POST-DIRECTED | | | |
| Rough Lemon | 0 | 0 | 0 |
| OVER-THE-TOP | | | |
| Guineagrass | 0 | 0 | 30 |
| Pigweed | 0 | 0 | 40 |
| Sandbur | 0 | 0 | 0 |

| | COMPOUND | | |
|---|---|---|---|
| Rate (125 g/ha) | 1 | 2 | 3 |
| POST-DIRECTED | | | |
| Rough Lemon | 0 | 0 | 0 |
| OVER-THE-TOP | | | |
| Guineagrass | 0 | 0 | 30 |
| Pigweed | 0 | 0 | 0 |
| Sandbur | 0 | 0 | 0 |

TABLE L2

| | COMPOUND | | | |
|---|---|---|---|---|
| Rate (250 g/ha) | 3 | 5 | 6 | 8 |
| POST-DIRECTED | | | | |
| Rough Lemon | 30* | 0 | 0 | 0 |
| OVER-THE-TOP | | | | |
| Loblolly pine | 70 | 0 | 0 | 0 |
| Guineagrass | 70 | 0 | 0 | 20 |
| Pigweed | 20 | 0 | 0 | 40 |
| Sandbur | 60 | 0 | 0 | 30 |

| | COMPOUND |
|---|---|
| Rate (125 g/ha) | 8 |
| POST-DIRECTED | |
| Rough Lemon | 0 |
| OVER-THE-TOP | |
| Loblolly pine | 0 |
| Guineagrass | 10 |
| Pigweed | 30 |
| Sandbur | 10 |

*Compound contacted leaves after treatment.

What is claimed is:

1. A method for controlling the growth of undesired vegetation in plantation crops selected from the group consisting of citrus, sugarcane, coffee, banana, oil palm, loblolly pine, rubber, cocoa, grapes, plantain, pineapple, fruit trees and nut trees which comprises applying to the locus of the crop an herbicidally effective amount of a compound of Formula I

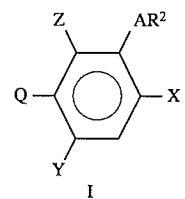

I wherein

Q is 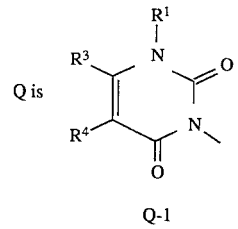

Q-1

A is O or S;

$R^1$ is $C_1$-$C_4$ alkyl optionally substituted with one or more halogen, $OR^5$, $SR^6$ or CN; $C_3$-$C_6$ alkenyl or $C_3$-$C_6$ alkynyl, each optionally substituted with 1–3 halogen atoms; formyl; or $C_2$-$C_6$ alkanoyl;

$R^2$ is H, isopropyl, allyl, propargyl, $CH(CH_3)C{=}CH$, benzyl, $CHR^7CO_2R^8$ or may be taken together with Z;

$R^3$ is $C_1$-$C_4$ alkyl, $C_1$-$C_4$ haloalkyl or $N(CH_3)_2$;

$R^4$ is H or halogen;

$R^5$ and $R^6$ are independently H or $C_1$-$C_3$ alkyl;

$R^7$ and $R^8$ are independently $C_1$-$C_2$ alkyl;

X is Cl or Br;

Y is F or Cl;

Z is H or may be taken together with $R^2$ as —$CH_2CHR^9$ such that the linking A atom is attached to the methine carbon;

$R^9$ is $C_1$-$C_3$ alkyl, $C_1$-$C_3$ haloalkyl, cyclopropyl, vinyl, $C_2$ alkynyl, CN, C(O)$R^{10}$, $CO_2R^{10}$, $CONR^{10}R^{11}$, $CR^{12}R^{13}C(O)R^{10}$, $CR^{12}R^{13}CO_2R^{10}$, $CR^{12}R^{13}CONR^{10}R^{11}$, $CHR^{12}OH$, $CHR^{12}OC(O)R^{10}$ or $CHR^{12}OC(O)NR^{10}R^{11}$; and $R^{10}$, $R^{11}$, $R^{12}$ and $R^{13}$ are independently H or $C_1$-$C_3$ alkyl.

2. The method of claim 1, wherein $R^1$ is $C_1$-$C_3$ alkyl optionally substituted with 1 to 3 F atoms or Cl atoms, O($C_1$-$C_2$ alkyl), S($C_1$-$C_2$ alkyl) or CN; $C_3$-$C_4$ alkenyl optionally substituted with 1 to 3 F atoms or Cl atoms; $C_3$-$C_4$ alkynyl; or $C_2$-$C_3$ alkanoyl;

$R^2$ is H, isopropyl, allyl, propargyl, $CH(CH_3)C\equiv CH$, $CHR^7CO_2R^8$ or may be taken together with Z;

$R^3$ is $C_1$-$C_2$ alkyl, $C_1$-$C_2$ haloalkyl or $N(CH_3)_2$;

$R^4$ is M, F, Cl or Br; and

X is Cl.

3. The method of claim 2, wherein $R^1$ is $CH_3$ optionally substituted with 1 to 3 F atoms or Cl atoms; $CH_2CN$; allyl; or propargyl;

$R^3$ is $CF_3$; and $R^4$ is H.

4. The method of claim 3, wherein $R^9$ is $CH_3$; and

A is O.

5. The method of claim 4, wherein the compound of Formula I is

3-[4-chloro-2-fluoro-5-[(2-propynyl)oxy]-phenyl]-1-methyl-6-(trifluoromethyl)-2,4-(1H,3H)-pyrimidinedione; or 3-[4-chloro-2-fluoro-5-(2-propenyloxy)-phenyl]-1-methyl-6-(trifluoromethyl)-2,4-(1H,3H)-pyrimidinedione; or 3-(5,7-dichloro-2,3-dihydro-2-methyl-4-benzofuranyl)-1-methyl-6-(trifluoromethyl)-2,4-(1H,3H)-pyrimidinedione; or 3-(7-choro-5-fluoro-2,3-dihydro-2-methyl-4-benzofuranyl)-1-methyl-6-(trifluoromethyl)-2,4(1H,3H)-pyrimidinedione.

6. The method of claim 1, wherein the compound of Formula I is applied in combination with at least one of the following: surfactant, solid or liquid diluent.

7. The method of claim 1 wherein the plantation crop is citrus.

8. A compound of Formula II

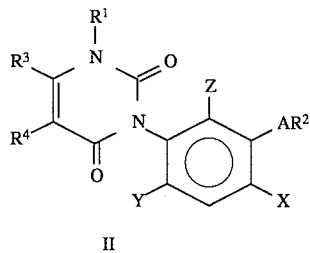

II wherein

A is O or S;

$R^1$ is $C_1$-$C_4$ alkyl optionally substituted with one or more halogen, $OR^5$, $SR^6$ or CN; $C_3$-$C_6$ alkenyl or $C_3$-$C_6$ alkynyl, each optionally substituted with 1–3 halogen atoms; formyl; or $C_2$-$C_6$ alkanoyl;

$R^2$ is H, isopropyl, allyl, propargyl, $CH(CH_3)C\equiv CH$, benzyl, $CHR^7CO_2R^8$ or may be taken together with Z;

$R^3$ is $C_1$-$C_4$ alkyl, $C_1$-$C_4$ haloalkyl or $N(CH_3)_2$;

$R^4$ is H or halogen;

$R^5$ and $R^6$ are independently H or $C_1$-$C_3$ alkyl;

$R^7$ and $R^8$ are independently $C_1$-$C_2$ alkyl;

X is Cl or Br;

Y is F or Cl;

Z is H or may be taken together with $R^2$ as $-CH_2CHR^9$ such that the linking A atom is attached to the methine carbon;

$R^9$ is $C_1$-$C_3$ alkyl, $C_1$-$C_3$ haloalkyl, cyclopropyl, vinyl, $C_2$ alkynyl, CN, C(O)$R^{10}$, $CO_2R^{10}$, $CONR^{10}R^{11}$, $CR^{12}R^{13}C(O)R^{10}$, $CR^{12}R^{13}CO_2R^{10}$, $CR^{12}R^{13}CONR^{10}R^{11}$, $CHR^{12}OH$, $CHR^{12}OC(O)R^{10}$ or $CHR^{12}OC(O)NR^{10}R^{11}$; and $R^{10}$, $R^{11}$, $R^{12}$ and $R^{13}$ are independently H or $C_1$-$C_3$ alkyl;

provided that 1) in compounds of Formula II, when $R^1$ is $C_1$-$C_4$ alkyl optionally substituted with halogen, $OR^5$ or CN; $C_3$-$C_4$ alkenyl; formyl; or $C_2$-$C_6$ alkanoyl; $R^3$ is $C_1$-$C_4$ haloalkyl; and $R^5$ is $C_1$-$C_3$ alkyl; then $R^2$ is benzyl or taken together with Z;

2) in compounds of Formula II, when $R^1$ is $CH_2OH$ or $C_1$-$C_3$ alkyl optionally substituted with halogen; $R^3$ is $C_1$-$C_4$ haloalkyl; and A is S; then $R^2$ is taken together with Z;

4) in compounds of Formula II, when $R^1$ is $C_1$-$C_4$ alkyl optionally substituted with halogen; formyl; or $C_2$-$C_6$ alkanoyl; then $R^2$ is taken together with Z.

9. A compound of claim 8 wherein $R^1$ is $C_1$-$C_3$ alkyl optionally substituted with 1 to 3 F atoms or Cl atoms, O($C_1$-$C_2$ alkyl), S ($C_1$-$C_2$ alkyl) or CN; $C_3$-$C_4$ alkenyl optionally substituted with 1 to 3 F atoms or Cl atoms; $C_3$-$C_4$ alkynyl; or $C_2$-$C_3$ alkanoyl;

$R^2$ is H, isopropyl, allyl, propargyl, $CH(CH_3)C\equiv CH$, $CHR^7CO_2R^8$ or may be taken together with Z;

$R^3$ is $C_1$-$C_2$ alkyl, $C_1$-$C_2$ haloalkyl or $N(CH_3)_2$;

$R^4$ is H, F, Cl or Br; and

X is Cl.

10. A compound of claim 9 wherein $R^1$ is $CH_3$ optionally substituted with 1 to 3 F atoms or Cl atoms; $CH_2CN$; allyl; or propargyl;

$R^3$ is $CF_3$; and $R_4$ is H.

11. A compound of claim 10 wherein $R^9$ is $CH_3$; and

A is O.

12. A compound of claim 8 wherein the compound is 3-(5,7-dichloro-2,3-dihydro-2-methyl-4-benzofuranyl)-1-methyl-6-(trifluoromethyl)-2,4(1H,3H)-pyrimidinedione; or 3-(7-choro-5-fluoro-2,3-dihydro-2-methyl-4-benzofuranyl)-1-methyl-6-(trifluoromethyl)-2,4(1H,3H)-pyrimidinedione.

13. A method for controlling the growth of undesired vegetation in plantation crops selected from the group consisting of citrus, sugarcane, coffee, banana, oil palm, loblolly pine, rubber, cocoa, grapes, plantain, pineapple, fruit trees and nut trees which comprises applying to the locus of the crop to be protected an effective amount of a compound of claim 8, 9, 10 or 11.

14. A method for controlling the growth of undesired vegetation in plantation crops selected from the group consisting of citrus, sugarcane, coffee, banana, oil palm, loblolly pine, rubber, cocoa, grapes, plantain, pineapple, fruit trees and nut trees which comprises applying to the locus of the crop to be protected an effective amount of a compound of claim 12.

15. A method for controlling the growth of undesired vegetation in plantation crops selected from the group consisting of citrus, sugarcane, coffee, banana, oil palm, loblolly pine, rubber, cocoa, grapes, plantain, pineapple, fruit trees and nut trees which comprises applying to the locus of the crop to be protected an effective amount of a composition which comprises an effective amount of a compound of claim 8, 9, 10 or 11, and at least one of the following: surfactant, solid or liquid diluent.

16. A method for controlling the growth of undesired vegetation in plantation crops selected from the group consisting of citrus, sugarcane, coffee, banana, oil palm, loblolly pine, rubber, cocoa, grapes, plantain, pineapple, fruit trees and nut trees which comprises applying to the locus of the crop to be protected an effective amount of a composition which comprises an effective amount of a compound of claim 12, and at least one of the following: surfactant, solid or liquid diluent.

* * * * *

UNITED STATES PATENT AND TRADEMARK OFFICE
CERTIFICATE OF CORRECTION

PATENT NO. : 5,602,077
DATED : February 11, 1997
INVENTOR(S) : Kofi Sam Amuti et al.

It is certified that error appears in the above-identified patent and that said Letters Patent is hereby corrected as shown below:

Columns 51 and 52, Table V, compound no. 14, delete "$CH_2CH_2CH_2$" and insert -- $CH_2CH=CH_2$ --.

Column 84, line 65, delete "$-CH_2CHR^9$" and insert -- $-CH_2\overset{|}{C}HR^9$ --.

Column 85, line 15, delete "$R^4$ is M," and insert -- $R^4$ is H,--.

Column 86, line 6, delete "$-CH_2CHR^9$" and insert -- $-CH_2\overset{|}{C}HR^9$ --.

Signed and Sealed this

Twenty-third Day of December, 1997

Attest:

BRUCE LEHMAN

Attesting Officer    Commissioner of Patents and Trademarks